US011408883B2

(12) United States Patent
Orwar et al.

(10) Patent No.: US 11,408,883 B2
(45) Date of Patent: *Aug. 9, 2022

(54) MULTI-PROTEASE METHOD

(71) Applicant: OBLIQUE THERAPEUTICS AB, Gothenburg (SE)

(72) Inventors: Owe Orwar, Hovås (SE); Carolina Trkulja, Borås (SE); Max Davidson, Gothenburg (SE); Jessica Hägglund, Vallentuna (SE)

(73) Assignee: OBLIQUE THERAPEUTICS AB, Gothenburg (SE)

( * ) Notice: Subject to any disclaimer, the term of this patent is extended or adjusted under 35 U.S.C. 154(b) by 74 days.

This patent is subject to a terminal disclaimer.

(21) Appl. No.: 16/339,810

(22) PCT Filed: Oct. 6, 2017

(86) PCT No.: PCT/EP2017/075532
§ 371 (c)(1),
(2) Date: Apr. 5, 2019

(87) PCT Pub. No.: WO2018/065599
PCT Pub. Date: Apr. 12, 2018

(65) Prior Publication Data
US 2020/0041499 A1    Feb. 6, 2020

(30) Foreign Application Priority Data
Oct. 6, 2016  (GB) ..................................... 1617002

(51) Int. Cl.
*G01N 33/543*  (2006.01)
*G01N 33/68*   (2006.01)
*C12Q 1/37*    (2006.01)

(52) U.S. Cl.
CPC ............ *G01N 33/543* (2013.01); *C12Q 1/37* (2013.01); *G01N 33/6878* (2013.01); *G01N 2560/00* (2013.01)

(58) Field of Classification Search
CPC ............ G01N 33/543; G01N 33/6878; G01N 2560/00; C12Q 1/37
See application file for complete search history.

(56) References Cited

U.S. PATENT DOCUMENTS

| 9,476,888 | B2 * | 10/2016 | Blagoev ............. | G01N 33/6854 |
| 2004/0002118 | A1 * | 1/2004 | Smilansky ......... | G01N 33/6818 435/7.1 |
| 2004/0072251 | A1 | 4/2004 | Anderson | |
| 2004/0185038 | A1 | 9/2004 | Carr et al. | |
| 2006/0292639 | A1 | 12/2006 | Mansson et al. | |
| 2008/0146502 | A1 | 6/2008 | Collier et al. | |
| 2012/0052592 | A9 | 3/2012 | Maekawa et al. | |
| 2012/0128646 | A1 * | 5/2012 | Haskins ............. | G01N 33/6893 424/93.71 |
| 2012/0263728 | A1 | 10/2012 | Baker | |
| 2015/0241450 | A1 | 8/2015 | Liu et al. | |
| 2015/0309046 | A1 | 10/2015 | Blagoev et al. | |

FOREIGN PATENT DOCUMENTS

| EP | 2 174 908 | 4/2010 |
| EP | 2 186 879 | 5/2010 |
| JP | 2008-175814 | 7/2008 |
| WO | 92/07083 | 4/1992 |
| WO | 96/29412 | 9/1996 |
| WO | 2005/019266 | 3/2005 |
| WO | 2006/005472 | 1/2006 |
| WO | 2006/047417 | 5/2006 |
| WO | 2006/068619 | 6/2006 |
| WO | 2008/120684 | 10/2008 |
| WO | 2009/136382 | 11/2009 |
| WO | 2016/156545 | 10/2016 |

OTHER PUBLICATIONS

Freund et al., "Targeting endogenous nuclear antigens by electrotransfer of monoclonal antibodies in living cells", mAbs, vol. 5, No. 4, pp. 518-522, 2013.
Karlsson et al., "Subcellular localization of an ATPase in anammox bacteria using proteomics and immunogold electron microscopy", FEMS Microbiology Letters, vol. 354, pp. 10-18, 2014.
Han et al., "Mass Spectrometry for Proteomics", Current Opinion in Chemical Biology, vol. 12, No. 5, pp. 483-490, 2008.
Buckinx et al., "Transient Receptor Potential Vanilloid Type I Channel (TRPVI) Immunolocalization in the Murine Enteric Nervous System Is Affected by the Targeted C-terminal Epitope of the Applied Antibody" Journal of Histochemistry and Cytochemistry, vol. 61, No. 6, pp. 421-432, 2013.
Hager-Braun et al., "Determination of protein-derived epitopes by mass spectometry", Expert Rev. Proteomics, vol. 2, No. 5, pp. 745-756, 2005.
Cabral et al., "Biophysical Studies on the BEX3, the p75NTR_Associated Cell Death Executor, reveal a High-Order Oligomer with Partially Folded Regions", PLoS ONE, vol. 10, No. 9, 0137916, 2015.
Cassady-Cain et al., "Biophysical Characterization and Activity of Lymphostatin, a Multifunctional Virulence Factor of Attaching and Effacing *Escherichia coli*", The Journal of Biological Chemistry, vol. 291, No. 11, pp. 5803-5816, 2016.
El-Kased et al., "A Novel Mass Spectra metric Epitope Mapping Approach Without Immobilization of the Antibody", Journal of Proteomics & Bioinformatics, vol. 4, No. 1, pp. 001-009, 2011.

(Continued)

*Primary Examiner* — Changhwa J Cheu
(74) *Attorney, Agent, or Firm* — Wenderoth, Lind & Ponack, L.L.P.

(57) ABSTRACT

The present invention relates to methods of identifying an epitope on a protein that can be bound by an antibody. Methods of the invention typically involve a step of limited or restricted proteolysis of a protein using a single first protease or a combination of first proteases, and a further proteolysis step using a single second protease or combination of second proteases. The invention also relates to identified epitopes and to antibodies which bind to epitopes that have been identified by methods of the invention.

19 Claims, 20 Drawing Sheets
Specification includes a Sequence Listing.

(56) References Cited

OTHER PUBLICATIONS

Hilton et al., "A new structural insight into XPA-DNA interactions" Bioscience Reports, vol. 34, No. 6, pp. 831-840, 2014.
Lassaux et al., "A Structure-Based Strategy for Epitope Discovery in *Burkholderia pseudomallei* OppA Antigen", Structure, vol. 21, pp. 167-175, 2013.
Myrum et al., "Arc is a flexible modular protein capable of reversible self-oligomerization", Biochemical Journal, vol. 468, pp. 145-158, 2015.
Rajabi et al., "A comparison of the folding characteristics of free and ribosome-tethered polypeptide chains using limited proteolysis and mass spectrometry" Protein Science, vol. 24, pp. 1282-1291, 2015.
Saxena et al., "Nucleotide-Induced Conformational Changes in *Escherichia coli* DnaA Protein Are Required for Bacterial ORC to Pre-RC Conversion at the Chromosomal Origin", International Journal of Molecular Sciences, vol. 16, pp. 27897-27911, 2015.
Suckau et al., "Molecular epitope identification by limited proteolysis of an immobilized antigen-antibody complex and mass spectrometric peptide mapping" Proc. Natl. Acad. Sci. USA, vol. 87, pp. 9848-9852, 1990.
Zhang et al., "Analysis of Monoclonal Antibody Sequence and Post-translational Modifications by Time-controlled Proteolysis and Tandem Mass Spectrometry", Molecular & Cellular Proteomics (ASBMB), vol. 15, No. 4, pp. 1479-1488, 2016.
Hitomi et al., "Immunological Detection of Proteolytically Activated Epidermal-type Transglutaminase (TGase 3) Using Cleavage-site-specific Antibody", Bioscience Biotechnology and Biochemistry, vol. 67, No. 11, pp. 2492-2494, 2003.
Yu et al., "Protease Cleavage Sites in HIV-1 gp120 Recognized by Antigen Processing Enzymes Are Conserved and Located at Receptor Binding Sites", Journal of Virology, vol. 84, No. 3, pp. 1513-1526, 2009.
Roberts et al., "The major envelope glycoprotein of the extracellular virion of *Autographa californica* nuclear polyhedrosis virus possesses at least three distinct neutralizing epitopes" Virus Research, vol. 28, No. 3, pp. 285-297, 1993.
Larvor et al. "Peptide/Antibody Recognition: Synthetic Peptides Derived From the *E. coli* Tryptophan Synthase β2 Subunit Interact With High Affinity With an Anti-β2 Monoclonal Antibody", Molecular Immunology, vol. 28, No. 4/5, pp. 523-531, 1991.
Koenig et al., "Detailed Analysis of the Repeat Domain of Dystrophin Reveals Four Potential Hinge Segments That May Confer Flexibility", Journal of Biological Chemistry, vol. 265, No. 8, pp. 4560-4566, 1990.
Friguet et al., "Polypeptide-Antibody Binding Mechanism: Conformational Adaptation Investigated By Equilibrium and Kinetic Analysis", Research in Immunology, vol. 140, No. 4, pp. 355-376, 1989.
Jannson et al., "Effect of cholesterol depletion on the pore dilation of TRPV1", Molecular Pain, vol. 9, No. 1, pp. 1-8, 2013.
Trkulja et al., "Thesis for the Degree of Doctor of Philosophy: Epitope-discovery for sequence-targeting antibody therapeutics", Paper IV, pp. 1-15, 2015 XP055422399.
Trkulja et al., "Probing structure and function of ion channels using limited proteolysis and microfluidics—Supporting Information", Journal of the American Chemical Society, 136(42):S1-S28 (2014).
International Search Report and Written Opinion of the International Searching Authority, dated Feb. 12, 2018 in corresponding International Patent Application No. PCT/EP2017/075532.
Carolina L Trkulja: "Thesis for the Degree of Doctor of Philosophy: Methods for elucidating membrane protein structure and function", XP055422399: (2015).
Trkulja et al., "Probing Structure and Function of Ion Channels Using Limited Proteolysis and Microfluidics", Journal of the American Chemical Society, 136(42): 14875-14882 (2014).
Jansson et al., "Microfluidic Flow Cell for Sequential Digestion of Immobilized Proteoliposomes", Analytical Chemisuy, 84(13): 5582-5588 (2012).
Stefanescu et al., "Mass spectrometric approaches for elucidation of antigen-antibody recognition structures in molecular immunology", Eur. J. Mass Spectrom, 2007, vol. 13, pp. 69-75.
Mazzoni M.R. et al., "Proteolytic Fragmentation for Epitope Mapping", Methods in Molecular Biology, Epitope Mapping Protocols, Human Press, 2009, Reineke U. and M. Schutkowski eds. pp. 77-86.
Langton, B.C. et al., "Structural Features of an Antigen Required for Cellular Interactions and for T Cell Activation in a MHC-Resuicted Response", The Journal of Immunology, 1988, vol. 141, No. 2, pp. 447-456.
Yurchenco, P.D. et al., "Monoclonal Antibodies as Probes of Domain Structure of the Spectrin a Subunit", The Journal of Biological Chemistry, 1982, vol. 257, No. 15, pp. 9102-9107.
Guo, Xiaofeng et al., "Confetti: A Multiprotease Map of the HeLa Proteome for Comprehensive Proteomics", Molecular & Cellular Proteomics, 2014, vol. 13, pp. 1573-1584.

* cited by examiner

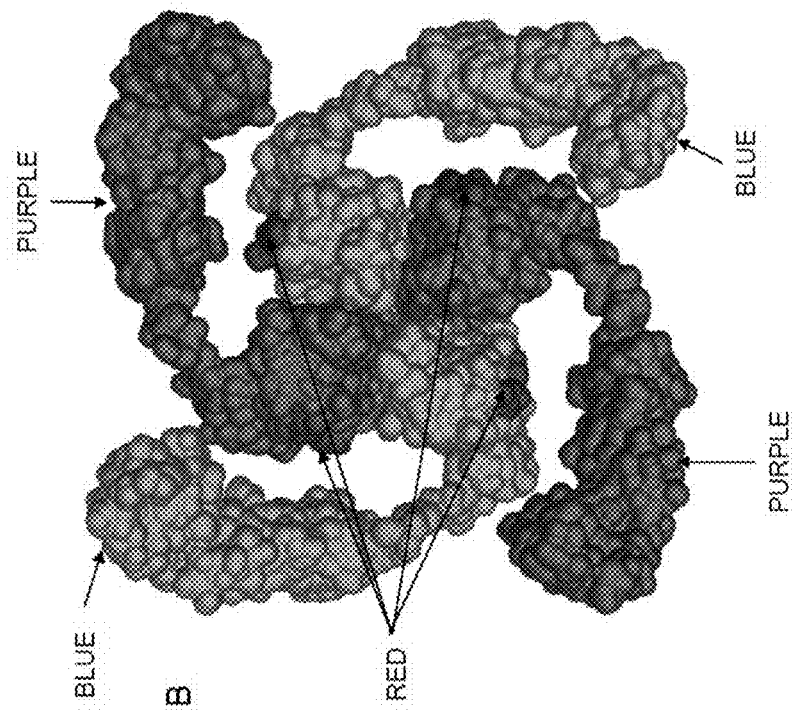
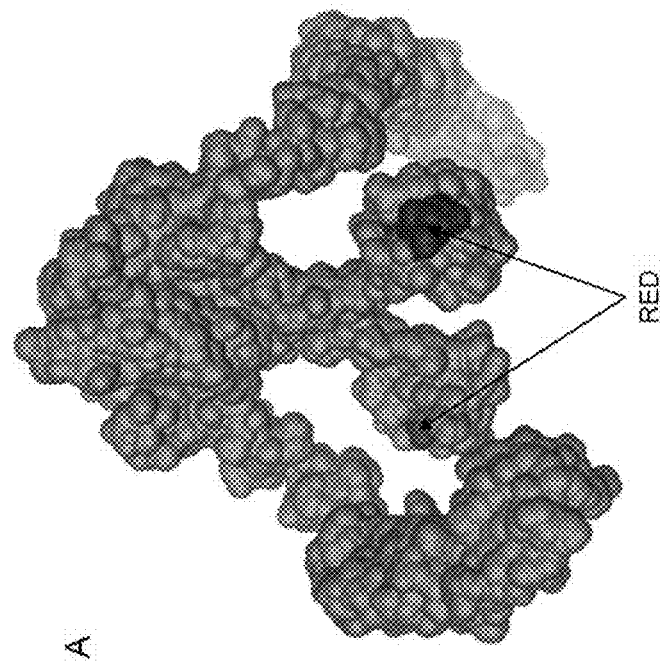
Fig. 5

MULTI-PROTEASE METHOD

TECHNICAL FIELD

The present invention relates to certain new methods to select epitopes of target proteins, utilized for, but not limited to, antibody (e.g. functional antibody) generation. The present invention thus relates in some aspects to a method for generating an antibody. Such methods typically comprise identification of an antigenic epitope and raising an antibody to the antigenic epitope. The invention also relates to antigenic epitopes and antibodies which bind such antigenic epitopes.

BACKGROUND

Antibody therapeutics is growing rapidly much due to the clinical success seen with several monoclonal antibody (mAb) therapies including Humira, Avastin, Herceptin, and the promise of e.g. new cholesterol-lowering mAb treatments targeting PCSK9, such as Alirocumab and Evolocumab. However, all antibodies currently on the market, and all in advanced stage clinical development are generally directed towards extracellular targets, and they are generally discovered and developed using screening platforms focusing on affinity or binding strength. Development of intracellularly acting antibodies, and antibodies directed to "difficult targets", i.e. targets where traditional antibody discovery methodology has failed is, however, a daunting challenge, requiring new technological advancements to discover and develop efficient antibodies. For intracellularly acting antibodies, new tools for internalization of antibodies to cells in the right target organs are also needed. Furthermore, current antibody discovery and development platforms generally lack functional, pharmacological, and mechanism-of-action correlates that can predict the workings of a particular antibody in a given biological system, such as in a medical condition.

Today, strategies towards developing and finding successful antibody therapeutics are not 30 limited to full size monoclonal antibodies. Due to advances in protein engineering, a wide variety of engineered antibody fragments have been derived during the two last decades including Fab fragments, ScFv fragments, diabodies, tetrabodies, antibody fragments functionalized with protein conjugates, as well as bispecific fragments binding to two antigens. These new constructs provide a much larger toolbox when trying to develop 35 antibodies and antibody-derived biologics with high specificity and affinity, deep tissue penetration, high stability and low toxicity. However, one of the main hurdles with antibody therapies still remains and that is their general restriction to extracellular targets. Antibodies are too large and too polar to enter through the cell membrane. Additionally, antibodies are generally unstable in the reducing environment of the cytosol. Several techniques have been developed in order to access intracellular targets, including transport of antibodies across the cell membrane with different transport vectors e.g. transfection reagents and protein transduction domains (PTDs), as well as the expression of the antibody directly within the target cell, so called intrabodies. Electroporation techniques have also been used, although not as extensively for antibodies as small molecules and genetic material. Intrabodies can be constructed to target different cellular compartments by fusing the genetic sequence of the intrabody with intracellular trafficking signals. The need for efficient delivery vectors is nonetheless a crucial step in intrabody therapy since the genetic material encoding the intrabody still needs to be delivered to the target cell.

The production of monoclonal antibodies by the hybridoma technique was first developed in 1975. Briefly, mammals are injected with the antigen of interest, which triggers their immune response. Splenocytes from the animal spleen are then removed and later fused with immortalized myeloma cells. The cells are diluted down to single cells and separated into multi-well plates. Since one cell gives rise to each separate colony, the produced antibodies in a single well will be monoclonal. The next step is to screen all of the different wells for the best candidate for binding to the antigen.

A huge advantage with smaller antibody fragments compared to full size antibodies, is that they can be produced in different expression systems, e.g. *Escherichia coli*, yeast and mammalian cells, and are no longer limited to production with the hybridoma technique. This enables large-scale production at lower cost and many possibilities to genetically modulate antibody properties. Antibody fragments can be displayed on the surface of a filamentous bacteriophage, a so-called phage display, which can be used to create large antibody libraries, which are screened against the desired antigen. The screening procedure evaluates the antibody candidates that bind to the antigen. It is often repeated in several cycles due to unspecific binding in the first cycles. The conditions during the screening cycles can be changed in order to find the best suitable candidates for a certain environment, e.g. more stable antibodies can be selected by using a harsh environment. Another method to select antibodies with very high affinity is to perform the screening with very low concentration of antigen so that only those antibodies capable of binding during such conditions remain. Several companies have developed their own screening technologies, and often have large antibody libraries, see e.g. Regeneron (regeneron.com) or Alligator bioscience (alligatorscience.se).

SUMMARY

In one aspect, the present invention provides a method of generating an antibody to a protein, said method comprising:
(i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and
(ii) raising an antibody against the antigenic epitope.

In another aspect, the present invention provides a method of generating an antibody to a protein, said method comprising:
(i) exposing the protein to limited or restricted proteolysis by contacting the protein with at least one protease to form at least one digested, deconstructed or truncated version of the protein and at least one surface-exposed peptide that is cleaved off from the protein by the action of said protease; and
(ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or selecting at least one target region within the protein based on bioinformatics and/or known data of biological function of the protein and identifying an antigenic epitope by identifying a surface-exposed epitope among the at least one surface-exposed peptide present in said at least one target region; and (iii) raising an antibody against the antigenic epitope.

In another aspect, the present invention provides a method of identifying an antigenic epitope, said method comprising:
(i) exposing a protein to limited or restricted proteolysis by contacting the protein with at least one protease to form at least one digested, deconstructed or truncated version of the protein and at least one surface-exposed peptide that is cleaved off from the protein by the action of said protease; and
(ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or
selecting at least one target region within the protein based on bioinformatics and/or known data of biological function of the protein and identifying an antigenic epitope by identifying a surface-exposed epitope among the at least one surface-exposed peptide present in said at least one target region.

The present invention relates to methods of detecting and identifying amino acid sequences in proteins where said amino acid sequences are well-exposed, and functionally relevant, at least they are well-exposed. These amino acid sequences which we refer to as "hot spots", thus, may be utilized as antigenic epitopes that guides antibody targeting, discovery, and development. Furthermore, these amino acid sequences can be ranked based on their appearance after proteolytic digestion, and based on functional relevance from already known bioinformatic data or from functional/pharmacological testing. Thus, from a list of several amino acid sequences resulting from a proteolytic digestion, the best suited amino acid sequences (based on functional and structural arguments) can be picked for antigenic epitope discovery and development. The proteolytic digestion is performed under limiting conditions, i.e. the activity of the protease or several proteases is very low such that just one or a few surface-exposed peptides are cleaved off from the target protein at a time. The proteases are thus used as druggability probes for antibody binding to a target protein.

In an embodiment, the antibodies are pharmacologically active. In another embodiment, the antibodies are pharmacologically active and developed for therapeutic usage. More specifically, such methods include proteomic tools to reveal hot spot epitopes of target proteins.

In an aspect of the invention, a protein is digested, deconstructed and/or truncated through protease action and all well-exposed amino acid sequences are used for antigenic epitope generation, and antibodies developed based on said antigenic epitopes are tried for potency, efficacy, pharmacological profiling, and other testing as customary in antibody discovery used in the pharmaceutical industry.

In an aspect of the invention, a protein is digested, deconstructed and/or truncated through protease action and in parallel probed by a functional assay on the digested, deconstructed and/or truncated protein to delineate functionally important regions of the protein. The relevant protein is sometimes denoted target protein herein.

In an embodiment, the digestion, deconstruction and/or truncation of the target protein is performed in parallel by a functional assay to delineate functionally important regions of the target protein to guide epitope selection for antibody generation.

In an embodiment, the digestion, deconstruction and/or truncation, and functional assay of digested, deconstructed and/or truncated protein and native target protein are combined with other bioinformatic and otherwise known facts about protein function to delineate functionally important regions of the target protein to guide epitope selection for antibody generation.

In an embodiment, a single protease may be used to digest, deconstruct and/or truncate the target protein. In another embodiment, multiple proteases may be used to digest, deconstruct and/or truncate the target protein, sequentially one at a time or in parallel. Such proteases are exemplified but not limited to Arg-C proteinase, Asp-N endopeptidase, Clostripain, Glutamyl endopeptidase, Lys-C, Lys-N, Trypsin, Chymotrypsin, Proteinase K and Thermolysin. A region that is easily digested by several proteases should be located in an exposed region of the protein and a region that is only digested by a single protease is probably located in a more hidden region. Alternatively, the protease has unique cleaving specificity or/and physicochemical properties or/and structural features such that it can identify surface-exposed peptides on a target protein that other proteases cannot. Thus, the usage of multiple proteases is preferable, and each different protease can yield complementary or unique information about surface-exposed peptides suitability as antigenic epitopes.

The embodiments enable new methodology/technology for rapid and precise development of pharmacologically active antibodies that can be used for pharmacological studies, e.g. they can be used as a tool for detecting biological compounds in e.g. cell or in vitro assays. More importantly, said antibodies may be used to treat a medical condition in humans and animals. The embodiments can be applied to all proteins, soluble or membrane bound, extracellular or intracellular. The embodiments can furthermore be exploited to yield new fundamental understanding of protein function.

The present invention also provides an antibody generated by a method of the present invention.

The present invention also provides an antigenic epitope identified by a method of the present invention.

The present invention also provides an antibody against an antigenic epitope of the present invention.

Other features and advantages of the invention will be apparent from the following detailed description.

BRIEF DESCRIPTION OF THE DRAWINGS

The embodiments, together with further objects and advantages thereof, may best be understood by making reference to the following description taken together with the accompanying drawings, in which.

Figure 1:
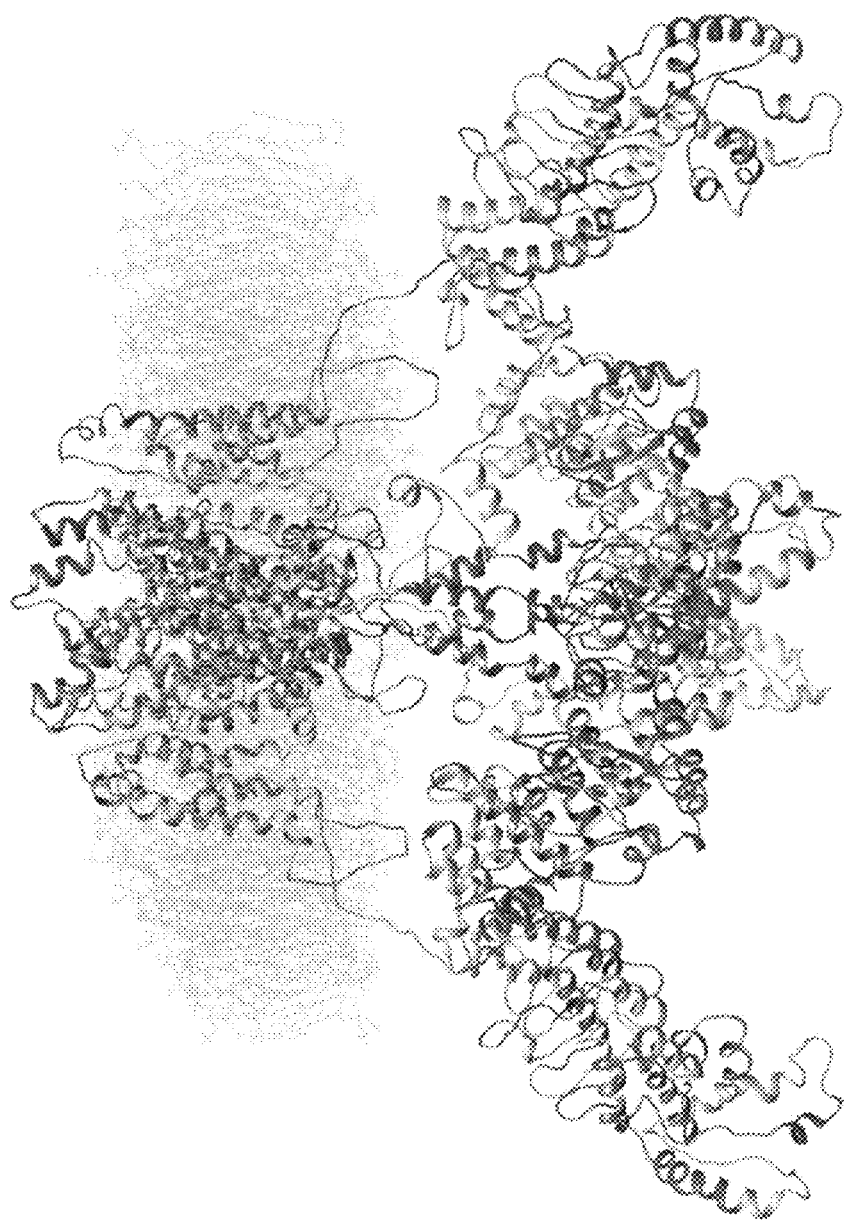
FIG. 1
Figure 1:
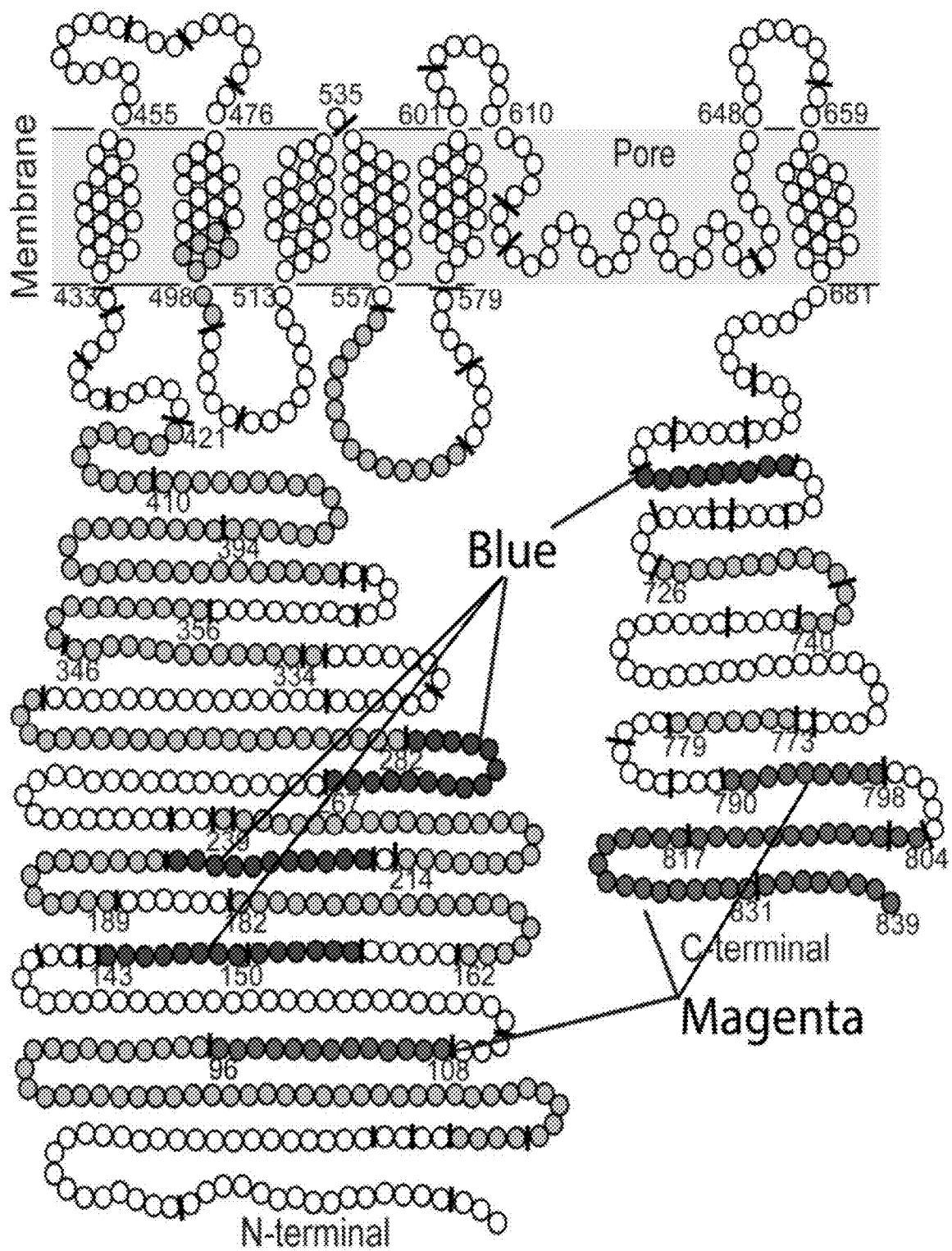
Figure 1:
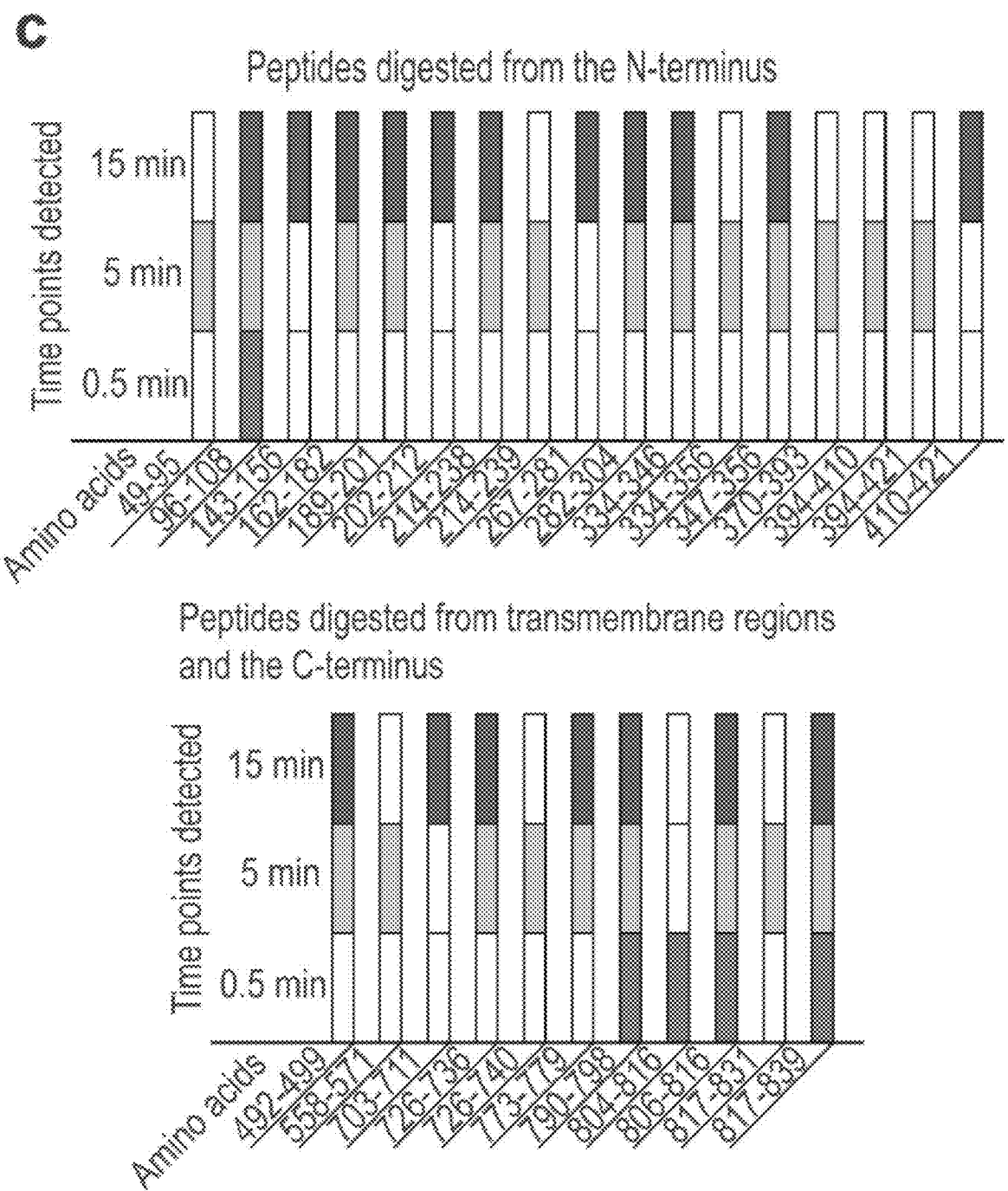

Peptides detected from TRPV1 after limited proteolysis with 5 µg/ml trypsin at room temperature, n=6. A: Location of detected peptides shown in a 3D-model of TRPV1. Peptides were detected after 0.5 min (magenta), 5 min (orange), and 15 min (blue) B: Location of detected peptides shown in a schematic representation of TRPV1. Peptides were detected after 0.5 min (magenta), 5 min (orange), and 15 min (blue). C: Bar plot of detected peptides digested from TRPV1 after limited proteolysis with 5 µg/ml trypsin, showing at which time points they were confirmed.

FIG. 2

Peptides digested from TRPV1 after 5 min exposure to 5 µg/ml, 20 µg/ml or 40 µg/ml trypsin (Tr) and the change in current response after their removal. A-C: Location of digested peptides from TRPV1, showing peptides digested within the flow cell (cyan) and peptides digested within the flow cell followed by a complete digestion overnight (yellow). D: Representative traces of inside-out recordings of TRPV1 when activated with 1 µM capsaicin (Cap), followed by 5 min exposure to either buffer or trypsin and an additional activation with capsaicin. From top to bottom: 5 min exposure to buffer, 5 µg/ml, 20 µg/ml and 40 µg/ml trypsin respectively. Traces have been digitally filtered at 100 Hz for figure presentation purposes only.

FIG. 3

Electrophysiological patch clamp recordings of TRPV1 function showing the current trace time integral for the second activation with capsaicin, calculated as a percentage of the integral for the first activation with capsaicin after treatment with either buffer n=11, or antibody n=6. Data is presented as mean±SEM.

FIG. 4

Location of the antigen determinant (red) for OTV1, peptide aa96-117, visualized in a surface model of hTRPV1. A: Side view of TRPV1 where each monomer is colored in alternating blue and purple. B: Top view of TRPV1 where each monomer is colored in alternating blue and purple.

FIG. 5

Location of the antigen determinant (red) for OTV2, peptide aa785-799, visualized in a surface model of hTRPV1. A: Side view of TRPV1 where two monomers have been omitted for viewing purposes. B: Bottom view of TRPV1 where each monomer is colored in alternating blue and purple.

FIG. 6

Localization of OTV1 (left) and OTV2 (right) in fixed cells with (A) and without (B) the expression of TRPV1. OTV1 and OTV2 were visualized using a goat anti-rabbit Alexa 488 secondary antibody. The intensity values along a line segment (black) crossing a cell is given beneath each image. Different laser settings were used for OTV1 and OTV2 and comparisons between the antibodies shouldn't be made.

FIG. 7

Electrophysiological patch clamp recordings of TRPV1 function after treatment with antibody. A: the current trace time-integral for the second activation with capsaicin, calculated as a percentage of the integral for the first activation with capsaicin, after treatment with either buffer (n=11) or OTV1 (n=6). B: The current trace time-integral for the second activation with capsaicin in the presence of calmodulin (CaM) and OTV2, calculated as a percentage of the integral for the first activation with capsaicin, after treatment with either only calmodulin (n=11) or calmodulin and OTV2. Treatment with OTV2 is separated into measurements within 15 minutes of tip-sonication (n=4) and measurements within 30 minutes of tip-sonication (n=7). Data is presented as mean±SEM.

FIG. 8

A: TRPV1 mediated YO-PRO uptake after electroporation with OTV1 in calcium free PBS. Top: Fluorescence intensity for OTV1 (n=11) and control (n=11). Bottom: Corresponding fluorescence intensity rate for OTV1 and control. B: TRPV1 mediated YO-PRO uptake after electroporation with OTV2 in the presence of 50 µM $Ca^{2+}$. Top: Fluorescence intensity for OTV2 (n=9) and control (n=7). Bottom: Corresponding fluorescence intensity rate for OTV2 (green) and control (red). Data is presented as mean±SEM.

FIG. 9

Validation of internalization of antibodies through electroporation, with fluorescence. Cells were electroporated, fixed, permeabilized and incubated with a goat antirabbit Alexa 488 secondary antibody. Fluorescence intensities were measured with confocal microscopy. Intensities are compared between electroporated and non-electroporated cells subjected to either OTV1 or OTV2, as well as cells only subjected to the secondary antibody. Different laser setting were used between OTV1 and OTV2 and comparisons in intensity values shouldn't be made. Data is presented as mean±SEM.

FIG. 10

Peptides detected from TRPV1 after limited proteolysis with trypsin. Location of detected peptides shown in a 3D-model of TRPV1. Experimental details are given in Example 3. Peptides digested first are shown in black. Peptides digested late are shown in grey.

FIG. 11

Peptides detected from TRPV1 after limited proteolysis with Asp-N. Location of detected peptides shown in a 3D-model of TRPV1. Experimental details are given in Example 3. Peptides digested first are shown in black. Peptides digested late are shown in grey.

FIG. 12

Peptides detected from TRPV1 after limited proteolysis with Chymotrypsin. Location of detected peptides shown in a 3D-model of TRPV1. Experimental details are given in Example 3. Peptides digested first are shown in black. Peptides digested late are shown in grey.

FIG. 13

Peptides detected from TRPV1 after limited proteolysis with pepsin. Location of detected peptides shown in a 3D-model of TRPV1. Experimental details are given in Example 3. Peptides digested first are shown in black. Peptides digested late are shown in grey.

FIG. 14

Peptides detected from TRPV1 after limited proteolysis with Proteinase K. Location of detected peptides shown in a 3D-model of TRPV1. Experimental details are given in Example 3. Peptides digested first are shown in black. Peptides digested late are shown in grey.

FIG. 15.

This Figure shows (d) a suitable to investigate the missed cut sites, antibodies are produced against 7-8 amino acid-long sequences containing missed cut sites, using a frame shift approach (using a nested set of epitopes) in order to cover a suitable region (e.g. from −20 to +20 amino acids surrounding a cut site). The antibodies are screened to find the best binders.

DETAILED DESCRIPTION

The foregoing and other aspects of the present invention will now be described in more detail with respect to the description and methodologies provided herein. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

The terminology used in the description of the invention herein is for the purpose of describing particular embodiments only and is not intended to be limiting of the invention. As used in the description of the embodiments of the invention, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. When a range is employed (e.g. a range from x to y) it is it meant that the measurable value is a range from about x to about y, or any range therein, such as about x1 to about y1, etc. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

In one aspect, the present invention provides a method of generating an antibody to a protein, said method comprising:
 (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and
 (ii) raising an antibody against the antigenic epitope.

In another aspect, the present invention provides a method of generating an antibody to a protein, said method comprising:
 (i) exposing the protein to limited or restricted proteolysis by contacting the protein with at least one protease to form at least one digested, deconstructed or truncated version of the protein and at least one surface-exposed peptide that is cleaved off from the protein by the action of said protease; and
 (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or selecting at least one target region within the protein based on bioinformatics and/or known data of biological function of the protein and identifying an antigenic epitope by identifying a surface-exposed epitope among the at least one surface-exposed peptide present in said at least one target region; and
 (iii) raising an antibody against the antigenic epitope.

Alternatively viewed, the present invention provides a method of generating an antibody to a protein, said method comprising:
 (i) exposing the protein to limited or restricted proteolysis by contacting the protein with at least one protease to form at least one digested, deconstructed or truncated version of the protein and at least one surface exposed peptide that is cleaved off from the protein by the action of said protease; and
 (ii) identifying an antigenic epitope by identifying a surface-exposed peptide that is cleaved off that has an amino acid sequence that is, or that is predicted to be, of functional importance to said protein, and generating an antigenic epitope based on said surface-exposed peptide; and
 (iii) raising an antibody against said antigenic epitope.

In another aspect, the invention provides a method of generating an antibody to a protein, said method comprising:
 (i) identifying a surface-exposed peptide in said protein by exposing the protein to limited or restricted proteolysis by contacting the protein with at least one protease to form at least one digested, deconstructed or truncated version of the protein and at least one peptide that is cleaved off from the protein by the action of said protease; and
 (ii) constructing a linear or conformational antigenic epitope based on the at least one surface-exposed peptide; and
 (iii) raising an antibody against the antigenic epitope.

In another aspect, the invention provides a method of generating an antibody to a protein, said method comprising:
 (i) identifying a surface-exposed peptide in said protein by exposing the protein to limited or restricted proteolysis by contacting the protein with at least one protease to form at least one digested, deconstructed or truncated version of the protein and at least one surface-exposed peptide that is cleaved off from the protein by the action of said protease; and
 (ii) identifying a surface-exposed peptide that when cleaved off or removed from the protein during the limited or restricted proteolysis, results in a lack of, or significantly altered, biological function of said protein; or selecting at least one of the identified surface-exposed peptides of (i) based on correlation of said surface-exposed peptides with bioinformatics and/or known data of biological function of the protein; and
 (iii) constructing a linear or conformational antigenic epitope based on the at least one surface-exposed peptide; and
 (iv) raising an antibody against the antigenic epitope.

In another aspect, the present invention provides a method of generating an antibody to a protein, said method comprising:
 (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease; and (ii) raising an antibody against the antigenic epitope.

A method of generating an antibody in accordance with the present invention may, in another aspect, be alternatively viewed as a method for the production of an antibody that specifically binds to a protein. Exemplary and preferred embodiments of methods of generating an antibody described herein also apply, mutatis mutandis, to methods for the production of an antibody that specifically binds to a protein.

In another aspect, the present invention provides a method of identifying an antigenic epitope, said method comprising:

(i) exposing a protein to limited or restricted proteolysis by contacting the protein with at least one protease to form at least one digested, deconstructed or truncated version of the protein and at least one surface-exposed peptide that is cleaved off from the protein by the action of said protease; and (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or selecting at least one target region within the protein based on bioinformatics and/or known data of biological function of the protein and identifying an antigenic epitope by identifying a surface-exposed epitope among the at least one surface-exposed peptide present in said at least one target region.

Optionally, this method further comprises a step of raising an antibody against said antigenic epitope.

Alternatively viewed, the present invention provides a method of identifying an antigenic epitope, said method comprising:

(i) exposing a protein to limited or restricted proteolysis by contacting the protein with at least one protease to form at least one digested, deconstructed or truncated version of the protein and at least one surface-exposed peptide that is cleaved off from the protein by the action of said protease; and (ii) identifying an antigenic epitope by identifying a surface-exposed peptide that is cleaved off that has an amino acid sequence that is, or that is predicted to be, of functional importance to said protein, and generating an antigenic epitope based on said surface-exposed peptide.

Optionally, this method further comprises a step of raising an antibody against said antigenic epitope.

Detailed knowledge about surface-exposed functionally active epitopes within a protein could aid the development of efficient antibodies and decrease the need for elaborate screening procedures by lowering the amount of antibody candidates. A possible method to evaluate surface topology of a protein is to restrict the activity of a protease to digest only the most flexible and surface-exposed parts of the protein, by performing limited and controlled proteolysis. The idea is to slow down the kinetics of protease activity so much that peptides are cleaved off one at the time, or at most a few at the time. The cleaved off peptides can then be ranked based on order of appearance after a protease challenge. The peptides that are cleaved off the protein first are well exposed by the protein, and can be easily accessed by the protease. We give these peptides a high rank, and we hypothesize that peptides easily cleaved off by a protease are also easily recognized by an antibody. The peptides that are cleaved off late we give a low rank, and all peptides in between are given from high to low scores based on appearance in time after a protease challenge. Thus, the method is amino acid sequence based, and since we know the sequence we know specifically where the antibody will bind to said target protein. In a second step, as we know the specific amino acid sequences that are targeted in a protein, we can investigate from published data or other known bioinformatic data or from pharmacological studies of truncated proteins the functional significance of said amino acid sequence. If the amino acid sequence coincides or touches or overlaps with a known amino acid sequence having functional importance, eg binding site, modulatory site, structurally important site, channel region etcetera, then said peptide is given a high score and judged a good candidate for antigenic epitope and subsequent antibody development. This can be achieved, specifically, by controlling the activity of a protease using e.g. low temperatures, low concentrations and/or short digestion times. When limited proteolysis have been performed on proteins with known structure, mainly three structural determinants have been recognized as having impact on where the proteolytic activity occurs. These include flexibility, surface exposure and the number of local interactions. In order for the peptide chain to enter the active site within the protease, flexibility and the ability of the protein to locally unfold is required. Surface exposure renders a cleavage site more likely for proteolysis, due to the fact that regions at the surface tend to more easily unfold as well as impose less steric hindrance. The amount of local interactions in the term of hydrogen bonds and disulphide bridges is also important. Less local interactions favor proteolysis. All three of these structural determinants are usually correlated within the protein. Hence, limited proteolysis will mainly cleave surface exposed regions given that the protein chain can unfold locally. It has been used as a method to determine surface exposed regions in proteins with unknown detailed structure.

The lipid-based protein immobilization (LPI) technology enables flexible chemistry to be performed on membrane proteins. By deriving proteoliposomes from cells and immobilize them within the flow cell, a stationary phase of membrane proteins is created, which can be subjected to several rounds of solutions and different types of chemical modulations, e.g. by enzymes. A sequential tryptic digestion protocol for proteomic characterization has been developed, where the peptides resulting from stepwise enzymatic digestion of the proteoliposomes are analyzed with liquid chromatography with tandem mass spectrometry (LC-MS/MS) [1-3].

In some embodiments of methods of the present invention, the protein is a protein (e.g. a membrane protein) that is present in (e.g. in the lipid bilayer of) a proteoliposome (e.g. in a proteoliposome derived from cells for example human cells). Accordingly, in some embodiments, limited proteolysis is performed on proteoliposomes. Proteoliposomes are lipid vesicles comprising proteins. Proteoliposomes can be reconstituted from purified membrane proteins and lipids or can be directly derived from the cell membrane (e.g. through blebbing) or through lysis of the cell. Preferably, proteoliposomes are derived from (prepared from) cell membranes of lysed cells. Proteoliposomes may be obtained from any cell type of interest. A convenient cell type is Chinese hamster ovary (CHO) cells.

Methods of preparing proteoliposomes are known in the art and any of these may be used (e.g. the method described in Jansson et al. *Anal. Chem.*, 2012, 84:5582-5588). An exemplary and preferred method for preparing proteoliposomes is described in the Examples herein. Typically, proteoliposomes having a diameter of about 50 nm to about 150 nm are preferred.

Using proteoliposomes derived from (prepared from) cell membranes of lysed cells is preferred as proteoliposomes prepared in such a manner (e.g. using a method referred to in the Examples) may present intracellular portions (or domains) of membrane proteins on the exterior of the proteoliposome, thus making available for proteolytic cleavage (and thus antigenic epitope identification) some parts of the protein that would be otherwise inaccessible to a protease.

In one aspect, we have developed a targeted antibody technology by utilizing the LPI microfluidic platform [1, 4] to generate potential epitope candidates. This is a mechanism-, rather than screening-, based methodology. Briefly, the LPI technology, enables flexible chemistry, such as limited proteolysis, to be performed on membrane proteins. By deriving proteoliposomes from cells and immobilize them within the flow cell, a stationary phase of membrane proteins is created. A sequential digestion protocol for proteomic characterization has been developed, where the peptides resulting from stepwise enzymatic digestion of the proteoliposomes are analyzed with LC-MS/MS. Such peptides, generated from a kinetically controlled digestion within the LPI flow cell, elucidates exposed and accessible regions within the target protein, regions that have the potential of being accessible to antibody binding. These potential epitopes are further correlated against known functional data, in order to find epitopes that will yield antibodies with both excellent binding characteristics and biological efficacy. Finally, the chosen epitopes/peptides may be used to immunize a host animal in order to produce antibodies. It should be mentioned that other methods and techniques to perform limited proteolytic digestion are known in the art, and might be used eg for soluble proteins.

In some embodiments of the present invention, the protein (e.g. a membrane protein) is immobilized (e.g. on a solid support) prior to limited or restricted proteolysis to create a stationary phase of the protein. Thus, in some embodiments the protein is surface-bound.

In some embodiments, the protein (e.g. membrane protein) is present in (or is presented on) a proteoliposome (e.g. a proteoliposome derived from cells) and said proteoliposome is immobilized (e.g. on a solid support) prior to limited or restricted proteolysis to create a stationary phase of the protein.

In some embodiments of methods of the present invention, the protein is a membrane protein that is present in a proteoliposome derived from cells, wherein said proteoliposome is immobilized in a flow cell to create a stationary phase of membrane proteins. Suitable flow cells are known in the art, for example, the flow cell described by Jansson et al. (*Anal. Chem.*, 2012, 84:5582-5588).

In some embodiments, the protein (e.g. membrane protein) is present in (or is presented on) a proteoliposome (e.g. a proteoliposome derived from cells) and said proteoliposome is in a suspension (e.g. suspended in a solution).

In some embodiments, said protein is in (or presented on) a protein-containing lipid vesicle that is surface-bound or in a suspension (e.g. suspended in a solution).

In some embodiments, said protein may be part of, or presented on, any appropriate entity such that its functional or natural conformation is preserved, e.g. part of a lipid bilayer or membrane or on a scaffold or particle.

In some embodiments, said protein is in (or presented on) a particle, such as a nanoparticle, or any other colloidal particle that is surface-bound or in a suspension (e.g. suspended in a solution).

In some embodiments, said protein is in (or presented on) a scaffold or other chemical entity such as a caging compound, that is surface-bound or in a suspension (e.g. suspended in a solution).

In some embodiments, said protein is in (or is presented on) an intact cell (biological cell e.g. human cell) that is surface-bound or in a suspension (e.g. suspended in a solution).

"In" in the context proteins in proteoliposomes, protein containing vesicles or intact cells 30 includes proteins that extend to (and thus are exposed to) the exterior of the proteoliposome, protein containing lipid vesicle or cell.

In some embodiments, said protein is in a solution. The solution may be a solution of purified protein or may contain a mixture of proteins.

In some embodiments, cells (e.g. CHO cells) overexpress the protein, for example via a regulatable (e.g. Tetracycline regulatable) expression system. In some embodiments, proteoliposomes derived from such cells are used.

We examined peptides generated from limited proteolysis of the transient receptor potential vanilloid 1 (TRPV1) ion channel with the purpose of finding potential epitopes for development of biologically active antibodies that have the capability of modulating the function of this ion channel. TRPV1 was subjected to limited proteolysis with two different proteases and the digested peptides were correlated with functional data. We have, using this information, developed two polyclonal antibodies, OTV1 and OTV2, acting on the intracellular side of the human TRPV1 (hTRPV1) ion channel. Both antibodies are pharmacologically active and their targeted epitope regions were chosen based on their ease of digestion (or surface exposure (highly ranked peptides after limited proteolysis)) as well as functional importance. OTV1 displays strong inhibitory action on the protein when stimulated with the agonist capsaicin. OTV2 interferes with calmodulin/$Ca^{2+}$ dependent desensitization of TRPV1, which is a process that is triggered by calcium influx through TRPV1. The efficacy of OTV1 and OTV2 was studied both with inside-out patch clamp, where the intracellular side of TRPV1 could be exposed to antibody solution and with a TRPV1-mediated fluorescence uptake assay after the antibodies were electroporated inside living cells.

Methods that use the LPI flow cell in combination with an open-volume microfluidic flow cell for fast solution exchange suitable for patch clamp experiments has previously been described. The beauty of this is that cell membranes can be turned inside out, and intracellular domains of an ion channel can be interrogated directly. In this approach one can obtain correlated structural and functional data using limited and controlled proteolysis. TRPV1 is a cation channel, which is expressed in nociceptive primary sensory neurons. A detailed crystal structure is not available for the full-length protein, but the ankyrin repeat domain (ARD) of the N-terminus has successfully been crystallized for rat TRPV1. Peptides digested at short time scales when performing limited proteolysis on TRPV1 has been compared to known functionally active regions. A third of the detected peptides contained residues that have been proposed to be functionally important.

A screening of TRPV1 surface topology as described in the survey of the field was performed by immobilizing proteoliposomes containing TRPV1 within the flow cell and further expose them to limited trypsin proteolysis [1, 4]. The activity of trypsin was controlled by using different digestion times at room temperature. A sequential protocol was used with cumulative incubation times and the digested peptides were detected with LC-MS/MS. An increasing number of peptides were detected with time, highlighting regions of the proteins that were accessible and easily digested, as well more rigid regions. This is illustrated in FIG. 1. Several of the regions that were observed with LC-MS/MS as cleaved-off peptides after limited proteolysis of TRPV1 in the LPI flow cell correlate with known interaction sites for calmodulin, ATP and PIP2.

Figure 2:
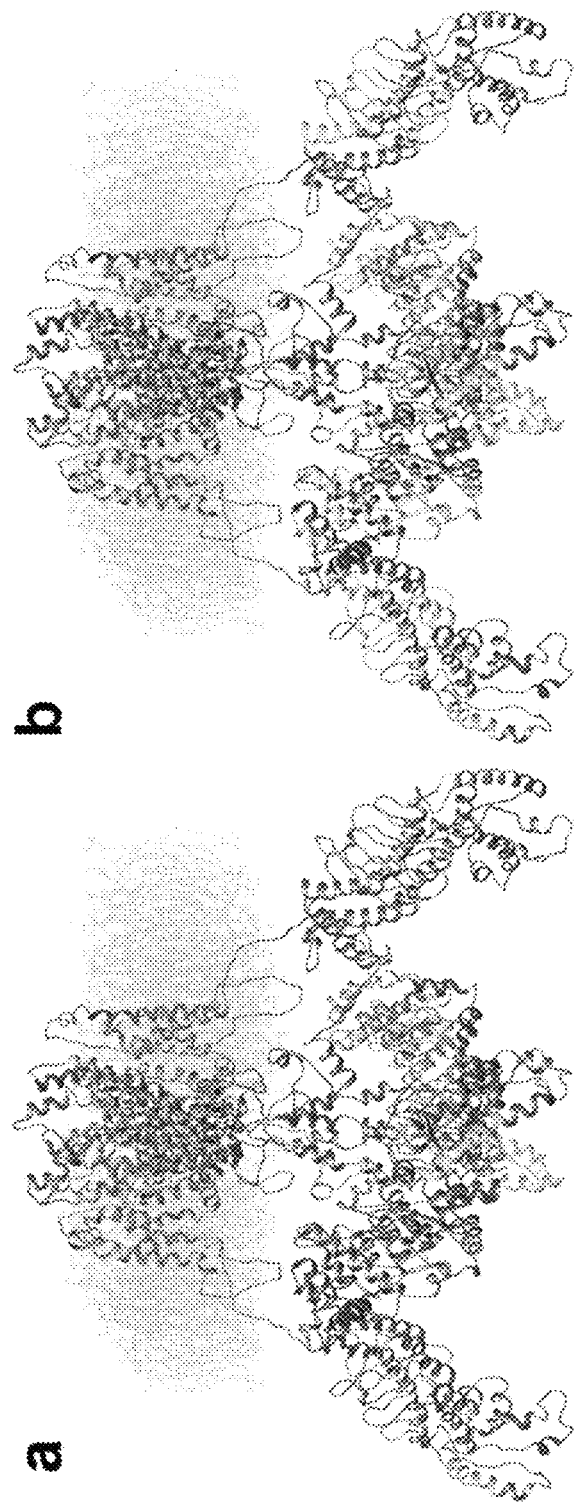
Figure 2:
Figure 2:
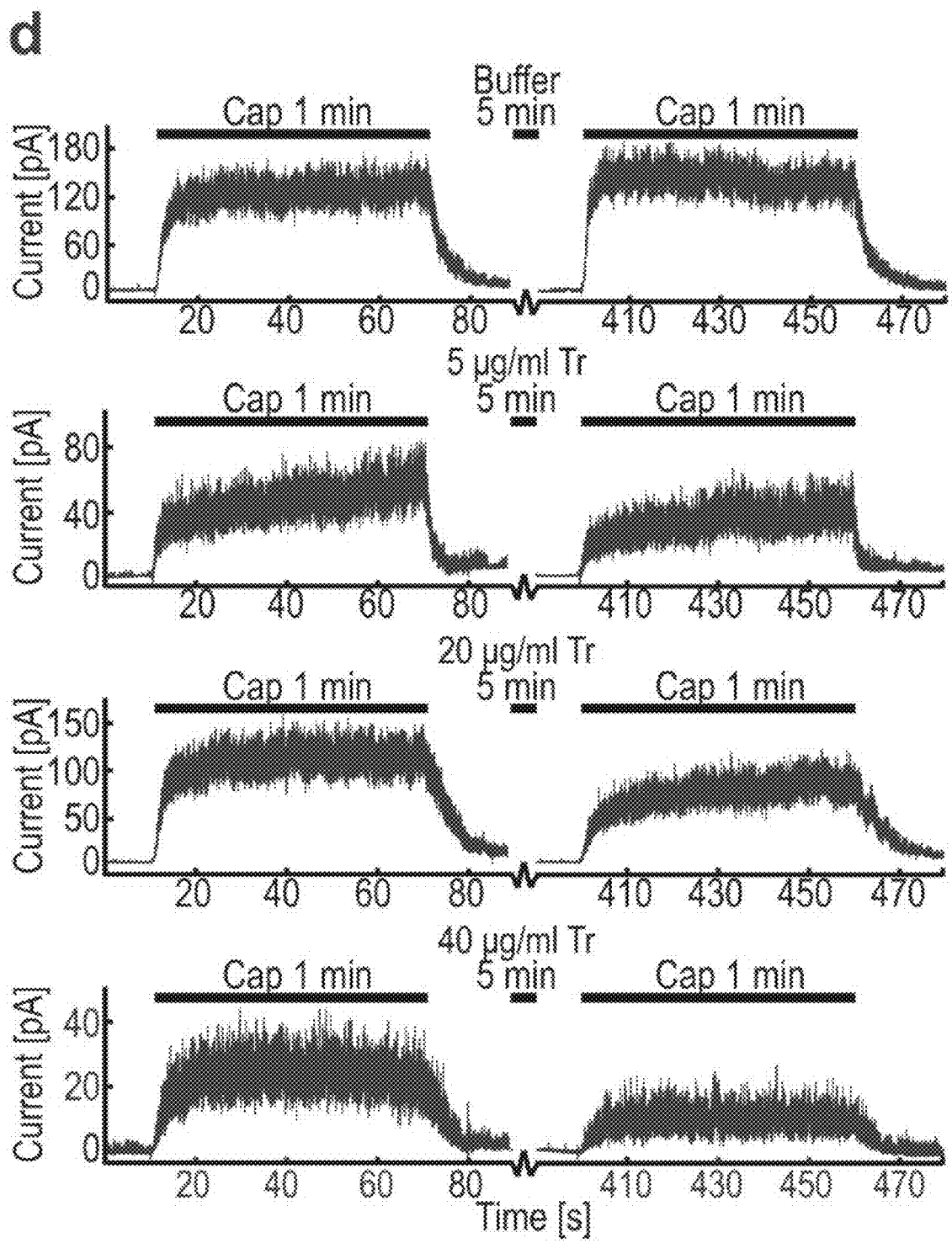

We have also tested the functionality of TRPV1 after removal of different structural segments with tryptic digestion [4]. The activity of the TRPV1 ion channel was tested with inside-out patch-clamp recordings and flow cell digestions followed by proteomic analysis evaluated the structural effects of chemical truncation. We have used the inside-out patch-clamp recording configuration, allowing the intracellular part of TRPV1 to be exposed to trypsin and determined a decrease in current response with increasing trypsin concentration (FIG. 2).

We demonstrate that the ion channel TRPV1 can be exposed to limited and controlled trypsin proteolysis in two different microfluidic flow cells under identical experimental conditions. In one instance, patch-clamp recording was performed for pharmacological studies, which obtained information on channel function dynamics in an open-volume microfluidic device. This design allows the patch-clamp pipette and cell patch to gain access to the superfusion channels. In another instance, a closed-volume equivalent flow cell was used to digest off peptides from the ion channel without causing dilution of the sample. The cleaved-off peptides were identified with LC-MS/MS. The data from the two experiments were then compared and the structure-function relationship could be evaluated. Using this methodological approach we have identified highly flexible regions of TRPV1 as well as key regions that affect functional channel properties during activation with its agonist capsaicin.

This type of methodology can also be used for other proteins (i.e. non-TRPV1 proteins).

The amino acid sequence of hTRPV1 is presented below (SEQ ID NO:1).

```
MKKWSSTDLGAAADPLQKDTCPDPLDGDPNSRPPPAKPQLSTAKSRT

RLFGKGDSEEAFPVDCPHEEGELDSCPTITVSPVITIQRPGDGPTGA

RLLSQDSVAASTEKTLRLYDRRSIFEAVAQNNCQDLESLLLFLQKSK

KHLTDNEFKDPETGKTCLLKAMLNLHDGQNTTIPLLLEIARQTDSLK

ELVNASYTDSYYKGQTALHIAIERRNMALVTLLVENGADVQAAAHGD

FFKKTKGRPGFYFGELPLSLAACTNQLGIVKFLLQNSWQTADISARD

SVGNTVLHALVEVADNTADNTKFVTSMYNEILMLGAKLHPTLKLEEL

TNKKGMTPLALAAGTGKIGVLAYILQREIQEPECRHLSRKFTEWAYG

PVHSSLYDLSCIDTCEKNSVLEVIAYSSSETPNRHDMLLVEPLNRLL

QDKWDRFVKRIFYFNFLVYCLYMIIFTMAAYYRPVDGLPPFKMEKTG

DYFRVTGEILSVLGGVYFFFRGIQYFLQRRPSMKTLFVDSYSEMLFF

LQSLFMLATVVLYFSHLKEYVASMVFSLALGWTNMLYYTRGFQQMGI

YAVMIEKMILRDLCRFMFVYIVFLFGFSTAVVTLIEDGKNDSLPSES

-continued
TSHRWRGPACRPPDSSYNSLYSTCLELFKFTIGMGDLEFTENYDFKA

VFIILLLAYVILTYILLLNMLIALMGETVNKIAQESKNIWKLQRAIT

ILDTEKSFLKCMRKAFRSGKLLQVGYTPDGKDDYRWCFRVDEVNWTT

WNTNVGIINEDPGNCEGVKRTLSFSLRSSRVSGRHWKNFALVPLLRE

ASARDRQSAQPEEVYLRQFSGSLKPEDAEVFKSPAASGEK
```

The present invention therefore enables functional studies of specific epitopes, or evaluation of putative binding sites for novel antibodies, for a target membrane protein residing in its native lipid environment.

In accordance with the present invention, an antigenic epitope is typically based on a surface-exposed peptide that has been cleaved off from a protein during limited or restricted proteolysis. Alternatively viewed, a surface-exposed peptide is typically used to generate an antigenic epitope.

In this regard, an antigenic epitope may comprise the amino acid sequence of the surface-exposed peptide or a sequence substantially homologous thereto. The antigenic epitope may consist of the amino acid sequence of the surface-exposed peptide or a sequence substantially homologous thereto. The antigenic epitope may overlap with the amino acid sequence of the surface-exposed peptide or a sequence substantially homologous thereto.

Amino acid sequences that are "substantially homologous" to surface-exposed peptides include sequences having, or sequences comprising a sequence that has, 1, 2, or 3 amino acid substitutions (preferably 1 or 2, more preferably 1) compared with the amino acid sequence of the given surface-exposed peptide.

Amino acid sequences that are "substantially homologous" to surface-exposed peptides include sequences that comprise (or consist of) at least 5 or at least 6 consecutive amino acids of the surface-exposed peptides (or comprise or consist of at least 7, at least 8, at least 9, at least 10, at least 11, at least 12, at least 15, at least 20 or at least 25) consecutive amino acids of the surface-exposed peptide). Six amino acids is a typical length of peptide/protein sequence that is recognized or bound by an antibody.

Amino acid sequences that are "substantially homologous" to surface-exposed peptides include sequences having, or sequences comprising a sequence that has, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 98% sequence identity to the given surface-exposed peptide sequence. Sequence identities of at least 70%, at least 75%, at least 80%, at least 85%, at least 90%, at least 95%, or at least 98% are preferred.

An antigenic epitope may comprise (or consist of) an elongated version of a surface-exposed peptide, or an elongated version of an amino acid sequence substantially homologous to the surface-exposed peptide. For example, one or more additional amino acids (e.g. at least 2, at least 3, at least 4, at least 5, at least 6, at least 7, at least 8 or at least 9, at least 10, at least 15 or at least 20 amino acids) may be present at one end or both ends of the surface-exposed peptide sequence (or sequence substantially homologous thereto). In some embodiments, up to 2, up to 3, up to 4, up to 5, up to 6, up to 7, up to 8, up to 9, up to 10, up to 15 or up to 20 amino acids may be present at one end or both ends of the surface-exposed peptide sequence (or sequence substantially homologous thereto).

An antigenic epitope may comprise (or consist of) a truncated version of a surface-exposed peptide, or a truncated version of an amino acid sequence substantially homologous to the surface-exposed peptide. For example, one or more amino acids (e.g. at least 2, at least 3, at least 4, at least 5, at least 6, at least 7, at least 8 or at 9, at least 10) may be absent from one end or both ends of the surface-exposed peptide sequence (or sequence substantially homologous thereto). In some embodiments, up to 2, up to 3, up to 4, up to 5, up to 6, up to 7, up to 8, up to 9 or up to 10, up to 15 or up to 20 amino acids may be absent from one end or both ends of the surface-exposed peptide sequence (or sequence substantially homologous thereto).

An antigenic epitope may be a cyclic peptide, e.g. substantially homologous to one or several surface-exposed peptides where the surface-exposed peptides are positioned close to each other in space.

Antigenic epitopes may be at least 5, or at least 6 or at least 7 amino acids in length, for example 6 to 10, 6 to 12, 6 to 15, 6 to 20, 6 to 25, 6 to 30, 6 to 40, 6 to 50, 6 to 60, or 6 to 75 amino acids in length. Antigenic epitopes may be, for example, up to 7, up to 8, up to 9, up to 10, up to 15, up to 20, up to 25, up to 30, up to 35 or up to 40 amino acids in length. Antigenic epitopes may be, for example, 5 to 30, 6 to 30, 7 to 30, 5 to 25, 6 to 25, or 7 to 25 amino acids in length. Antigenic epitopes may be, for example, 5 to 7 or 5 to 8 or 5 to 9 (e.g. 7 to 9 amino acids) in length. For the avoidance of doubt, longer proteins or polypeptides, e.g. those greater than 100 amino acids in length, are not considered to be epitopes in accordance with the present invention.

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA*, 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, CABIOS, 4:11-17, 1988), FASTA (Pearson and Lipman, *Proc. Natl. Acad. Sci. USA*, 85:2444-2448, 1988; Pearson, *Methods in Enzymology*, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose.

Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

Antigenic epitopes in accordance with the present invention may be linear epitopes or conformational epitopes.

In some embodiments, antigenic epitopes in accordance with the present invention may be cyclized epitopes.

A common technique used for preparing linear antigenic epitopes used for immunization is Fmoc SPPS (Solid Phase Peptide Synthesis). In SPPS, small porous beads are treated with functional linkers on which peptide chains can be built using repeated cycles of wash-coupling-wash. The synthesized peptide is then released from the beads using chemical cleavage. For synthesis of cyclic peptides, common methods utilize cyclization by formation of a disulphide bridge (where the bridge is formed bridge by two cysteines), or by formation of a "head-to-tail" bridge where the bridge consists of a typical peptide bond. Cyclic peptides can be formed on a solid support. Antibodies against conformational epitopes are commonly raised using the entire protein or larger parts of the protein.

Limited or restricted proteolysis includes proteolytic digestion of a protein that does not go to completion. Thus, via limited or restricted proteolysis a given protein may only be partially digested (or partially deconstructed or partially truncated). Limited or restricted proteolysis may be considered as partial proteolysis. If a given protein has a certain number of potential cleavage points for a given protease (i.e. sites recognizable by a given protease for cleavage), under limited or restricted proteolysis the protease may cleave only at a subset of those cleavage sites.

Limited or restricted proteolysis also includes proteolysis done under limiting conditions whereby the kinetics of protease activity is slowed down to the extent that peptides are cleaved off from the protein one at the time, or at most a few at a time. In some embodiments the kinetic activity of said at least one protease is slowed down so much that said surface-exposed peptides are cleaved off one at a time or at most a few at a time, for example at most 8 (1, 2, 3, 4, 5, 6, 7 or 8) at a time (e.g. at most 8 peptides or at most 8 unique peptides in a sample, e.g. as described elsewhere herein), or at most 7 (1, 2, 3, 4, 5, 6 or 7) at a time (e.g. at most 7 peptides or at most 7 unique peptides in a sample, e.g. as described elsewhere herein), or at most 5 (1, 2, 3, 4 or 5) at a time (e.g. at most 5 peptides or at most 5 unique peptides in a sample, e.g. as described elsewhere herein). In some such embodiments, the proteolysis reaction may go to completion such that the protein is exhausted of peptides that can be cleaved off by a given protease.

As described elsewhere herein, typically, limited or restricted proteolysis results in only the most flexible and/or surface-exposed parts of the protein being cleaved by the protease.

In some embodiments of the present invention, said at least one protease is used under conditions which result in at most 8 surface exposed peptides (e.g. 1, 2, 3, 4, 5, 6, 7 or 8 surface-exposed peptides) being cleaved off from the protein by the action of said protease (e.g. at most 8 peptides or at most 8 unique peptides in a sample, e.g. as described elsewhere herein).

In a preferred embodiment, said at least one protease is used under conditions which result in at most 7 surface-exposed peptides (e.g. 1, 2, 3, 4, 5, 6 or 7 surface-exposed peptides) or at most 5 surface-exposed peptides (e.g. 1, 2, 3, 4 or 5 surface exposed peptides) being cleaved off from the protein by the action of said protease (e.g. at most 7 or at most 5 peptides or at most 7 or at most 5 unique peptides in a sample, e.g. as described elsewhere herein).

Limited or restricted proteolysis in accordance with the present invention can typically be achieved by reducing the protease activity, for example by slowing down the kinetics of protease activity to the extent that peptides are cleaved off from the protein one at the time, or at most a few at a time. In some embodiments the kinetic activity of said at least one protease is slowed down so much that said surface-exposed peptides are cleaved off one at a time or at most a few at a time, for example at most 8 (1, 2, 3, 4, 5, 6, 7 or 8) at a time, or most 7 at a time (1, 2, 3, 4, 5, 6 or 7), or at most 5 (1, 2, 3, 4 or 5) at a time, e.g. as described above.

Any suitable conditions may be used for limited or restricted proteolysis in order to result in only the most flexible and/or surface surface-exposed parts of the protein being cleaved by the protease, for example to result in at most 8 surface exposed peptides, or at most 7 surface exposed peptides, or at most 5 surface exposed peptides being cleaved off by the protease. Conditions which lead to limited or restricted proteolysis may be established by varying the temperature of the digestion reaction and/or the concentration of the protease and/or the duration of the digestion reaction and/or the buffer conditions. The number of peptides being cleaved off from the peptide under particular conditions can be determined by a person skilled in the art (e.g. by mass spectrometry or protein chemistry or biochemistry). Suitable ways of establishing appropriate conditions for limited or restricted proteolysis are also described elsewhere herein. Appropriate limited or restricted proteolysis conditions can be established for different proteins or for different proteases or for the particular combination of protein and protease being used. Particularly preferred conditions for limited or restricted proteolysis are described in the Examples herein. Conditions used for limited or restricted proteolysis typically do not alter (or do not significantly alter) the native configuration (native form) of the protein. Cofactors of the protein may be, but are not necessarily, present during limited or restricted proteolysis.

Appropriate conditions for limited or restricted proteolysis may differ depending on the protease and/or protein but are generally conditions that are suboptimal for the protease in question, e.g. such that the kinetics of protease activity is significantly slowed down or reduced.

Conditions which confer (or provide) a low proteolytic activity of the protease (e.g. a lower or significantly lower than optimal proteolytic activity) are generally used. Such conditions include, but are not limited to, using a low concentration of the protease and/or a working temperature that is suboptimal for the protease in question and/or a non-standard or suboptimal buffer for the protease in question and/or a short contact (incubation) time for the protease with the protein.

In some embodiments, limited or restricted proteolysis (e.g. using trypsin or e.g. using a protease with an optimum working temperature of for example 37° C. or above) is performed at room temperature (e.g. about 20° C. or 17-23° C. or 20-25° C.).

In some embodiments, limited or restricted proteolysis is performed at a temperature that is at least 2° C., at least 5° C., at least 10° C., or at least 20° C. above or below, or significantly above or below, (preferably below) the optimum working temperature of the protease being used. In some embodiments, limited or restricted proteolysis is performed at a temperature that is 2° C. to 5° C., 2° C. to 10° C., 2° C. to 20° C., 2° C. to 30° C., 5° C. to 10° C., 5° C. to 20° C., 5° C. to 30° C., 10° C. to 20° C., 10° C. to 30° C., 20° C. to 30° C. above or below (preferably below) the optimum working temperature of the protease being used.

In some embodiments, a concentration of up to 5 μg/ml protease (e.g. trypsin) is used for limited or restricted proteolysis. In some embodiments a concentration of up to 0.5 μg/ml, up 30 to 1 μg/ml, up to 2 μg/ml, up to 5 μg/ml, up to 10 μg/ml or up to 20 μg/ml protease is used for limited or restricted proteolysis. Preferably, for limited or restricted proteolysis, a protease concentration of 5 μg/ml or less is used (e.g. up to 1 μg/ml, up to 2 μg/ml, up to 3 μg/ml, up to 4 μg/ml or up to 5 μg/ml) In some embodiments, the limited proteolysis reaction is allowed to proceed for up to or less than 5 minutes, 10 minutes, 15 minutes, 30 minutes, one hour or five hours, with the shorter incubation times generally being preferred. For example, in some embodiments, the limited proteolysis reaction is allowed to proceed for up to or less than 5 minutes, 10 minutes, 15 minutes, 30 minutes. In some preferred embodiments, the limited or restricted proteolysis reaction is a reaction that is allowed to proceed for 5 minutes or less (e.g. 4 minutes or less, 3 minutes or less, 2 minutes or less or 1 minute or less). Typically, if a high (or higher) concentration of protease is used, then a short (or shorter) incubation time is used. Purely, by way of example, if a concentration of 20 μg/ml protease (or higher) is used then an incubation time of 5 minutes or less may be used. In some such embodiments, limited proteolysis is performed at room temperature. Thus, in some embodiments, limited proteolysis is performed with a concentration of up to 5 μg/ml protease (e.g. about 5 μg/ml protease) for up to about 5 minutes (e.g. about 5 minutes) at room temperature.

In some embodiments, limited proteolysis or restricted proteolysis is proteolysis (a proteolysis reaction) that results in (or achieves) the cleavage of 15% or less, or 10% or less, or 5% or less (e.g. 1%, 2%, 3%, 4% or 5%) of the sites (bonds) in the protein that are potentially cleavable (digestable) by the protease being used. Alternatively viewed, in some embodiments, limited proteolysis achieves 15% or less, or 10% or less, or 5% or less (e.g. 1%, 2%, 3%, 4% or 5%) proteolysis. The sites in a given protein that are potentially cleavable by the protease being used can be readily identified by a skilled person based on the knowledge of the protein sequence and the substrate specificity of the protease being used (e.g. by using a computer such as Peptidecutter (Expasy, SIB Swiss Institute of Bioinformatics). Typically, cleavage at all the potential sites in the linear amino acid sequence of the protein would represent the "100%" value (although the "100%" value could alternatively be set as the total number of potential sites in the protein that, if cleaved, would release (or yield) peptides that are of a length that is readily detectable by the instrument being used, e.g. the MS instrument being used). Alternatively, the "100%" value could be set as the number of potentially cleavable sites in the protein that are known to be (or are predicted to be e.g. by using protein modeling tools) in a region of the protein that is accessible to a protease (e.g. an extracellular part or domain of a protein, or e.g. not a part or region or domain of a protein that is within the cell membrane, or not a cysteine rich part of the protein or not a post-translationally modified part of the protein, or not a beta sheet). 30 The number (and location) of sites that are actually cleaved by the protease can also be readily determined by a skilled person (e.g. using mass spectrometry) and thus the percentage of potentially cleavable sites that are actually cleaved can be readily determined.

In some embodiments, limited or restricted proteolysis may be considered a proteolytic step that is performed under one or more of the conditions described herein in connection with limited or restricted proteolysis.

In some embodiments, proteolytic digestion reactions may be stopped using formic acid or aqueous ammonia. For example, trypsin, Asp-N, Proteinase K and chymotrypsin may be stopped using formic acid and pepsin may be stopped using aqueous ammonia.

In some embodiments of the present invention, the cleaved off surface exposed peptides are ranked based on order of appearance after being contacted with said at least one protease, wherein the surface exposed peptides that are cleaved off first (or early) and detected in the first (or early) sampling points are given a high rank and the surface exposed peptides that are cleaved off late and detected in subsequent sampling points are given a low rank. Highly-ranked peptides, coming off the target protein quickly, also having functional significance may typically be used for epitope development, immunization and subsequent antibody generation.

In some embodiments of the invention, the surface exposed peptides that are cleaved off under conditions of low (less harsh) proteolytic activity as described herein (e.g. low(er) concentration of protease, low(er) temperature of incubation, and/or short(er) time of incubation, generally easily digested peptides) are given a high rank and the surface exposed peptides that are cleaved off under conditions of high (more harsh) proteolytic activity as described herein (e.g. high(er) concentration of protease, high(er) temperature of incubation and/or long(er) temperature of incubation, generally less easily digested peptides) are given a low rank.

In some embodiments, multiple samples of proteolytically digested material (or eluate from the proteolytic digestion reaction) may be taken during a limited or restricted proteolysis reaction (e.g. sequentially) and/or multiple samples (e.g. multiple limited or restricted proteolysis reactions) may be processed (or run) separately (e.g. processed or run in parallel).

In some embodiments, multiple samples of proteolytically digested material (or eluate from the proteolytic digestion reaction) are taken (or obtained) at time intervals (e.g. 1 minute, 2.5 minutes or 5 minute intervals) during limited or restricted proteolysis of the protein. In some such embodiments, the protease and/or (typically "and") the protease concentration (and/or other conditions that may affect proteolysis as described elsewhere herein) may be constant for (or in) each of the samples, with the samples varying based on the time (or duration) of contact (or incubation) with the protease. In some such embodiments, samples may be obtained in sequence (sequential digestion).

In some embodiments, multiple samples (e.g. multiple limited or restricted digestion reactions) are processed (or run) separately, with each sample having different proteolytic conditions or proteolytic activities for limited or restricted proteolysis of the protein, for example as discussed elsewhere herein, e.g. different proteases and/or different protease concentrations and/or different temperatures and/or different times of incubation may be used in different samples. In some such embodiments, the time (or duration) of the contact (or incubation) with the protease is typically (and preferably) constant for (or in) each of the samples. In some such embodiments, samples may be processed (or run) in parallel.

In some embodiments of methods of the invention, the number of surface exposed peptides being cleaved off from the protein by the action of said protease is controlled by time at a constant concentration of protease and several samples are taken over time, or the number of surface exposed peptides being cleaved off from the protein by the action of said protease is controlled by the concentration of the protease at constant time, and several samples can be taken (or run) at several different concentrations of the protease, or the number of surface exposed peptides being cleaved off from the protein by the action of said protease is controlled by both time and concentration of said protease.

Each sample (or preferred samples) may preferably contain one or a few peptides (e.g. up to 8 peptides or up to 8 unique peptides) that have been cleaved off from the protein. Thus, one or a few peptides (e.g. up to 8 peptides or up to 8 unique peptides) that have been cleaved off from the protein may be detected in each sample. A unique peptide is a peptide that is not present in a previous sample or not present in a sample with weaker (or less harsh) proteolytic conditions (e.g. is distinct from or different from peptides present in a previous sample or in a sample with weaker proteolytic conditions). Accordingly, a sample that contains up to 8 unique peptides may contain greater than 8 different peptides, but one or more of these peptides may have been detected in a previous sample or in a sample with weaker proteolytic conditions (and thus one or more of these peptides may be a non-unique peptide).

Ideally, and preferably, each sample would contain only a single cleaved off peptide. For example, a single cleaved off peptide may be detected in the first sample (or sampling point) and a single cleaved off peptide may be detected in one or more subsequent samples (or sampling points). In other examples, multiple cleaved off peptides (e.g. up to 8 peptides or up to 8 unique peptides) may be detected in the first and/or subsequent samples (sampling points). Conditions that yield one or a few cleaved off peptides per sample (e.g. up to 8 peptides or up to 8 unique peptides per sample) can be established by using short sampling intervals, different protease concentrations, different buffer compositions, different temperatures, different salt concentrations, or protease inhibitors (or a combination thereof). Cleaved-off peptides may be ranked based on the sample (sampling point) in which they appear. For example, under conditions which result in the detection of only one peptide per sampling point, the peptide in the first sample taken is given the highest rank, the peptide in the second sample taken is given rank 2, etc. Using conditions whereby only a single cleaved off peptide is detected at each sampling point, ranking of individual peptides is possible. Using conditions whereby multiple cleaved off peptides are detected at each sampling point, ranking of groups of peptides is possible.

In some embodiments, higher ranked surface-exposed peptides (cleaved off peptides) are preferred. In some embodiments, the surface-exposed peptide (e.g. a high rank peptide) in accordance with the invention is a cleaved off peptide that is detected in (or present in) the first sample taken. In some embodiments, a surface-exposed peptide in accordance with the invention (e.g. a high ranked peptide) is a cleaved off peptide that is one of the top 8 ranked peptides (e.g. top 8 ranked unique peptides) or is present in a sample containing one of the top 8 ranked peptides (e.g. top 7 ranked, or top 5 ranked) peptides (e.g. top 8, top 7 or top 5 ranked unique peptides) in terms of its order of appearance in a sample(s) taken during limited or restricted proteolysis of the protein. Such peptides may be detected in (or present in) the first sample taken, or may be present in one or more subsequently taken samples.

Peptides that are cleaved off from the protein first (or early) (e.g. those in the first sample taken (first sampling point) as described above or those that are ranked in the top 8 peptides (e.g. top 8 ranked unique peptides) based on order of appearance during limited or restricted proteolysis as described above) are typically those that are well exposed (e.g. surface exposed) and thus are easily accessed by the protease. Such first (or early) digested peptides are given a high rank (e.g. the first appearing peptide is given rank 1, the second given rank 2, etc.). Peptides that are cleaved off from the protein later (e.g. in a later sampling point than the early peptides) are typically those that are not as well exposed and thus are not as easily accessed by the protease. Such later digested peptides are given a lower rank. In the present invention, peptides having a high rank are typically preferred.

In some embodiments, cleaved off peptides (surface exposed peptides) having amino acid sequences that are most exposed at the surface of the protein are preferred for antigenic epitope development.

In some embodiments, peptides (cleaved-off peptides) may be ranked based on their functional importance, or predicted functional importance, to the protein. Typically, those peptides having amino acid sequences that are functionally important, or predicted to be of functional importance, to the protein are given a higher rank than those that are not, or not predicted to be, of functional importance. In some embodiments, it is the higher ranked peptides that are preferred.

In some embodiments, peptides having amino acid sequences that are functionally important, or that are predicted to be functionally important, to the protein (e.g. have a high rank for functional importance) and which additionally have a high rank based on surface exposure (e.g. a peptide in the first sample taken (first sampling point) as described above or those that are ranked in the top 8 peptides (e.g. top 8 ranked unique peptides) based on order of appearance during limited or restricted proteolysis as described above) are preferred for antigenic epitope development (or put another way are preferred peptides upon which to base an antigenic epitope).

In some embodiments, peptides having amino acid sequences that are functionally important, or that are predicted to be functionally important, to the protein (e.g. have a high rank for functional importance), but which do not additionally have a high rank based on surface exposure (e.g. are not peptides in the first sample taken (first sampling point) as described above or those that are ranked in the top 8 peptides (e.g. top 8 ranked unique peptides) based on order of appearance during limited or restricted proteolysis as described above) may be used for antigenic epitope development.

In some embodiments, peptides having amino acid sequences that are not functionally important, or that are not predicted to be functionally important, to the protein (e.g. have a low rank for functional importance) but which have a high rank based on surface exposure (e.g. a peptide in the first sample taken (first sampling point) as described above or those that are ranked in the top 8 peptides (e.g. top 8 ranked unique peptides) based on order of appearance during limited or restricted proteolysis as described above) may be used for antigenic epitope development.

In some embodiments, an antigenic epitope is based on a surface exposed peptide that is cleaved off first (or early) from said protein (e.g. a peptide in the first sample taken (first sampling point) as described above or a peptide that is ranked in the top 8 peptides (e.g. top 8 ranked unique peptides), based on order of appearance during limited or restricted proteolysis as described above), irrespective of the functional importance, or predicted functional importance, of the amino acid sequence of the cleaved off peptide.

In some embodiments, an antigenic epitope is based on a surface exposed peptide that is ranked in the top 8 peptides (e.g. top 8 ranked unique peptides), based on order of appearance during limited or restricted proteolysis, of those peptides that additionally have an amino acid sequence that is functionally important, or predicted to be of functional importance, to the protein. These peptides are not necessarily (but may be) the same as the set of the absolute top ranked 8 peptides based on order of appearance alone (as described above).

In some embodiments, a region of interest on a protein is identified or selected which is, or is predicted to be, functionally important to the protein, and an antigenic epitope is based on a surface exposed peptide that is ranked in the top 8 peptides (e.g. top 8 ranked unique peptides), based on order of appearance during limited or restricted proteolysis, of those peptides that additionally have an amino acid sequence that cleaved off from said region of interest. These peptides are not necessarily (but may be) the same as the set of the absolute top ranked 8 peptides based on order of appearance alone (as described above).

In some embodiments, antigenic epitopes for antibody generation are based on the amino acid sequence of a peptide (surface exposed peptide) that has been cleaved off first (or early) (e.g. a peptide in the first sample taken (first sampling point) as described above or a peptide that is ranked in the top 8 peptides (e.g. top 8 ranked unique peptides) based on order of appearance during limited or restricted proteolysis as described above) from said protein by the action of the protease during limited proteolysis and thus which has a high rank.

Thus, in some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides) based on order of appearance during limited or restricted proteolysis as described above) for antigenic epitope development and raising an antibody against said antigenic epitope that is based on (or developed from) said surface-exposed peptide.

In some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides based on order of appearance during limited or restricted proteolysis as described above), constructing an antigenic epitope based on said surface-exposed peptide and raising an antibody against said antigenic epitope.

In some embodiments, methods of the invention comprise picking a surface exposed peptide having a high rank (e.g. a peptide in the first sample taken (first sampling point) as described above or a peptide that is ranked in the top 8 peptides (e.g. top 8 ranked unique peptides) based on order of appearance during limited or restricted proteolysis as described above) and correlating it with a defined biological property (or biological function) of the protein, constructing an antigenic epitope based on said surface-exposed peptide and raising an antibody against said antigenic epitope. Peptides having an amino acid sequence which correlates with a defined biological property (or function) of the protein are typically preferred.

Any means for identifying the cleaved off peptides (surface-exposed peptides) may be employed. In some embodiments, cleaved off peptides are identified using mass spectrometry. In some embodiments, liquid chromatography in combination with mass spectrometry is used. Preferably, cleaved off peptides (surface-exposed peptides) are identified with LC-MS/MS (liquid chromatography-tandem mass spectrometry). Exemplary and preferred mass spectrometry methodologies are described in the Examples. Tandem mass-spectra may be searched by MASCOT (Matrix Science, London, UK) against an appropriate database, e.g. as described in the Examples.

A digested, deconstructed or truncated protein as referred to herein is a protein that has been cleaved at one or more sites along its length by a protease. Such proteolytic cleavage results in one or more peptides (surface exposed peptides) being cleaved off from (i.e. released from) the protein. Thus, a surface exposed peptide is a peptide that has been cleaved off from a protein by the action of the protease. The term "surface exposed" reflects the fact that, typically, in the context of the full-length protein (i.e. the uncleaved protein), the portion of the protein that corresponds to the cleaved off (released) peptide sequence is well exposed and accessible to the protease.

The present invention provides new methods for therapeutic antibody discovery, and new pharmacologically active antibodies directed to the human TRPV1 protein.

The present invention relates to methods of detecting epitopes on proteins that are well exposed and thus may be utilized as guides for antibody targeting.

Some methods of the present invention comprise a step of identifying an antigenic epitope by identifying a surface-exposed peptide that is cleaved off that has an amino acid sequence that is, or that is predicted to be, of functional importance (e.g. biological importance) to said protein, and generating an antigenic epitope based on such a surface-exposed peptide. In some embodiments, an antibody is raised against such an antigenic epitope.

Identifying whether or not a surface-exposed peptide that is cleaved off from said protein has an amino acid sequence that is, or is predicted to be of functional importance to said protein can be done by any suitable means and a person skilled in the art will readily be able to do this.

For example, in some embodiments, a protein that is digested, deconstructed or truncated during limited or restricted proteolysis is tested in a functional assay to assess whether its function or functional activity (e.g. biological function) has been altered. This may be done by comparing the level of functional activity of the digested, deconstructed or truncated protein to the level of functional activity of the protein that has not been subjected to limited or restricted proteolysis (the level of functional activity of the protein that has not been subjected to limited or restricted proteolysis can be considered a control level). If the biological function of a protein is altered after (or during) the limited or restricted proteolysis, this indicates that the cleaved off-peptide(s) (surface exposed peptide(s)) has been cleaved off (released) from a region of the protein that is of functional relevance to the protein (e.g. that is of biological importance). Accordingly, cleaved-off surface exposed peptides can be correlated with functional data to assess the functional importance of the surface-exposed peptides to the protein. The cleaved off peptide(s) can be identified (e.g. the sequence(s) of the cleaved off peptide(s) can be identified), e.g. in a parallel experiment, as described elsewhere herein (e.g. by LC-MS/MS). If the cleaving off of a peptide (surface-exposed peptide) from the protein results in an alteration of the functional activity of the protein, this indicates that the surface-exposed peptide may be particularly useful for antigenic epitope generation in the present invention. Alternatively viewed, an antigenic epitope based on such a surface-exposed peptide may be particularly useful and preferred for antibody generation.

In one embodiment the protein is TRPV1 and the assay to determine the functional importance of the cleaved off peptides to TRPV1 is an inside-out patch-clamp assay as described elsewhere herein.

An "altered" or "alteration in" function or functional activity can be any measurable alteration, preferably a significant alteration, more preferably a statistically significant alteration. An "altered" function or "alteration in function" may be an increase or decrease in function. Exemplary alterations in function are alterations of ≥2%, ≥3%, ≥5%, ≥10%, ≥25%, ≥50%, ≥75%, ≥100%, ≥200%, ≥300%, ≥400%, ≥500%, ≥600%, ≥700%, ≥800%, ≥900%, ≥1000%, ≥2000%, ≥5000%, or ≥10,000%. Alterations are typically as assessed in comparison to an appropriate control level of function or functional activity, for example in comparison to the function or functional activity of the equivalent protein that has not been subjected to limited or restricted proteolysis.

In some embodiments, an antigenic epitope is based on the amino acid sequence of a surface-exposed peptide that, when cleaved off from the protein, results in an alteration in the function or functional activity of the protein.

In some embodiments, whether or not the surface-exposed peptide sequence is of functional importance (e.g. biological importance) is predicted or determined by bioinformatic means and/or by using other information (e.g. in academic literature) that is already known about functionally important regions of the protein. Accordingly, cleaved off surface exposed peptides can be correlated with data that is known about functionally important regions of the protein to predict or determine the functional importance of the cleaved off peptide to the protein. If the amino acid sequence of the surface-exposed peptide is known to be (or is predicted to be) of functional importance, this indicates that the surface-exposed peptide may be particularly useful for antigenic epitope generation in the present invention. Alternatively viewed, an antigenic epitope based on such a surface-exposed peptide may be particularly useful and preferred for antibody generation.

Thus, in some embodiments, an antigenic epitope is based on the amino acid sequence of a surface exposed peptide that is known to be (or is predicted to be) functionally important, e.g. based on bioinformatic analysis and/or based on other information (e.g. in academic literature) that is already known about functionally important regions of the protein.

In some embodiments, the antigenic epitope is an antigenic epitope of TRPV1 that is based on the amino acid sequence of a surface exposed peptide that correlates with (or corresponds to) a calmodulin binding sequence of TRPV1 or the capsaicin binding site of TRPV1.

In some embodiments, a functional assay to determine the functional importance of a surface-exposed peptide is performed in addition to predicting or determining the functional importance of a surface-exposed peptide by bioinformatic means and/or by using other information (e.g. in academic literature) that is already known about functionally important regions of the protein.

"Bioinformatic means", "bioinformatic analysis", "bioinformatic data" and "bioinformatic information" includes, but is not limited to, database searching (e.g. BLAST searching), structural modeling, or structural biology and data/information obtained thereby.

Function (e.g. biological function) can include any biological or physiologically relevant function for the protein in question. Function (e.g. biological function) includes, but is not limited to the capability of the protein to bind to a target (such as a ligand or receptor) or other binding partner e.g. a cofactor, signalling activity, enzymatic activity of the protein, and ion channel activity, transporter activity, release e.g. insulin release and uptake machinery, etc. Thus, functionally relevant or functionally important regions of the protein include, but are not limited to, regions that confer the ability of the protein to bind to a target (such as a ligand or receptor) or other binding partner e.g. a cofactor, regions that confer signalling activity, regions that have an enzymatic activity of the protein, regions that confer ion channel activity, regions conferring transporter activity and regions conferring release and uptake of molecules (e.g. insulin).

In one embodiment, a method of the invention further comprises a step of in silico generation of a set of putative peptides (e.g. all putative peptides) that could be cleaved off from the protein by one or more protease (e.g. by using a computer program that can identify cleavage points in a protein based on the known recognition sequence(s) of said one or more proteases), and optionally filtering said in silico generated set of putative peptides to remove peptides that have previously been described (e.g. in sequence databases for example BLAST searching or in other literature) thereby obtaining a filtered list of putative peptides, comparing said filtered list of putative peptides to a list of peptides identified by limited or restricted proteolysis of the protein, identifying the peptides that are common to both said filtered list and said list of peptides identified by limited or restricted proteolysis of the protein, identifying (or constructing) an antigenic epitope based on a peptide common to both lists, and optionally raising an antibody to said antigenic epitope.

In another aspect, the present invention provides a method of identifying an antigenic epitope, said method comprising:
   (i) exposing a first protein to limited or restricted proteolysis by contacting the first protein with at least one protease to form at least one digested, deconstructed or truncated version of the first protein and at least one surface-exposed peptide that is cleaved off from the first protein by the action of said protease;
   (ii) identifying an amino acid sequence of a region (or part or portion) of a second protein that is identical to or substantially homologous to the amino acid sequence of a surface-exposed peptide that is cleaved off from the first protein; and
   (iii) generating an antigenic epitope based on the amino acid sequence of said region (or part or portion) of said second protein that is identical to or substantially homologous to the amino acid sequence of a surface-exposed peptide that is cleaved off from the first protein; and optionally
   (iv) raising an antibody against the antigenic epitope.

Exemplary types of substantially homologous sequence are discussed elsewhere herein. Such a method can facilitate antigenic epitope generation for a protein (a second protein) based on limited or restricted proteolysis performed on a different protein (a first protein). This may be particularly useful when the first and second proteins are in the same protein family or otherwise related, for example data from limited or restricted proteolysis performed on TRPV1 may be used to identify a TRPV2 antigenic epitope. Determining (or identifying) substantially homologous proteins on a second protein may be done using any suitable means (e.g. computer programs) and a skilled person will familiar with these. Purely by way of example, the EMBOSS Needle program provided by EMBL-EBI is a suitable computer program. EMBOSS Needle reads two input sequences and writes their optimal global sequence alignment, the computation using the Needleman-Wunsch alignment algorithm to find the optimum alignment (including gaps) of two sequences along their entire length.

In some embodiments of the invention, an antigenic epitope is not based on a surface exposed peptide that has an amino acid sequence that is conserved with another protein(s) (e.g. an evolutionarily conserved sequence or a sequence that is identical to or substantially homologous to the amino acid sequence of the surface exposed peptide). This may minimise the cross-reactivity (or non-specific binding) of the antibodies raised against such antigenic epitopes. Put another way, antigenic epitopes based on unique amino acid sequences (or sequences not found in other proteins) can be used in some embodiments The present invention relates to methods of detecting epitopes on proteins that are functionally relevant and thus may be utilized as guides for antibody targeting. More specifically, such methods include proteomic tools to reveal hot spot epitopes of target proteins. These epitopes that potentially can be used as antigens in the production of antibodies are denoted antigenic epitopes herein.

In an aspect of the invention, a protein is digested, deconstructed and/or truncated through protease action and in parallel probed by one or more functional assays on the digested, deconstructed and/or truncated protein to delineate functionally important region(s) of the protein.

In an embodiment the digestion, deconstruction and/or truncation of the protein may be performed in parallel by functional assay(s) to delineate functionally important regions of the protein to guide epitope selection for antibody generation.

In an embodiment, a single protease may be used to digest, deconstruct and/or truncate the protein. In another embodiment, multiple proteases may be used to digest, deconstruct and/or truncate the target protein, sequentially one at a time or in parallel. Such proteases are exemplified but not limited to Arg-C proteinase, Asp-N endopeptidase, Clostripain, Glutamyl endopeptidase, Lys-C, Lys-N, Trypsin, Chymotrypsin, Proteinase K and Thermolysin. A region that is easily digested by several proteases should be located in an exposed region of the protein and a region that is only digested by a single protease is probably located in a more hidden region. Alternatively, the protease has unique cleaving specificity or/and physicochemical properties or/and structural features such that it can identify surface-exposed peptides on a target protein that other proteases cannot. Thus, the usage of multiple proteases is preferable, and each different protease can yield complementary or unique information about surface-exposed peptides suitability as antigenic epitopes.

Sequential use of multiple proteases means that different proteases are incubated with the protein one after another, i.e. one protease is incubated, followed by another at a later time point, and optionally one or more other different proteases at a later time point(s).

Sequential use of a single protease means that the same protease (e.g. the same concentration of protease) is incubated with the protein several times, e.g. at several different (sequential) time points or that several samples are taken over time from the proteolytic digest reaction, and the appearance of new or unique peptides generated in the reaction are detected and followed over time.

Parallel use means that multiple separate, single-protease digestion reactions are performed, each with a different protease, or with the same protease but different proteolytic conditions, for example as described elsewhere herein e.g. different protease concentrations and/or temperatures and/or time points.

Multiple proteases may be used in order to identify overlapping, complementary or unique surface-exposed peptides. In this context "overlapping" means that a surface-exposed peptide identified via limited or restricted proteolysis with one protease has an amino acid sequence which overlaps (partially or fully) with the amino acid sequence of a surface-exposed peptide identified via limited or restricted proteolysis with one or more other (i.e. different) proteases. In this context, "complementary" means that a surface-exposed peptide identified via limited or restricted proteolysis with one protease has an amino acid sequence which, in the context of the entire protein sequence (i.e. the entire protein sequence before limited or restricted proteolysis), lies next to or close to (or even partially overlaps with) the amino acid sequence of a surface-exposed peptide identified via limited or restricted proteolysis with one or more other (i.e. different) proteases. A "unique" surface exposed peptide is surface-exposed peptide that is only identified after limited or restricted proteolysis with one or few (the minority) of the proteases tested.

Without wishing to be bound by theory, a region of the protein that is cleaved by more than one protease is likely to be in a well exposed (e.g. surface exposed) region of the protein and thus surface-exposed peptides from a region of the protein that is cleaved by more than one protease may represent particularly useful surface-exposed peptides upon which to base antigenic epitopes.

Using multiple proteases includes, but is not limited to, using 2, 3, 4, 5 proteases.

In some embodiments of methods of the present invention, the protease is selected from the group consisting of trypsin, Arg-C proteinase, Asp-N endopeptidase, Clostripain, Glutamyl endopeptidase, Lys-C, Lys-N, Chymotrypsin, Proteinase K, Thermolysin, Pepsin, Caspase 1, Caspase 2, Caspase 3, Caspase 4, Caspase 5, Caspase 6, Caspase 7, Caspase 8, Caspase 9, Caspase 10, Enterokinase, Factor Xa, GranzymeB, Neutrophil elastase, Proline-endopeptidase, Staphylococcal peptidase I, and Thrombin.

In some preferred embodiments, the protease is selected from the group consisting of trypsin, Asp-N endopeptidase, Chymotrypsin, pepsin and Proteinase K. In a preferred embodiment, the protease is trypsin.

In yet another aspect of the invention a cocktail of several proteases are used together in single, or multiple challenges spaced in time with constant or varying concentration of one or several of the proteases. Thus, in some embodiments a single cocktail (mixture) of multiple proteases is used.

If multiple proteases are used a rank-ordered list may be generated for each individual protease.

This method will yield new fundamental understanding of protein function, and new methodology/technology for rapid and precise development of pharmacologically active antibodies that can be used to treat a medical condition in humans and/or animals. The method can be generalized to all proteins, soluble or membrane bound, extracellular or intracellular.

The list of epitopes generated by the proposed method is preferably sorted versus curated bioinformatics data and functional assay(s). The method preferably uses input data from both experiments, and bioinformatic information. In an embodiment, focus will be on membrane, and membrane-associated proteins. Such proteins are exemplified but not limited to the human nociceptor TRPV1, other ion channels in the TRP superfamily, as well as some excitatory amino acids receptors including the NMDA receptor, and G-proteins. These proteins (e.g. ion channels) have the advantage that they can be studied directly in a detailed way using, for example, patch clamp. Other classes of proteins of interest are related to oncogenic proteins, including the oncogenic small GTPases KRAS, NRAS and HRAS. KRAS is a key protein in several metastatic malignancies including pancreatic carcinoma, colon carcinoma, and lung carcinoma. GTPase activity can e.g. be studied by radioisotopic labeling of GTP followed by measurement of free 32P after GTP hydrolysis to GDP or pull-down assays followed by western blot. Yet other interesting protein classes are immunomodulatory proteins involved in immunomodulation in cancer therapy such as PD1, PDL1, CD 40 just as a few examples.

A "protein" in accordance with the present invention may be any protein.

In some embodiments of the present invention, the protein is a membrane bound protein, a soluble (e.g. circulating) protein, an extracellular protein or an intracellular protein.

In some embodiments, the protein is a membrane or a membrane associated protein.

In some embodiments, the protein is an ion channel, e.g. an ion channel in the TRP superfamily (e.g. TRPV1 or TRPV2). In a preferred embodiment, the protein is TRPV1.

In some embodiments, the protein is an excitatory amino acid receptor. In some such embodiments the protein is the NMDA receptor or a G-protein.

In some embodiments, the protein is an oncogenic protein. In some such embodiments the protein is an oncogenic small GTPase selected from the group consisting of KRAS, NRAS and HRAS.

In some embodiments, the protein is an immunomodulatory protein. In some such embodiments the protein is selected from the group consisting of PD1, PDL1, CD40, OX40, VISTA, LAG-3, TIM-3, GITR and CD20.

In some embodiments, the protein is a protein included in any one of Tables 9, 10, 11 or 12 herein. Thus, in some embodiments, the protein is a protein selected from the group consisting of (or comprising) Mannosyl-oligosaccharide 1,2-alpha-mannosidase IA, Fatty aldehyde dehydrogenase, CD81 antigen, Olfactory receptor 1B1, Chloride channel CLIC-like protein 1, Probable G-protein coupled receptor 83, PRA1 family protein 3, Glycerol-3-phosphate acyltransferase 4, POTE ankyrin domain family member F, NADH-cytochrome b5 reductase 3, Kininogen-1, Rho-related GTP-binding protein RhoC, Sodium/hydrogen exchanger 6, Amyloid-like protein 2, Membrane-associated progesterone receptor component 1, Phospholipase D4, Matrix metalloproteinase-14, Atlastin-3, Protein YIF1A, Vesicle-associated membrane protein 1, Chloride channel CLIC-like protein 1, Golgin subfamily B member 1, Dehydrogenase/reductase SDR family member 7B, Anion exchange transporter, Transmembrane protein 192, Transmembrane and ubiquitin-like domain-containing protein 1, Polypyrimidine tract-binding protein 1, RNA-binding protein Musashi homolog 2, Death domain-associated protein 6, Putative ubiquitin-conjugating enzyme E2 N-like, Ubiquitin-conjugating enzyme E2 N, Alpha-centractin, AP-2 complex subunit beta, mRNA-decapping enzyme 1A, Calumenin and RNA-binding protein 14.

In some embodiments, the protein is not urokinase plasminogen activator receptor (u-PAR), transglutaminase 3 (TGase3), a *Neisseria meningitidis* protein or a cannabinoid receptor 35 (e.g. CB1).

In some embodiments, the protein is a eukaryotic protein. For example, in some embodiments the protein is a mammalian protein, preferably a human protein.

In some embodiments, the protein is any protein of the human proteome. Put another way, human proteins are preferred.

The usage of a single, or multiprotease limited digestion protocol to these targets will lead to the discovery of new antibodies directed to hot spot epitopes. Different proteases will produce different cleaved off peptides. In an embodiment, membrane proteins are deconstructed and effects of this piece-by-piece truncation are probed for effect on protein function. Rare spots only observed with certain proteases will also be identified. The identified data will then be analyzed against curated bioinformatic data and also from functional assays of truncated proteins, to recognize functionally important regions of the protein in question.

An aspect of the embodiments relates to a method of identifying an antigenic epitope in a protein. The method comprises exposing the protein to limited or restricted proteolysis by contacting the protein to at least one protease to form at least one digested, deconstructed or truncated version of the protein and at least one surface-exposed peptide. In another embodiment, the method also comprises probing the at least one digested, deconstructed or truncated version of the protein in a functional assay that tests, checks or verifies at least one biological function of the protein. The method further comprises identifying an antigenic epitope in the protein as a surface-exposed peptide among the at least one surface-exposed peptide and present in a region of the protein involved in exerting the biological function of the protein as determined based on the functional assay.

In an embodiment, exposing the protein to the limited or restricted proteolysis comprises contacting the protein to the at least one protease i) at a selected temperature or temperature range, ii) at a selected concentration or concentration range of the at least one protease (relative to a concentration of the protein) and/or ii) during a selected duration. This in turn enables the at least one protease to cleave surface-exposed regions of the protein but not non-flexible and/or internal regions of the protein.

Exposing the protein to limited or restricted proteolysis by contacting the protein to at least one protease implies that the protein is exposed to a mild proteolysis. As a consequence, in particular surface exposed and flexible peptide portion(s) of the protein will be cleaved off from the amino acid sequence by the action of the at least one protease. The temperature, concentration and/or duration used in the proteolysis typically depends on the particular protease(s) and the current protein. Thus, in an embodiment a set of candidate proteolysis conditions are first tested in order to select or identify a suitable temperature, concentration of protease and/or duration used to digest, and buffer conditions to deconstruct or truncate the protein and get at least one surface-exposed peptide. For instance, proteolysis can be performed at multiple, i.e. at least two, different reaction temperatures, at multiple different protease concentrations (relative the concentration of the protein) and/or at multiple different reaction durations, including different buffer conditions, as shown in FIG. 1 in order to identify the most appropriate proteolysis conditions for the current combination of protein and protease(s).

A suitable protease condition is, for instance, temperature, concentration and/or duration that results in the digestions, deconstruction or truncation of the protein into one or at most N surface-exposed peptides. A typical value of the parameter N is 7, preferably 6 or 5, more preferably 4 or 3 or even more preferably 2 or 1.

In an embodiment, the functional assay tests, checks or verifies at least one biological function of the protein. Non-limiting examples of such biological function include the capability of the protein to bind to a target, such as a ligand or receptor; enzymatic activity of the protein; ion channel activity; etc.

In an embodiment, exposing the protein to the limited or restricted proteolysis comprises exposing the protein to the limited or restricted proteolysis by contacting the protein to multiple proteases to form multiple digested, deconstructed or truncated versions of the protein and multiple surface-exposed peptides. In a particular embodiment, the protein is contacted to the multiple proteases serially, i.e. one after another. In another particular embodiment, the protein is contacted to the multiple proteases in parallel.

In an embodiment, identifying the antigenic epitope comprises identifying a surface-exposed epitope among the at least one surface-exposed peptide that is present in region that results in lack of or significantly altered biological function of the protein when the region is cleaved off or removed from the protein during the limited or restricted proteolysis.

In an embodiment, the method also comprises selecting at least one target region within the protein based on bioinformatics and/or known data of biological function of the protein. In such a case, identifying the antigenic epitope comprises identifying a surface-exposed peptide among at least one surface-exposed peptide present in a region of the protein among the at least one target region.

In this embodiment, bioinformatics and/or other known data of the biological function is used to guide the antigenic epitope selection. This means that only surface-exposed peptides that are present in one of the selected target regions(s) are used as candidates when identifying or selecting the antigenic epitope. Accordingly, the number of candidates can be reduced by removed or omitting surface-exposed peptides that are present in regions known to lack any biological function and/or known to not be involved in exerting the biological function of the protein.

Another aspect of the embodiments relates to an antigenic epitope identified according to the above described method of identifying an antigenic epitope in a protein.

In one embodiment, the present invention provides an antigenic epitope of TRPV1 comprising (or consisting of) an amino acid sequence selected from the group consisting of:

```
                                  (SEQ ID NO: 2)
LLSQDSVAASTEK;
                                  (SEQ ID NO: 3)
LLSQDSVAASTEKTLR;
and
                                  (SEQ ID NO: 4)
QFSGSLKPEDAEVFKSPAASGEK,
``` or a sequence substantially homologous thereto.

In another embodiment, the present invention provides an antigenic epitope of TRPV1 comprising (or consisting of) an amino acid sequence selected from the group consisting of:

```
                                  (SEQ ID NO: 5)
LLSQDSVAASTEKTLRLYDRRS;
and
```

GRHWKNFALVPLLRE. (SEQ ID NO: 6)

In one embodiment, the present invention provides an antigenic epitope of TRPV1 comprising (or consisting of) an amino acid sequence of LVENGADVQAAAHGDF (SEQ ID NO:7), or a sequence substantially homologous thereto.

In another embodiment, the present invention provides an antigenic epitope of TRPV1 comprising (or consisting of) an amino acid sequence selected from the group consisting of:

DGPTGARLLSQ; (SEQ ID NO: 8)
and

DAEVFKSPAASGEK, (SEQ ID NO: 9)

or a sequence substantially homologous thereto.

In another embodiment, the present invention provides an antigenic epitope of TRPV1 comprising (or consisting of) an amino acid sequence selected from the group consisting of:

SQDSVAASTEKTL; (SEQ ID NO: 10)
and

SGSLKPEDAEVF, (SEQ ID NO: 11)

or a sequence substantially homologous thereto.

In one embodiment, the present invention provides an antigenic epitope of TRPV1 comprising (or consisting of) an amino acid selected from the group consisting of:

VSPVITIQRPGD; (SEQ ID NO: 12)

VSPVITIQRPGDGPTGA; (SEQ ID NO: 13)

LNLHDGQNTTIPLLL; (SEQ ID NO: 14)

YTDSYYKGQ (SEQ ID NO: 15)

SLPSESTSH (SEQ ID NO: 16)

EDPGNCEGVKR (SEQ ID NO: 17)

DRQSAQPEEVYLR; (SEQ ID NO: 18)
and

QSAQPEEVYLR, (SEQ ID NO: 19)

or a sequence substantially homologous thereto.

In some embodiments, the present invention provides an antigenic epitope of TRPV1 comprising an amino acid sequence as set out under the second heading (the heading marked with a double asterisk(**)) in each of Tables 2, 3, 4, 5, and 6 in the Example 3 herein, or a sequence substantially homologous thereto. Such peptides, digested using a higher proteolytic activity (or harsher or stronger proteolytic conditions) are generally less preferred than peptides digested using a lower proteolytic activity (or less harsh or weaker proteolytic conditions) (e.g. shorter time and/or lower concentration e.g. as set out under the first heading (the heading marked with a single asterisk (*) in each of Tables 2, 3, 4, 5, and 6), but may be of particular interest if they are, or are predicted to be, of functional importance to the protein. The peptides set out under the second headings in Tables 2, 3, 4, 5 and 6 (**) may be considered peptides that are digested late and the peptides set out under the first headings in Tables 2, 3, 4, 5 and 6 (*) may be considered peptides that are digested first.

In the context of the above antigenic epitopes of TRPV1, said substantially homologous sequence may be a sequence containing 1, 2, 3, 4, 5 or 6 (preferably 1, 2 or 3) amino acid substitutions or deletions compared to the given amino acid sequence, or is a sequence having at least 70% sequence identity to the given amino acid sequence, or is a sequence having at least 6 consecutive amino acids of the given amino acid sequence. Other examples of "substantially homologous" sequences are described elsewhere herein in relation to amino acid sequences that are "substantially homologous" to surface-exposed peptides and these examples of "substantially homologous" sequence are also applicable to the specific peptide sequences mentioned above. The specific peptide sequences mentioned above are surface-exposed peptide sequences.

In some embodiments, the present invention provides an antigenic epitope that comprises (or consists of) an elongated, truncated or cyclic version of a peptide sequence mentioned above (or a sequence substantially homologous thereto). Elongated, truncated and cyclic versions of peptides are discussed elsewhere herein in the context of elongated, truncated and cyclic surface-exposed peptides and that discussion is also applicable to the peptide sequences mentioned above. The specific peptide sequences mentioned above are surface-exposed peptide sequences.

In one embodiment, the present invention provides an antigenic epitope of TRPV2 comprising (or consisting of) an amino acid selected from the group consisting of:

FAPQIRVNLNYRKGTG; (SEQ ID NO: 20)

ASQPDPNRFDRDR (SEQ ID NO: 21)

LNLKDGVNACILPLL (SEQ ID NO: 22)

CTDDYYRGH (SEQ ID NO: 23)

LVENGANVHARACGRF (SEQ ID NO: 24)

EDPSGAGVPR; (SEQ ID NO: 25)
and

GASEENYVPVQLLQS, (SEQ ID NO: 26)

or a sequence substantially homologous thereto. Exemplary substantially homologous sequences are discussed elsewhere herein.

A further aspect of the embodiments relates to a conjugate configured to be used for production of antibodies. The conjugate comprises at least one antigenic epitope as defined above coupled to or admixed with a peptide carrier.

Thus, in one aspect, the invention provides a conjugate comprising an antigenic epitope of, or identified by (or produced by), the present invention. Conjugates may comprise an antigenic epitope and any distinct entity (i.e. any entity distinct from the antigenic epitope), for example a label or a peptide carrier. Conjugates typically comprise an antigenic epitope and a peptide carrier, wherein said antigenic epitope is coupled to, or admixed with, said peptide carrier.

In an embodiment, the peptide carrier is selected from the group consisting of keyhole limpet hemocyanin (KLH) and ovalbumin. The coupling can, for instance, be a covalent coupling or a disulphide bridge. In one embodiment keyhole limpet hemocyanin is a preferred peptide carrier. In some embodiments, an antigenic epitope may be provided with a cysteine residue at its N- or C-terminus (preferably N-terminus). Such a cysteine residue may facilitate coupling of the antigenic epitope to a peptide carrier (e.g. KLH).

Yet another aspect of the embodiments relates to the use of an antigenic epitope and/or a conjugate according to above for production of an antibody that specifically binds to a protein.

Still another aspect of the embodiments relates to a method for production of an antibody that specifically binds to a protein. The method comprises raising an antibody against an antigenic epitope and/or a conjugate according to above and isolating the antibody. Isolating the antibody may comprise isolating the antibody from the cell (e.g. host cell) in which it was generated or produced and/or from growth medium/supernatant.

In a particular embodiment, the method comprises exposing the protein to limited or restricted proteolysis by contacting the protein to at least one protease to form at least one digested, deconstructed or truncated version of the protein and at least one surface-exposed peptide. The method also comprises probing the at least one digested, deconstructed or truncated version of the protein in a functional assay that tests, checks or verifies at least one biological function of the protein. The method further comprises identifying an antigenic epitope in the protein as a surface-exposed peptide among the at least one surface-exposed peptide and present in a region of the protein involved in exerting the biological function of the protein as determined based on the functional assay. The method further comprises raising an antibody against the antigenic epitope and isolating the antibody.

Raising the antibody against the antigenic epitope can be performed according techniques known in the art including, for instance, the hybridoma technique, the phage-display technology, etc. as previously described herein.

A further aspect of the embodiments relates to an antibody against an antigenic epitope and/or a conjugate according to above. The antibody specifically binds to the protein.

Thus, in one aspect, the present invention provides an antibody generated by (or produced by) a method of the present invention.

In another aspect, the present invention provides an antibody against an antigenic epitope of the invention. Alternatively viewed, the present invention provides an antibody which binds to an antigenic epitope of the invention. Alternatively viewed, the present invention provides an antibody which specifically binds to an antigenic epitope of the invention.

By way of example, the invention provides an antibody against an antigenic epitope comprising (or consisting of) an amino acid sequence selected from the group consisting of LLSQDSVAASTEKTLRLYDRRS (SEQ ID NO:5) and GRHWKNFALVPLLRE (SEQ ID NO:6). In one embodiment, an antibody against an antigenic epitope comprising (or consisting of) the amino acid sequence LLSQDSVAASTEKTLRLYDRRS (SEQ ID NO:5) is an antagonistic (inhibitory) antibody against TRPV1, preferably having one or more of the functional properties described in the Example section for the antibody OTV1. This epitope corresponds to an amino acid sequence that is located in the N-terminal intracellular domain of TRPV1. In one embodiment, an antibody against an antigenic epitope comprising (or consisting of) the amino acid sequence GRHWKNFALVPLLRE (SEQ ID NO:6) is an agonistic antibody against TRPV1, preferably having one or more of the functional properties described in the Example section for the antibody OTV2. This epitope corresponds to an amino acid sequence that is located in the C-terminal intracellular domain of TRPV1.

In some embodiments, an antibody may be against an intracellular TRPV1 epitope (or domain). In some such embodiments, an antibody may be an antagonistic (inhibitory) antibody against an intracellular TRPV1 epitope (or domain). In other such embodiments, an antibody may be an agonistic antibody against an intracellular TRPV1 epitope (or domain).

In an embodiment, the binding of the antibody to the protein results in lack of or significantly altered biological function of the protein.

Thus, the antibody may be a functional antibody, e.g. an agonistic antibody or an antagonistic antibody (e.g. an antagonistic or agonistic antibody against TRPV1 or TRPV2). An antagonistic antibody is capable of binding to a protein and inhibiting or reducing a function of the protein. An agonistic antibody is capable of binding to a protein and potentiating or increasing a function of the protein. In the case of TRPV1 or TRPV2 (or any other ion channel) the function concerned may be ion transport activity. For example, the ability of an antibody to block (reduce) or enhance (increase) capsaicin or calmodulin binding may be assessed. Antibodies with such capabilities form preferred embodiments of the invention.

A related aspect of the embodiments defines an antibody according to above for use as a medicament.

The antibody against the antigenic epitope and/or conjugate may be obtained by immunizing an animal with one or more antigenic epitopes and/or one or more conjugates according to the embodiments. The immunized animal may be selected from the group comprising humans, mice, rats, rabbits, sheep, non-human primates, goat, horse and poultry.

The antibody according to the embodiments may also be obtained by in vitro immunization methods using one or more antigenic epitopes and/or one or more conjugates according to the embodiments.

The antibody according to the invention may be a polyclonal antibody or a monoclonal antibody.

The antibody may be a ligand, one or more fragments of an antibody, such as a Fab (Fragment Antigen Binding) fragment, a F(ab)'2 fragment (a fragment containing two Fab), a ScFv fragment (single-chain variable fragment), a diabody, a tetrabody, or an intact antibody.

An antibody of the invention is typically capable of binding (e.g. specifically binding) to the full-length version of the protein against which it is directed, for example the full-length version of the protein in its native form (e.g. in or on cells).

In some embodiments, the antibody is an antibody against one of the proteins (or types of proteins) described elsewhere herein.

Antibodies and antigenic epitopes may be isolated or purified. The term "isolated" or "purified" as used in this context refers to such molecules when isolated from, purified from, 30 or substantially free of their natural environment, e.g., isolated from or purified from an organism (if indeed they occur naturally), or refers to such molecules when produced by a technical process, i.e., includes recombinant and synthetically produced molecules. Thus, the term "isolated" or "purified" typically refers to an antibody or antigenic epitope substantially free of cellular material or other proteins from the source from which it is 35 derived. In some embodiments, such isolated or purified molecules are substantially free of culture medium when produced by recombinant techniques, or chemical precursors or other chemicals when chemically synthesized.

The functional effect of antibodies generated by the present invention on their target protein may be assessed, and a skilled person will readily be able to determine suitable assays to use, e.g. based on the nature of the target protein. For example, if the antibody is an antibody against TRPV1 (or any other ion channel), the functional effect of the antibody may be assessed e.g. using the electrophysiology and/or YO-PRO uptake assay described in Example 2 herein.

The methods of the invention can be used to generate an antibody which can then be isolated, produced or manufactured for various downstream uses. Thus, a further aspect of the present invention provides a method of producing or manufacturing and/or isolating an antibody.

When one or more antibodies have been generated, produced, selected, identified, isolated and/or purified using the methods of the invention, these antibodies, or a component, fragment, variant, or derivative thereof may be manufactured and if desired formulated with at least one pharmaceutically acceptable carrier or excipient. Such manufactured molecules, or components, fragments, variants, or derivatives thereof, are also encompassed by the present invention. Alternatively, these molecules may take the form of nucleic acids encoding said antibodies, which nucleic acids may in turn be incorporated into an appropriate expression vector and/or be contained in a suitable host cell. Thus, nucleic acid molecules encoding said antibodies, or expression vectors containing said nucleic acid molecules form further aspects of the invention.

Once a particular antibody, or a component, fragment, variant, or derivative thereof, has been generated or produced in accordance with the present invention, the expression vector encoding the antibody can readily be used (or adapted for use) to produce sufficient quantities of the molecule by expression in appropriate host cells or systems and isolating the antibodies from the host cell or system or from the growth medium or supernatant thereof, as appropriate. For polyclonal antibodies, antibodies may be isolated or purified from the serum of an immunized animal.

Thus, a yet further aspect of the invention provides a method of producing or manufacturing an antibody comprising the steps of generating or producing an antibody according to the methods of the invention as described above, manufacturing or producing said antibody, or a component, fragment, variant, or derivative thereof and optionally formulating said manufactured antibody with at least one pharmaceutically acceptable carrier or excipient.

Said variants or derivatives of an antibody include peptoid equivalents, molecules with a non-peptidic synthetic backbone and polypeptides related to or derived from the original identified polypeptide wherein the amino acid sequence has been modified by single or multiple amino acid substitutions, additions and/or deletions which may alternatively or additionally include the substitution with or addition of amino acids which have been chemically modified, e.g. by deglycosylation or glycosylation. Conveniently, such derivatives or variants may have at least 60, 70, 80, 90, 95 or 99% sequence identity to the original polypeptide from which they are derived.

As the invention relates to the generation of antibodies, said variants or derivatives further include the conversion of one format of antibody molecule into another format (e.g. conversion from Fab to scFv or vice versa, or the conversion between any format of antibody molecules described elsewhere herein, e.g. the conversion to any other type of antibody fragment as described herein), or the conversion of an antibody molecule to a particular class of antibody molecule (e.g. the conversion of an antibody molecule to IgG or a subclass thereof, e.g. IgG1 or IgG3, which are particularly suitable for therapeutic antibodies) or the humanization or the formation of a chimeric version of any antibody.

Said variants or derivatives further include the association of antibodies with further functional components which may for example be useful in the downstream applications of said antibodies. For example the antibodies may be associated with components which target them to a particular site in the body, or with detectable moieties useful for example in imaging or other diagnostic applications, or with a payload such as a radio-isotope, toxin or chemotherapeutic agent in the form of an immunoconjugate.

Clearly, the main requirement for such components, fragments, variants, or derivative binding partner molecules or target entities is that they retain their original functional activity in terms of binding ability or have improved functional activity.

The antibody molecules generated or produced or manufactured using the methods of the present invention may be used in any methods where antibodies specific to a target entity (for example antibodies specific to a particular antigen) are required. Thus, the antibodies can be used as molecular tools and a further aspect of the invention provides a reagent which comprises such antibodies as defined herein. In addition, such molecules can be used for in vivo therapeutic or prophylactic applications, in vivo or in vitro diagnostic or imaging applications, or in vitro assays.

Some particular embodiments of the invention are set out below:

1. A method of generating an antibody to a protein, said method comprising:
    (i) identifying an antigenic epitope in said protein by exposing the protein to limited or restricted proteolysis by contacting the protein with at least one protease to form at least one digested, deconstructed or truncated version of the protein and at least one surface-exposed peptide that is cleaved off from the protein by the action of said protease and generating an antigenic epitope based on said surface-exposed peptide; and
    (ii) raising an antibody against the antigenic epitope.

2. A method of generating an antibody to a protein, said method comprising:
    (i) exposing the protein to limited or restricted proteolysis by contacting the protein with at least one protease to form at least one digested, deconstructed or truncated version of the protein and at least one surface-exposed peptide that is cleaved off from the protein by the action of said protease; and
    (ii) identifying an antigenic epitope by identifying a surface-exposed epitope among the at least one surface-exposed peptide that is present in a region of the protein that results in a lack of, or significantly altered, biological function of the protein when the peptide is cleaved off or removed from the protein during the limited or restricted proteolysis; or selecting at least one target region within the protein based on bioinformatics and/or known data of biological function of the protein and identifying an antigenic epitope by identifying a surface-exposed epitope among the at least one surface-exposed peptide present in said at least one target region; and (iii) raising an antibody against the antigenic epitope.

3. The method of embodiment 1 or embodiment 2, wherein said at least one protease is used under conditions which result in at most 8 or at most 7 or at most 5 surface exposed peptides, or at most 8 or at most 7 or at most 5 unique surface exposed peptides, being cleaved off from the protein by the action of said protease in a sample of the proteolytically digested material, and optionally multiple samples are taken or run in sequence or in parallel, optionally at different periods of time and/or at different concentrations of said protease.

4. The method of any one of embodiments 1 to 3, wherein said at least one protease is used under conditions which result in at most 8 or at most 7 or at most 5 surface exposed peptides being cleaved off from the protein by the action of said protease.

5. The method of any one of embodiments 1-4, wherein the kinetic activity of said at least one protease is slowed down so much that said surface exposed peptides are cleaved off one at a time or at most a few at a time, for example at most 8 or at most 7 or at most 5 at a time in a sample, and optionally multiple samples are taken or run in sequence or in parallel.

6. The method of any one of embodiments 1-5, wherein said cleaved off surface-exposed peptides are ranked based on order of appearance after being contacted with said at least one protease, wherein the surface exposed peptides that are cleaved off first or at the lowest concentration of said protease are given a high rank and the surface exposed peptides that are cleaved off late or at the highest concentration of said protease are given a low rank, and optionally surface exposed peptides that are cleaved off in between may be ranked in order of their appearance.

7. The method of embodiment 6, wherein said method comprises picking a surface-exposed peptide having a high rank for antigenic epitope development and raising an antibody against said antigenic epitope.

8. The method of embodiment 6, wherein said method comprises picking a surface-exposed peptide having a high rank, constructing an antigenic epitope based on said surface-exposed peptide and raising an antibody against said antigenic epitope.

9. The method of embodiment 6, wherein said method comprises picking a surface-exposed peptide having a high rank, correlating said surface exposed-peptide with a defined biological property of the protein, constructing an antigenic epitope based on said surface-exposed peptide and raising an antibody against said antigenic epitope.

10. The method of any one of embodiments 1-9, wherein a single protease is used to digest, deconstruct and/or truncate said protein.

11. The method of any one of embodiments 1-9, wherein multiple proteases are used to digest, deconstruct and/or truncate said protein.

12. The method of embodiment 11, wherein the multiple proteases are used sequentially one at a time, are used in parallel, or are used in a single cocktail of multiple proteases.

13. The method of embodiment 11 or embodiment 12, wherein said multiple proteases are used to identify overlapping, complementary, or unique surface-exposed peptides.

14. The method of any one of embodiments 1-13, wherein said protease is selected from the group consisting of: trypsin, Arg-C proteinase, Asp-N endopeptidase, Clostripain, Glutamyl endopeptidase, Lys-C, Lys-N, Chymotrypsin, Proteinase K, Thermolysin, Pepsin, Caspase 1, Caspase 2, Caspase 3, Caspase 4, Caspase 5, Caspase 6, Caspase 7, Caspase 8, Caspase 9, Caspase 10, Enterokinase, Factor Xa, GranzymeB, Neutrophil elastase, Proline-endopeptidase, Staphylococcal peptidase I, and Thrombin.

15. The method of any one of embodiments 1-14, wherein said protease is trypsin.

16. The method of any one of embodiments 1-15, wherein said protein is a membrane protein that is present in a proteoliposome derived from cells.

17. The method of any one of embodiments 1-16, wherein said proteoliposome is immobilized in a flow cell to create a stationary phase of membrane proteins.

18. The method of any one of embodiments 1-15, wherein said protein is in a protein-containing lipid vesicle that is surface-bound or suspended in a solution.

19. The method of any one of embodiments 1-15, wherein said protein is in an intact cell that is surface-bound or suspended in a solution.

20. The method of any one of embodiments 1-15, wherein said protein is in a solution.

21. The method of any one of embodiments 1-20, wherein said protein is any protein of the human proteome.

22. The method of any one of embodiments 1-21, wherein said protein is a membrane bound protein, a soluble protein, an extracellular protein or an intracellular protein.

23. The method of any one of embodiments 1-22, wherein said protein is a membrane or a membrane associated protein.

24. The method of any one of embodiments 1-23, wherein said protein is an ion channel in the TRP superfamily.

25. The method of embodiment 24, wherein said protein is TRPV1 or TRPV2.

26. The method of any one of embodiments 1-23, wherein said protein is an excitatory amino acid receptor.

27. The method of embodiment 26, wherein said protein is the NMDA receptor or a G-protein.

28. The method of any one of embodiments 1-23, wherein said protein is an oncogenic protein.

29. The method of embodiment 28, wherein said protein is an oncogenic small GTPase selected from the group consisting of KRAS, NRAS and HRAS.

30. The method of any one of embodiments 1-23, wherein said protein is an immunomodulatory protein.

31. The method of embodiment 30, wherein said protein is selected from the group consisting of PD1, PDL1, CD40, OX40, VISTA, LAG-3, TIM-3, GITR and CD20.

32. The method of any one of embodiments 1-31, wherein said cleaved-off peptides are identified with mass spectrometry.

33. The method of embodiment 24, wherein said cleaved-off peptides are identified with LC-MS/MS.

34. The method of any one of embodiments 2-33, wherein said biological function is selected from the group consisting of capability of said protein to bind to a target such as a ligand or receptor, enzymatic activity of said protein, ion channel activity, transporter activity, and release such as insulin release and uptake machinery.

35. The method of any one of embodiments 1-34, wherein raising an antibody against an antigenic epitope is performed by hybridoma technology, phage display technology, or by immunizing an animal with said antigenic epitope.

36. The method according to any one of embodiments 1-35, wherein said antibody is monoclonal or polyclonal.

37. An antibody generated by the method of any one of embodiments 1-36.

38. An antigenic epitope of TRPV1 comprising an amino acid sequence selected from the group consisting of:

LLSQDSVAASTEK; (SEQ ID NO: 2)

LLSQDSVAASTEKTLR; (SEQ ID NO: 3)
and

QFSGSLKPEDAEVFKSPAASGEK (SEQ ID NO: 4)

or a sequence substantially homologous thereto,
wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

39. An antigenic epitope of TRPV1 comprising an amino acid sequence selected from the group consisting of:

LLSQDSVAASTEKTLRLYDRRS; (SEQ ID NO: 5)
and

GRHWKNFALVPLLRE. (SEQ ID NO: 6)

40. An antigenic epitope of TRPV1 comprising an amino acid sequence of LVENGADVQAAAHGDF (SEQ ID NO:7) or a sequence substantially homologous thereto, wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

41. An antigenic epitope of TRPV1 comprising an amino acid sequence selected from the group consisting of:

DGPTGARLLSQ; (SEQ ID NO: 8)
and

DAEVFKSPAASGEK. (SEQ ID NO: 9)

or a sequence substantially homologous thereto,
wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

42. An antigenic epitope of TRPV1 comprising an amino acid selected from the group consisting of:

SQDSVAASTEKTL; (SEQ ID NO: 10)
and

SGSLKPEDAEVF. (SEQ ID NO: 11)

or a sequence substantially homologous thereto,
wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

43. An antigenic epitope of TRPV1 comprising an amino acid selected from the group consisting of:

VSPVITIQRPGD; (SEQ ID NO: 12)

VSPVITIQRPGDGPTGA; (SEQ ID NO: 13)

LNLHDGQNTTIPLLL; (SEQ ID NO: 14)

YTDSYYKGQ; (SEQ ID NO: 15)

SLPSESTSH; (SEQ ID NO: 16)

EDPGNCEGVKR; (SEQ ID NO: 17)

DRQSAQPEEVYLR; (SEQ ID NO: 18)
and

QSAQPEEVYLR; (SEQ ID NO: 19)

or a sequence substantially homologous thereto,
wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

44. An antigenic epitope of TRPV2 comprising an amino acid selected from the group consisting of:

FAPQIRVNLNYRKGTG; (SEQ ID NO: 20)

ASQPDPNRFDRDR; (SEQ ID NO: 21)

LNLKDGVNACILPLL; (SEQ ID NO: 22)

CTDDYYRGH; (SEQ ID NO: 23)

LVENGANVHARACGRF; (SEQ ID NO: 24)

EDPSGAGVPR; (SEQ ID NO: 25)
and

-continued

GASEENYVPVQLLQS. (SEQ ID NO: 26)

or a sequence substantially homologous thereto,
wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

45. An antibody against an antigenic epitope of any one of embodiments 38-44.

As outlined above, we have developed a methodology for identification of surface-exposed antigenic epitopes that yields pharmacologically active antibodies using kinetically controlled proteolysis (i.e. limited or restricted proteolysis). Ideally, the proteolytic step (the limited or restricted proteolysis step) is done so slowly that the protease tears off a single or a few peptides at the time. First coming peptides, and especially their respective cut sites, are surface-exposed and easily accessible to an antibody, and are therefore generally favored over late coming peptides. These peptides can then be cross-correlated for sequence-based functional significance using curated bioinformatic data as well as functional assays performed on truncated proteins.

However, the present invention also provides methods which have improvements over methods described above which permit the further optimization of epitope design and/or the identification of further (additional) epitopes. Such an improved method is described below and is also referred to as method C.

This improved method is a multi-protease method which involves the use of multiple proteases on the same protein sequentially, in order to maximize the number of identified epitopes. This improved method utilizes two distinct proteolysis steps; a step of limited or restricted proteolysis, e.g. as described above, followed by a further proteolysis step (e.g. a non-limited proteolysis step) using a different protease or proteases (proteases with different specificity) from those used in the limited or restricted proteolysis step. Advantageously such methods can be used to identify protease accessible cut sites, but where peptides are not released and therefore not necessarily identified or detected by the methods based on a single limited proteolysis step described above. Thus, the method provides a means of identifying epitopes on native proteins at or near protease accessible cut sites, but where peptides are not released.

Overall, these improved methods should improve antibody development and yield novel 35 therapeutic and pharmacologically active antibodies to fight disease. Both intracellularly and extracellular-acting, pharmacologically active antibodies can be created using the methods described herein.

In the methods of the present invention, unlike many known techniques for the discovery of novel antibodies, the antibody can be designed from the outset to bind to a specific site and optionally perform a specific function, rather than being done blindly where the initial focus is generally on affinity, not functionality, and a subset of antibodies showing good binding characteristics are subsequently tested for pharmacological and biological effects.

When using limited proteolysis methods as described above as a tool to verify accessible regions for antibody binding, it relies on the release of peptides from a protein, i.e. it relies on the situation that proteases cut at two accessible sites surrounding a sequence of the right size for detection e.g. by mass spectrometry. The information achieved from such an experiment can provide verification of the accessibility of the two cut sites that were digested and caused the release of a peptide. However, some regions of interest in a protein may not fulfill these criteria. A protease may just cut a single site, creating a nick but not releasing a peptide. Release of peptide requires two cuts. If no peptide is released there is no evidence (e.g. MS-based evidence) of a binding event or proteolytic activity. The single cut remains undetected. Other reasons for non-detection may include glycosylation on a peptide, or that the peptide remains bound to the protein by ionic or covalent bonds. One way to circumvent this issue is to create antibodies against the sequences in which such a cut site resides. However, firstly you have to find a way to detect or identify these accessible cut sites from which peptides are not released. The present invention provides a way of doing this.

The inventors have developed additional and improved methods as, with the previous methods, several potential antibody-binding sites (epitopes) can be missed because some peptides are not released. This could occur for example if a protease only cleaves one of the two cleavage sites surrounding a certain amino acid sequence or if a protease cuts at one site and a peptide is not released for some other reason. In the improved method described below (method C), unique and novel antibody binding sites (epitopes) can be discovered, and in addition, yield new structural data for native, as well as partly digested proteins. This technology can thus provide comprehensive tools for probing protein structure and function.

Method C

In one aspect, the present invention provides a method of identifying an epitope on a protein that can be bound by an antibody, said method comprising:
 (i) performing limited or restricted proteolysis on said protein using a single first protease or a combination of first proteases;
 (ii) performing non-limited proteolysis or performing limited or restricted proteolysis on said protein using a single second protease or a combination of second proteases, wherein said second protease(s) are all different from the protease(s) used in step (i);
 (iii) analysing peptides which are released from said protein in step (ii) to identify peptides in which one end has been cut by a said first protease and the other end has been cut by a said second protease;
 (iv) probing one or more epitopes in a region of the protein containing or flanking a cut site for a said first protease as identified in step (iii) with one or more antibodies directed to said epitopes, thereby identifying one or more epitopes on the protein that can be bound by an antibody.

In one aspect, the present invention provides a method of identifying an epitope on a protein that can be bound by an antibody, said method comprising:
 (i) performing limited or restricted proteolysis on said protein using a single first protease or a combination of first proteases;
 (ii) performing non-limited proteolysis on said protein using a single second protease or a combination of second proteases, wherein said second protease(s) are all different from the protease(s) used in step (i);
 (iii) analysing peptides which are released from said protein in step (i) and step (ii) to identify peptides in which one end has been cut by a said first protease and the other end has been cut by a said second protease;

(iv) probing one or more epitopes in a region of the protein containing or flanking a cut site for a said first protease as identified in step (iii) with one or more antibodies directed to said epitopes, thereby identifying one or more epitopes on the protein that can be bound by an antibody.

In another aspect, the present invention provides a method of identifying an epitope on a protein that can be bound by an antibody, said method comprising:
(i) performing limited or restricted proteolysis on said protein using a single first protease or a combination of first proteases;
(ii) performing non-limited proteolysis or performing limited or restricted proteolysis on said protein using a single second protease or a combination of second proteases, wherein said second protease(s) are all different from the protease(s) used in step (i);
(iii) analysing peptides which are released from said protein in step (i) and step (ii) to identify peptides in which one end has been cut by a said first protease and the other end has been cut by a said second protease;
(iv) probing one or more epitopes in a region of the protein containing or flanking a cut site for a said first protease as identified in step (iii) with one or more antibodies directed to said epitopes, thereby identifying one or more epitopes on the protein that can be bound by an antibody.

Step (i)

The step of limited or restricted proteolysis (step (i) of Method C) can be carried out by any appropriate limited or restricted proteolysis method or step as described elsewhere herein. Such a step can also be referred to as limited or restricted protease digestion, or a step in 30 which a chosen protein is exposed to limited or restricted proteolysis. Put another way, the step of limited or restricted proteolysis is a proteolysis step (or a proteolytic digestion) which is not taken to or does not go to or is not carried out to completion. Thus, in this step a given protein may only be partially digested (or subject to partial proteolysis). This step is conveniently carried out by bringing the chosen protein (native protein) into contact with one 35 or more appropriate proteases under conditions which result in limited or restricted proteolysis (as described elsewhere herein). Under such conditions contacting the protein with the protease(s) results in the formation of at least one digested, deconstructed or truncated protein and at least one surface exposed peptide that is cleaved off from the protein by the action of said protease(s).

A single protease can be used for this step. Alternatively multiple proteases can be used together in combination (e.g. a cocktail of proteases can be used which are added to or brought into contact with the protein sample at the same time). In some embodiments use of a single protease is preferred. The one or more proteases used in this step are also referred to herein as "first protease(s)" or "protease(s) A". This is to distinguish these proteases from those used in step (ii) of the method (which are also referred to herein as "second protease(s)" or "protease(s) B"). The protease(s) used in step (ii) of the method will be different from those used in step (i), that is they will have a different specificity (a different substrate specificity).

Any appropriate protease may be used and suitable proteases that may be used in such a step of limited or restricted proteolysis are described elsewhere herein. In general preferred proteases are those which have robust or high specificity (e.g. do not have a tendency to digest amino acids outside their specificity) and/or which are well validated and characterized, e.g. in terms of specificity (in other words the amino acid sequence digested or cleaved by the protease is known and consistent).

One preferred group of proteases for use in the limited or restricted proteolysis step (i), (i.e. examples of first protease(s), protease(s) A, or proteases for the first digestion step), comprises one or more of Trypsin, Arg-C, Lys-C and Lys-N (sometimes referred to herein as Group 1 proteases).

Another preferred group of proteases for use in the limited or restricted proteolysis step (i), (i.e. examples of first protease(s), protease(s) A, or proteases for the first digestion step), comprises one or more of pepsin, chymotrypsin and Glu-C (sometimes referred to herein as Group 2 proteases).

In some embodiments the protease Asp-N can also be used in combination with either of these groups (sometimes referred to herein as Group 3 proteases).

In some embodiments, a protease selected from the group consisting of (or comprising) 35 trypsin, chymotrypsin and proteinase K is used in the limited or restricted proteolysis step (i).

As mentioned above, any of the limited or restricted proteolysis conditions described herein may be used in accordance with this aspect (Method C). In some embodiments, a concentration of protease of up to 2 µg/ml is used in step (i), for example about 0.5 µg/ml, µg/ml or about 2 µg/ml. In some such embodiments, the limited or restricted proteolysis is performed at room temperature.

In some embodiments, a concentration of protease of up to 5 µg/ml is used in step (i), for example about 1 µg/ml, about 2 µg/ml, about 3 µg/ml, about 4 µg/ml, or about 5 µg/ml. In some such embodiments, the limited or restricted proteolysis is performed at room temperature.

In some embodiments, the limited or restricted proteolysis step (i) is performed for up to 5 minutes (e.g. 1, 2, 3, 4 or 5 minutes). In some such embodiments, the limited or restricted proteolysis is performed at room temperature.

In some embodiments, the limited or restricted proteolysis step (i) is done with 2 µg/ml chymotrypsin for 5 minutes at room temperature.

In some embodiments, the limited or restricted proteolysis step (i) is done with 5 µg/ml trypsin for 5 minutes at room temperature.

In some embodiments, the limited or restricted proteolysis step (i) is done with 2 µg/ml proteinase K for 5 minutes at room temperature.

Step (ii)

In some preferred embodiments, step (ii) of the above method (method C) is a step of non-limited proteolysis and is performed on the protein which has been subjected to the limited or restricted proteolysis in step (i), i.e. steps (i) and (ii) are carried out sequentially on the same protein sample and the protein being analysed is subjected to sequential proteolysis.

After the limited proteolysis step (i) has been carried out, the protein will likely contain several additional sites for the protease(s) used in step (i) which have been digested (cleaved) during the limited proteolysis step but where the peptide remains attached (i.e. is not released), e.g. because there is not another site for the protease(s) close enough to this 35 site (the cut site), or because the peptide is retained on the protein by some other means, e.g. molecular interactions or forces, e.g. ionic bonds. Such cut sites represent sites that are exposed (accessible) protease sites in the native protein (e.g. are surface exposed sites) and are therefore of potential interest as forming part of a useful epitope to which antibodies can be targeted, but which may be missed using other methods involving limited proteolysis as described elsewhere herein, as a peptide with this cut site at one end will not be cleaved off from the protein by the action of the protease, and the cut site (and epitope corresponding thereto) will therefore not be identified (e.g. using MS). The second protease step (second digestion step), step (ii) of Method C can however be used to release these peptides and therefore allow the identification of the cut site and the exploration of epitopes in or around that cut site in the native protein using for example the subsequent steps of method C as described herein.

The second digestion step (step (ii)) may be carried out as a non-limited proteolysis step in order to retrieve maximum sequence coverage in the protein.

In some embodiments, step (ii) of the method (method C) is a proteolysis step that is a step of non-limited proteolysis (or non-restricted or non-limited proteolysis). This step is in direct contrast with the limited or restricted proteolysis carried out in step (i). For example, step (i) is generally carried out under mild proteolysis conditions with the aim to preserve the structure of the native protein as much as possible, whereas in step (ii) of the method the native structure of the protein does not need to be preserved (and indeed the integrity of the protein is often significantly impaired or the structure is not preserved), the aim in step (ii) being to digest (cleave) as many protease sites (and therefore release as many peptides) as possible, e.g. release a maximum number of peptides. The released peptides do however need to be analysed in step (iii) of the method, e.g. by mass spectrometry (MS). Thus, step (ii) is generally carried out in order to digest (cleave) as many protease sites and release as many detectable peptides (e.g. detectable by MS) as possible. In other words the aim is to cleave a maximum number of digestion sites resulting in the largest number of peptides that are still optimized for detection, e.g. MS detection (a digestion optimized for MS detection).

Thus, in some embodiments a step of non-limited (non-limiting) proteolysis as carried out in step (ii) of Method C is preferably one in which the proteolysis step is carried out to completion, or a step in which the given protein is completely digested (this is sometimes referred to as full proteolysis). However, if such a complete digestion would result in a significant number of peptides which are undetectable, e.g. by MS, for example because they are too short, then preferably the digestion would be stopped before that point was reached, for example when a maximum number or a significant number of peptides could still be detected, in other words a near complete digestion would take place.

Whether or not a proteolysis reaction could be taken to completion or near completion (e.g. to the stage at which as many detectable peptides as possible had been released) and whether or not an appropriate number of peptides were detectable could readily be determined by a person skilled in the art. This would for example depend on the detection capabilities of the instrument used, for example the mass range of the mass spectrometer. Typical peptide lengths for a mass spectrometer would be at least 4, 5, 6, 7 or 8 amino acids. Thus, the digestion (proteolysis) will preferably be stopped at a point when the majority (or maximum number) of the cleaved peptides are detectable, e.g. by mass spectrometry.

Appropriate conditions for the non-limited proteolysis step (ii) in comparison to the conditions used for the limited or restricted proteolysis of step (i) would readily be apparent to the skilled person. For example, whereas steps of limited or restricted proteolysis are carried out under sub-optimal/sub-optimum conditions for the appropriate protease(s), the step of non-limited proteolysis may be carried out under optimal (or closer to optimal or normal or recommended, e.g. manufacturer recommended, or standard) conditions for the appropriate protease(s).

Examples of appropriate conditions for step (ii) could be one or more (or all) of buffer, pH and temperature. Another appropriate condition could be concentration (e.g. high or saturated or maximum or optimal concentration) of protease. Thus, the non-limited proteolysis step could be accomplished by using one or more (or all) of optimal buffers for the given protease, optimal pH, and/or optimal digestion temperatures. When it comes to appropriate concentrations of protease(s) to be used in the non-limited proteolysis step (ii), then appropriate concentrations will generally correspond to concentrations which give rise to maximal or optimal or complete (full) or near-complete (if appropriate) protease activity, e.g. maximal or optimal or complete (or near complete, if appropriate) peptide cleavage (in contrast to concentrations which give sub-optimal activity which might be used for limited or restricted proteolysis).

Although a non-limited proteolysis step (step (ii)) may be performed using optimal conditions for a given protease, it is not always necessary to use optimal conditions for the protease in the non-limited proteolysis step. Sub-optimal conditions for a given protease may be used in a non-limited proteolysis step as long as an appropriate amount of protein cleavage still occurs (e.g. as described elsewhere herein). Purely by way of an example, if a protease is used in step (ii) at sub-optimal temperature (e.g. trypsin or chymotrypsin is used at <37° C. e.g. at room temperature) the proteolysis may still be considered to be non-limited if, for example, a high (or higher) concentration of protease is used and/or a long (or longer) incubation time is used. Typically, a high (or higher) concentration of protease in this context would be a concentration that is higher (e.g. significantly higher) than the concentration of the protease used in step (i). Typically, a long (or longer) incubation time in this context would be an incubation time that is longer (e.g. significantly longer) than the incubation time that is used in step (i). Purely by way of example, if a limited proteolysis reaction (step (i)) is performed using 5 µg/ml protease or less (e.g. 0.5, 1, 2, 3, 4 or 5 µg/ml) for 5 minutes or less at room temperature (e.g. 20-25° C.), then a step (ii) performed at room temperature with a higher concentration of protease (e.g. 20 µg/ml protease) and/or a longer incubation time (e.g. 1 hour) can be considered to be a step of non-limited proteolysis.

Some exemplary conditions for non-limited proteolysis with a particular protease(s) can thus be derived by comparison to appropriate conditions for limited or restricted proteolysis with that protease, e.g. as described elsewhere herein. For example, the optimum working temperature for trypsin is 37° C. and thus in embodiments which use trypsin for the step of non-limited proteolysis this temperature is preferred.

However, in some embodiments, the temperature used for the proteolysis in steps (i) and (ii) may be the same (e.g. room-temperature). In embodiments in which step (ii) is a non-limited proteolysis step and the same incubation temperature is used for both step (i) and step (ii), the conditions for the step (ii) proteolysis are typically adjusted relative to the conditions used for step (i) in order to achieve a harsher (or more complete or near-complete) proteolysis in step (ii) relative to step (i), e.g. by using a concentration of protease in step (ii) that is higher than the concentration of the protease used in step (i) and/or having a longer incubation time in step (ii) than the incubation time in step (i) (and/or adjusting any other condition in step (ii) in order to achieve a harsher (or more complete or near-complete) proteolysis in step (ii)).

In embodiments where for example a particular concentration of protease would be used for limited or restricted proteolysis then, for example, higher, preferably significantly higher, concentrations can be used for non-limited proteolysis, e.g. concentrations which are at least 2 fold, 3 fold, 4 fold, 5 fold, or 10 fold (or more) higher.

In some embodiments, when a given concentration of a first protease (or combination of first proteases) is used in a limited proteolysis step (step (i)), then a higher, preferably significantly higher, concentration of a second protease (or combination of second proteases) is used for non-limited proteolysis (step (ii)), e.g. concentrations which are at least 2 fold, 3 fold, 4 fold, 5 fold, or 10 fold (or more) higher. By way of an example, in some embodiments, if the concentration of the first protease (or combination of first proteases) used for limited or restricted proteolysis is 5 µg/ml or less, the concentration of the second protease (or combination of second proteases) used for non-limited proteolysis (step (ii)) may be 20 µg/ml or more.

In embodiments where for example a particular incubation time with a protease would be used for limited or restricted proteolysis then, for example, longer, preferably significantly longer, incubation times can be used if it is desired to use this protease for non-limited proteolysis, e.g. incubation times which are at least 2 fold, 3 fold, 4 fold, 5 fold, 10 fold, 20 fold (or more) longer. For example, where the incubation time of a particular protease for limited or restricted proteolysis would be in the order of minutes, then if it is desired to use this protease for non-limited proteolysis, then an incubation time of at least an hour (e.g. at least 1, 2, 3, 4 or 5 hours, or overnight) may be used. Alternatively the reaction can be allowed to continue until completion, e.g. until the activity of the protease is exhausted or until no further digestion is possible, or near-completion (if appropriate).

In some embodiments, when a given incubation time with a first protease (or combination of first proteases) is used in a limited proteolysis step (step (i)), then a longer, preferably significantly longer, incubation time with a second protease (or combination of second proteases) is used for non-limited proteolysis (step (ii)), e.g. incubation times which are at least 2 fold, 3 fold, 4 fold, 5 fold, or 10 fold (or more) longer. By way of an example, in some embodiments, if an incubation time with a first protease (or combination of first proteases) used for limited or restricted proteolysis is 5 minutes or less, then an incubation time of at least an hour (e.g. at least 1, 2, 3, 4 or 5 hours, or overnight) may be used for the non-limited proteolysis step with a second protease (or combination of second proteases) (step (ii)).

As it is preferred that the digestion (proteolysis) in step (ii) goes to completion or near-completion (or the maximum possible number of protease sites in the protein are cleaved/digested, e.g. in order to obtain a maximum or significant number of detectable peptides, e.g. MS detectable peptides), then, as discussed above, the time of incubation is an exemplary condition to ensure or perform non-limited proteolysis, e.g. by carrying out digestion for a long time, e.g. until the activity of the protease is exhausted or until no further digestion is possible, or until any further digestion is going to result in an increase, e.g. a measurable or significant increase, in the number or proportion of undetectable peptides (e.g. because they are too short to be detected, e.g. by MS).

At its broadest the non-limited proteolysis step (ii) can be regarded as a step in which more, preferably significantly more, proteolysis is carried out than in step (i) and appropriate proteases (and conditions) can be selected accordingly, providing that different protease(s), that is protease(s) with different specificities, are used in step (i) and step (ii). Alternatively viewed, a non-limited proteolysis step (ii) can be regarded as a step in which the proteolysis (or proteolysis conditions) is harsher (or stronger or more severe) than the proteolysis (or proteolysis conditions) used in step (i). Further alternatively viewed, the non-limited proteolysis step (ii) can be considered as proteolysis that is harsher (or stronger or more severe) relative to the proteolysis in step (i).

Thus, if a given protein has a certain number of potential cleavage points/sites for a given protease (i.e. sites recognizable by a given protease for cleavage), then under chosen limited or restricted proteolysis conditions the protease may cleave only at a subset of those cleavage sites, whereas if that protease was instead chosen for use under non-limited proteolysis conditions then such conditions would be chosen such that the protease may cleave at all (or significantly all) of those cleavage sites, or at increased numbers, preferably significantly increased numbers, of those cleavage sites than would have been cleaved under conditions for limited or restricted proteolysis.

Thus, if a given protein has a certain number of potential cleavage points/sites for a given protease A (i.e. sites recognizable by a given protease for cleavage), then under chosen limited or restricted proteolysis conditions the protease may cleave only at a subset of those cleavage sites, whereas under chosen non-limited proteolysis conditions in step (ii) with a different protease, protease B, the protease may cleave at all (or significantly all) of its cleavage sites, or at increased numbers, preferably significantly increased numbers, of its cleavage sites than would have been cleaved under conditions for limited or restricted proteolysis.

A step of in silico protease digestion or any other appropriate method or technique for predicting protease digestion of the protein may be used in order to predict the number of potential cleavage points/sites for a given protease. For example, the amino acid sequence of a protein could be reviewed by eye and the predicted cut sites (i.e. sites predicted to be cut by the protease) identified based on knowledge of a given protease's specificity and rules. Alternatively and conveniently a computer based method of prediction based on a given protease's specificity and rules is preferred. All these methods can take into account protease specificity and rules, e.g. trypsin will only cut at the C-terminal position of arginine or lysine. The rules and exceptions for digestion are available for most proteases, see for example Peptidecutter (Expasy, SIB Swiss Institute of Bioinformatics).

In some embodiments, non-limited proteolysis (step (ii)) is proteolysis (a proteolysis reaction) that results in (or achieves) the cleavage of at least 60%, or at least 65%, or at least 70%, or at least 75%, or at least 80%, or at least 85%, or at least 90% or at least 95% or at least 98% or at least 99% or even 100% of the sites (bonds) in the protein that are potentially cleavable (digestable) by the protease being used. Alternatively viewed, in some embodiments, non-limited proteolysis achieves at least 60%, or at least 65%, or at least 70%, or at least 75%, or at least 80%, or at least 85%, or at least 90% or at least 95% or at least 98% or at least 99% or even 100% proteolysis. The sites in a given protein that are potentially cleavable by the protease being used can be readily identified by a skilled person based on the knowledge of the protein sequence and the substrate specificity of the protease being used (e.g. by using a computer such as Peptidecutter (Expasy, SIB Swiss Institute of Bioinformatics). Typically, cleavage at all the potential sites in the linear amino acid sequence of the protein would represent the "100%" value (although the "100%" value could alternatively be set as the total number of potential sites in the protein that, if cleaved, would release (or yield) peptides that are of a length that is readily detectable by the instrument being used, e.g. the MS instrument being used). Alternatively, the "100%" value could be set as the number of potentially cleavable sites in the protein that are known to be (or are predicted to be e.g. by using protein modeling tools) in a region of the protein that is accessible to a protease (e.g. an extracellular part or domain of a protein, or e.g. not a part or region or domain of a protein that is within the cell membrane, or not a cysteine rich part of the protein or not a post-translationally modified part of the protein, or not a beta sheet).

The number (and location) of sites that are actually cleaved by the protease can also be readily determined by a skilled person (e.g. using mass spectrometry) and thus the percentage of potentially cleavable sites that are actually cleaved can be readily determined.

In some embodiments, non-limited proteolysis (step (ii)) is proteolysis (a proteolysis reaction) that achieves a level (or amount) of protein cleavage (e.g. as assessed by the release or cleaving off of peptides from the protein e.g. as determined by MS) that does not increase (or does not significantly increase) for example if a longer incubation (or reaction) time is used and/or if a higher concentration of the protease is used and/or if a temperature closer to the optimal temperature for the protease is used and/or if one or more other conditions that are closer to optimal conditions for the protease is used (e.g. one or more other conditions as described elsewhere herein).

Whereas limited or restricted proteolysis includes proteolysis done under limiting conditions (limiting kinetics) whereby the kinetics of protease activity is slowed down to the extent that peptides are cleaved off from the protein one at the time, or at most a few at a time, the step of non-limited proteolysis includes conditions where the kinetics of protease activity is not slowed down or reduced (or not significantly or measurably slowed down or reduced), or is optimized, normal or maximized. Thus, in some embodiments the kinetic activity of said protease in such non-limited proteolysis steps is such that multiple (preferably 8 or more) or as many as possible peptides are cleaved off at one time.

As mentioned above, at its broadest the non-limited proteolysis can be regarded as a step in which more (e.g. in terms of the number of cleavage sites), preferably significantly more, proteolysis is carried out than if the same protease was instead to be used in the limited proteolysis. Thus, in embodiments where the limited proteolysis conditions are set so that the kinetic activity of said protease is slowed down so much that said surface-exposed peptides are cleaved off one at a time or at most a few at a time, for example at most 8 (1, 2, 3, 4, 5, 6, 7 or 8) at a time (e.g. at most 8 peptides or at most 8 unique peptides in a sample, e.g. as described elsewhere herein), then if the same protease was instead to be used in step (ii) the conditions for non-limited proteolysis can be set such that more, and preferably significantly more, peptides are cleaved off at a time than under the limited proteolysis conditions (for example, more than 2, 3, 4, 5, 6, 7 or 8 at a time, as appropriate).

In preferred embodiments, the non-limited proteolysis reaction may go to completion such that the protein is exhausted of peptides that can be cleaved off by a given protease or until no further digestion is possible, or until any further digestion is going to result in an increase, e.g. a measurable or significant increase, in the number or proportion of undetectable peptides (e.g. because they are too short to be detected, e.g. by MS).

A single protease can be used for this non-limited proteolysis step (ii). Alternatively multiple proteases can be used. Such multiple proteases might be used together in combination (e.g. a cocktail of proteases can be used which are added to or brought into contact with the protein sample at the same time) or such multiple proteases might be used sequentially, e.g. one after the other (sequential use is preferred in some embodiments). The one or more proteases used in this step(s) are referred to herein as "second protease(s)" or "protease(s) B". This is to distinguish these proteases from those used in step (i) of the method (which are referred to herein as "first protease(s)" or "protease(s) A"). The protease(s) used in step (ii) of the method will be different from those used in step (i), that is they will have a different specificity.

Any appropriate protease may be used and suitable proteases that may be used in such a step of non-limited proteolysis would be well known to a person skilled in the art. In general, preferred proteases are those which have robust or high specificity (e.g. do not have a tendency to digest amino acids outside their specificity) and/or which are well validated and characterized, e.g. in terms of specificity (in other words the amino acid sequence digested or cleaved by the protease is known and consistent). Any of the proteases discussed elsewhere herein may be used for non-limited proteolysis.

One preferred group of proteases for use for the non-limited proteolysis step (ii) (i.e. examples of second protease(s), protease(s) B, or proteases for the second digestion step) comprises one or more of Trypsin, Arg-C, Lys-C and Lys-N(Group 1 proteases).

Another preferred group of proteases for use for the non-limited proteolysis step (ii) (i.e. examples of second protease(s), protease(s) B, or proteases for the second digestion step) comprises one or more of pepsin, chymotrypsin and Glu-C (Group 2 proteases).

In some embodiments the protease Asp-N can also be used in combination with either of these groups (Group 3 proteases).

Thus, for example, to carry out the methods of the invention, one or several proteases in combination from Group 1, can be used for limited proteolysis in the first step (step (i)), followed by one or several proteases in combination (or used sequentially) from Group 2, during the non-limited proteolysis in the second step (step (ii)).

Alternatively, one or several proteases in combination from Group 2, can be used for limited proteolysis in the first step (step (i)), followed by one or several proteases in combination (or used sequentially) from Group 1, during the non-limited proteolysis in the second step (step (ii)).

The Group 3 protease can optionally be combined either with Group 1 or Group 2.

In some embodiments, non-limited proteolysis may be considered a proteolytic step that is performed under one or more of the conditions described herein in connection with non-limited proteolysis.

As mentioned above, any of the non-limited proteolysis conditions described herein may be used in accordance with this aspect (Method C). In some embodiments, a concentration of protease (e.g. trypsin or chymotrypsin) of about 20 µg/ml is used in step (ii). In some such embodiments, the limited or restricted proteolysis is performed at room temperature.

In some embodiments, the non-limited proteolysis step (ii) is performed for about 1 hour. In some such embodiments, the limited or restricted proteolysis is performed at room temperature.

In some embodiments, the non-limited proteolysis step (ii) is done with 20 µg/ml 25 chymotrypsin for 1 hour minutes at room temperature.

In some embodiments, the non-limited proteolysis step (ii) is done with 20 µg/ml trypsin for 1 hour at room temperature.

Purely by way of illustration a specific example of appropriate proteases and conditions might be:

Step (i): Limited proteolysis with chymotrypsin—5 µg/ml, 5 min, buffer: e.g. 100 mM NH4HCO3, pH 8.0, 21° C.

Step (ii): Non-limited proteolysis with trypsin—20 µg/ml, 2 h, buffer: e.g. 100 mM NH4HCO3, pH 8.0, 37° C.

By way of another illustration, a specific example of appropriate proteases and conditions might be:

Step (i): Limited proteolysis with chymotrypsin—2 µg/ml, 5 min, room temperature, buffer: e.g. Tris-HCl 100 mM and $CaCl_2$ 10 mM, pH 8.0.

Step (ii): Non-limited proteolysis with trypsin—20 µg/ml, 1 h, room temperature, buffer: e.g. 100 mM ammonium bicarbonate, pH 8.

By way of another illustration, a specific example of appropriate proteases and conditions might be:

Step (i): Limited proteolysis with trypsin—5 µg/ml, 5 min, room temperature, buffer: e.g. 100 mM ammonium bicarbonate, pH 8.

Step (ii): Limited proteolysis with chymotrypsin—20 µg/ml, 5 min, room temperature, buffer: e.g. Tris-HCl 100 mM and $CaCl_2$ 10 mM, pH 8.0.

By way of another illustration, a specific example of appropriate proteases and conditions might be:

Step (i): Limited proteolysis with Proteinase K—2 µg/ml, 5 min, room temperature, buffer: e.g. Tris-HCl 100 mM and $CaCl_2$ 10 mM, pH 8.0.

Step (ii): Non-limited proteolysis with trypsin—20 µg/ml, 1 h, room temperature, buffer: e.g.

100 mM ammonium bicarbonate, pH 8.

It can be seen that the same protease(s) can be appropriate for use in either of the limited proteolysis step (i) or the non-limited proteolysis step (ii). A key point in carrying out some embodiments of this method (method C) is that the conditions under which the protein is exposed to the protease(s) are selected accordingly, depending on the protease(s) used, to achieve either limited or non-limited proteolysis. It is also important for these methods that different proteases (proteases with different specificities) are used for the two steps. By protease with a different specificity it is meant that the protease digests or cleaves at a different amino acid sequence.

Using multiple proteases as described herein includes, but is not limited to, using 2, 3, 4, 5 different proteases.

In some embodiments of the method only two different proteases are used; a single protease in step (i) and a different protease in step (ii). In some embodiments of the method only two proteolysis steps are carried out (one proteolysis step (i) and one proteolysis step (ii)).

In some embodiments of this method (Method C) in which in step (ii) non-limited proteolysis is performed, said method further comprises, subsequent to step (i), but prior to step (ii), an additional step (e.g. one or more steps) of performing limited or restricted proteolysis on said protein using said single second protease or a combination of second proteases that is used (to be used) in step (ii). Such a method may comprise a step of analysing peptides which are released from said protein in the additional limited proteolysis step that is performed prior to step (ii) and optionally also analysing peptides which are released from said protein in step (i) and/or step (ii) to identify peptides in which one end has been cut by a said first protease and the other end has been cut by a said second protease. Probing one or more epitopes in a region of the protein containing or flanking said identified cut site for a said first protease with one or more antibodies directed to said epitopes, thereby identifying one or more epitopes on the protein that can be bound by an antibody can also be performed. Without wishing to be bound by theory, it is believed that the inclusion of such an additional step of limited or restricted proteolysis using the second protease or combination of second proteases that is used (to be used) in step (ii) may be beneficial as fewer peptides would typically be released in a such an additional limited proteolysis step relative to the number of peptides released in the non-limited proteolysis step (ii), and thus peptides in which one end has been cut by a said first protease and the other end has been cut by a said second protease would be easier to detect (e.g. by MS) after the additional limited proteolysis step than after step (ii) as there would be less "noise" due to the reduced number peptides released in which both ends have been cut by the second protease.

The skilled person in the art would be well equipped to select appropriate proteases for use in the various steps of the method. In general, preferred proteases are those which have robust or high specificity (e.g. do not have a tendency to digest amino acids outside their specificity) and/or which are well validated and characterized, e.g. in terms of specificity (in other words the amino acid sequence digested or cleaved by the protease is known and consistent). As described elsewhere herein, one of the main criteria is that the protease(s) used in step (i) have different specificities, e.g. in terms of the amino acid sequence digested/cleaved, from the protease(s) used in step (ii).

The proteases of Groups 1, 2 and 3 as described above are preferred for this reason (e.g. robust and high and reliable specificity) and are put into the same group because they digest after a subset of one or more amino acids. A group of proteases can thus be put together (selected) based on the property of digesting at a single or relatively small group (sub-set) of amino acids (e.g. 1, 2, 3, 4 or 5 amino acids, e.g. up to 2, 3, 4 or 5 amino acids). Thus the Group 1 proteases all digest after arginine and/or lysine. The proteases in group 2 digest after tyrosine, tryptophan, phenylalanine and/or leucine. This means that the two groups have a completely different specificity and e.g. all peptides with a cut after arginine can be assigned to being digested by Group 1 (and thus to being digested in whichever step of the method in which one or more of the Group 1 proteases is used). The groups could be divided even further, e.g. Group 1 could be divided into groups of proteases which digest after arginine (i.e. a single amino acid) and a different group which digests after lysine. Thus, alternative and appropriate single proteases or groups of proteases can of course be provided or selected by a skilled person in the art if desired.

In order to increase the prospects that the maximum number of protease sites in the protein are cleaved (or to further increase the sequence coverage by the method), an additional denaturation step can optionally be carried out.

Such a denaturation step can be carried out before (prior), at the same time (during), or after the step of non-limited proteolysis. Appropriate conditions to be used to facilitate or induce denaturation of the protein would be well known to a person skilled in the art, for example, using appropriate denaturation agents, buffers, pH and/or temperatures. Denaturation conditions vary from protein to protein but commonly used agents are urea and guanidinium chloride, buffers with high or low salt concentrations and/or high or low pH, as well as temperatures above 40° C.

Although methods in which the first proteolysis step (step (i)) is a limited or restricted proteolysis step and the second proteolysis (step (ii)) is a non-limited proteolysis step are preferred, in some embodiments methods comprising two steps of limited proteolysis, i.e. step (i) and (ii) of the above described methods (method C) being steps of limited or restricted proteolysis, e.g. as described elsewhere herein, may be useful to generate peptides and identify epitopes.

In one aspect, the present invention provides a method of identifying an epitope on a protein that can be bound by an antibody, said method comprising:
  (i) performing limited or restricted proteolysis on said protein using a single first protease or a combination of first proteases;
  (ii) performing proteolysis on said protein using a single second protease or a combination of second proteases, wherein said second protease(s) are all different from the protease(s) used in step (i);
  (iii) analysing peptides which are released from said protein in step (i) and step (ii) to identify peptides in which one end has been cut by a said first protease and the other end has been cut by a said second protease;
  (iv) probing one or more epitopes in a region of the protein containing or flanking a cut site for a said first protease as identified in step (iii) with one or more antibodies directed to said epitopes, thereby identifying one or more epitopes on the protein that can be bound by an antibody.

Preferred features of other methods described herein can apply, mutatis mutandis, to this aspect of the invention.

In another aspect, the present invention provides a method of identifying an epitope on a protein that can be bound by an antibody, said method comprising:
  (i) performing proteolysis on said protein using a single first protease or a combination of first proteases;
  (ii) performing proteolysis on said protein using a single second protease or a combination of second proteases, wherein said second protease(s) are all different from the protease(s) used in step (i);
wherein the proteolysis performed in step (ii) is harsher (or more complete or more severe) than the proteolysis performed in step (i);
  (iii) analysing peptides which are released from said protein in step (i) and step (ii) to identify peptides in which one end has been cut by a said first protease and the other end has been cut by a said second protease;
  (iv) probing one or more epitopes in a region of the protein containing or flanking a cut site for a said first protease as identified in step (iii) with one or more antibodies directed to said epitopes, thereby identifying one or more epitopes on the protein that can be bound by an antibody.

The skilled person can readily determine proteolysis conditions for step (ii) that are harsher than the proteolysis conditions used in step (i), for example based on the discussion elsewhere herein. Preferred features of other methods described herein can apply, mutatis mutandis, to this aspect of the invention.

In some embodiments, the digested, released or cleaved peptides, e.g. the peptides cleaved off or released from the protein in step (i) and step (ii) are frozen (or otherwise appropriately stored) prior to performing step (iii).

Step (iii)

In step (iii) of the method, the digested, released or cleaved peptides, e.g. the peptides cleaved off or released from the protein in step (ii) (and optionally the peptides cleaved off or released from the protein in step (i)), are analysed, e.g. collected and analysed. Such analysis can be carried out by any appropriate technique but is conveniently and preferably carried out using mass spectrometry, e.g. as described elsewhere herein and in the Examples.

This step is used to identify peptides in which one end (e.g. the N-terminus or C-terminus) has been cut by a said first protease, i.e. a protease used in the limited proteolysis step (a protease A), and the other end (e.g. the C-terminus or N-terminus, as appropriate) has been cut by a said second protease, i.e. a protease used in the non-limited proteolysis step (a protease B). This then allows the identification of sites in the native protein which correspond to the end which has been cut by a said first protease, i.e. a protease used in the limited proteolysis step. These sites in the native protein are protease accessible sites which likely correspond to sites which are cut by the protease (cut sites) in the limited proteolysis step but from which peptides are not released. These sites also identify regions of the native protein which may contain one or more useful epitopes which can be bound by or targeted by antibodies (or other specific binding agents). Thus, the sites identified in part (iii) of the above method may be referred to as cut sites.

Thus, in this step it is not generally desired to identify peptides which have been cut at both ends by the same protease, e.g. cut at both ends by one of the proteases used in the limited proteolysis step or cut at both ends by one of the proteases used in the non-limited proteolysis step. However, in some embodiments it might be useful to identify peptides generated in step (ii) but not generated in step (i) which have been cut at both ends by one of the proteases used in the limited proteolysis step. Such peptides can correspond to protease accessible sites in the native protein which likely correspond to sites which are cut by the protease (cut sites) at two ends in the limited proteolysis step (i.e cut at both ends by a first protease, protease A, i.e. A-A peptides) but from which peptides are not released because they are retained on the protein by some other means, e.g. molecular interactions or forces, e.g. ionic bonds. These peptides (A-A peptides) can be released in step (ii) and can also identify regions of the native protein which may contain one or more useful epitopes which can be bound by or targeted by antibodies (or other specific binding agents). In some embodiments, the method further comprises in step (iii) (or alternatively comprises in step (iii)) the identification of peptides released in step (ii) but not released in step (i) which have been cut at both ends by one of the first proteases used in the limited proteolysis step (step (i)).

A separate analysis or identification step can be carried out after step (i) and step (ii) and in general this is preferred. However, a single analysis step can be carried out after step (ii) on the peptides which have been released from the protein in steps (i) and (ii). In practice, the step of limited proteolysis (step (i)) needs to be stopped before (step (ii)) (e.g. a non-limited proteolysis step (ii)) is started. Thus, the proteases used to carry out the limited proteolysis can be removed (e.g. by washing) before the proteases for step (ii) (e.g. a non-limited proteolysis step) are added. An example of a suitable wash buffer is described in the Example section herein. Use of a flow cell to carry out the proteolysis steps of the methods provides a convenient means for this.

Analysing or identifying peptides (peptide sequences) released from said protein by the protease digestion of step (ii) (and optionally peptides released from the protein by the protease digestion of step (i)) of the above method (Method C) in order to identify for example peptides in which one end has been cut by a said first protease (protease A) and the other end has been cut by a said second protease (protease B), in this case A-B or B-A peptides, may be done by any appropriate method or technique, for example by mass spectrometry (e.g. LC-MS/MS). Having identified peptides (peptide sequences) released (or cleaved) from said protein, the sites on the native protein at which one or more protease has cut said protein (cut sites) are readily identified, as knowledge of the peptide(s) sequences that are released from the protein by proteolysis (e.g. as identified by mass spectrometry), are informative of the cut sites, e.g. by mapping the sequences back to the sequence of the native protein. In this regard, the residues at the ends of the released peptide(s) (cleaved-off peptides) are informative of the cut site in the protein (e.g. in the native or full-length protein).

In a preferred embodiment, the digested peptides are collected and analyzed using mass spectrometry, e.g. as described elsewhere herein. Identifications of peptide spectra can be performed using search engines, such as, but not limited to, MASCOT. The search engine can be set to identify peptides based on the digestion rules for all proteases used and/or no specific protease. As a clarifying example, the digestion rules applied in MASCOT could specify a search for peptides with either a trypsin cut or a pepsin cut, if such a combination was used experimentally. Combining sequence data from all identified peptides in step (i) and step (ii), one can distinguish cut sites that were digested using limited proteolysis on the native protein but the peptides were not released or the peptide was still attached (these peptides would correspond to the peptides with ends corresponding to a first and second protease used in the method, e.g. A-B or B-A peptides, or sometimes A-A peptides as discussed above), from cut sites that were digested using limited proteolysis on the native protein but where the peptide was released/cleaved off from the native protein by the action of the protease in step (i) of the method (these peptides would generally correspond to the peptides with both ends corresponding to a first protease used in the limited proteolysis step in the method, A-A peptides, and would be detectable after step (i) of the method).

In some embodiments of methods of the invention, in step (iii) only the peptides which are released from said protein in (or after) step (ii) are analysed (e.g. the peptides which are released in (or after) step (i) are not analysed). However, in some embodiments step (iii) involves analysing peptides which are released from the protein in step (i) and step (ii).

In some methods of the invention, only peptides that are released from the protein in an additional step of limited proteolysis that is performed using said single second protease or a combination of second proteases subsequent to step (i), but prior to step (ii) (e.g. as described elsewhere herein) are analysed. In some methods of invention, peptides that are released from the protein in an additional step of limited proteolysis that is performed using said single second protease or a combination of second proteases subsequent to step (i), but prior to step (ii) (e.g. as described elsewhere herein) are analysed and peptides that are released from the protein in step (i) and/or step (ii) are analysed.

Step (iv)

Step (iv) of the method comprises the step of probing one or more epitopes in a region of the protein containing or flanking a cut site for a said first protease as identified in step (iii) with one or more antibodies directed to said epitopes, thereby identifying one or more epitopes on the protein that can be bound by an antibody. Viewed alternatively, step (iv) of the method comprises probing one or more epitopes in a region of the protein containing or flanking a cut site for a said first protease as identified in step (iii) with one or more antibodies, and identifying whether or not said one or more antibodies bind to said one or more epitopes, thereby identifying an epitope on a protein that can be bound by an antibody.

A "cut site" in accordance with step (iv) of the above method (Method C) is described above in relation to step (iii). In some embodiments, a "cut site" may be considered as a site (or position) in the amino acid sequence of the protein (e.g. in the native protein or full-length protein or wildtype protein or in situ protein or non-denatured protein) that corresponds to a site cut by the protease (cut site) in (step (i)) but from which a peptide is not released in step (i). Alternatively viewed, in some embodiments a "cut site" in step (iv) of the above method (Method C) may be considered as a site (or position) in the amino acid sequence of the protein (e.g. in the native protein or full-length protein or wildtype protein) that corresponds to the end of a peptide identified in step (iii) that was cut by the first protease.

Probing one or more (e.g. a plurality) of epitopes as described herein means that one or more epitopes (or potential epitopes) on a protein (e.g. a native or full length protein) are analysed (or assessed or investigated) for their ability to be bound by antibodies that have been generated against (or bind to) isolated epitopes that correspond to the epitope (or potential epitope) on the protein. In a preferred embodiment, a plurality (or array) of epitopes is probed.

In some embodiments, the method may further comprise a step (prior to step (iv)) of generating (or synthesizing) one or more (e.g. a plurality, e.g. 2 or more, 3 or more, 5 or more, 10 or more, 20 or more, 50 or more, e.g. up to 3, up to 4, up to 5, up to 10, up to 20 or up to 50) isolated epitopes having sequences that correspond to one or more epitopes (or sequences) on said protein that are in a region of the protein containing or flanking a cut site for a said first protease as identified in step (iii), and generating (raising) antibodies (e.g. polyclonal antibodies) that are directed to (bind to) said isolated epitopes. In a preferred embodiment, a plurality (or array) of epitopes is generated and a plurality (or array) of antibodies is generated. Such antibodies can then be used in step (iv) of the above method for probing one or more epitopes on said protein (e.g. in the native or full-length protein). Any appropriate method or technique for generating isolated epitopes or for generating antibodies (e.g. as described elsewhere herein) may be used and the skilled person will be familiar with these.

In some embodiments, the epitopes have different lengths and/or sequences. Thus, within a plurality (or group) of epitopes there can be epitopes having different lengths and/or sequences from each other. In other embodiments the epitopes have the same (or similar) lengths and usually different sequences. Thus, in some embodiments, within a plurality of (or group) of epitopes the epitopes have the same or similar length.

Epitopes may be of any appropriate length. In some embodiments, isolated epitopes are 7-8 amino acids in length or have a length as described elsewhere herein.

In preferred embodiments, epitopes contain (or overlap with or surround) a cut site. In other embodiments, epitopes flank a cut site.

Typically, the epitopes (or at least a portion of any given epitope) will be within 50 amino acids of a cut site (a cut site that is a cut site for a said first protease, protease A, as identified in step (iii), which is likely to be a protease accessible cut site but where peptides are not released), i.e. +50 to −50 amino acids relative to the cut site. Preferably, the epitopes (or at least a portion of any given epitope) will be within 20 amino acids of a cut site (a cut site that is a cut site for a said first protease as identified in step (iii)), i.e. +20 to −20 amino acids relative to the cut site, or within 10 amino acids of a cut site, i.e. +10 to −10 amino acids relative to the cut site, or within 5 amino acids of a cut site, i.e. +5 to −5 amino acids relative to the cut site.

In some embodiments, "in a region of the protein containing or flanking a cut site" can mean within 50 amino acids of a cut site, i.e. +50 to −50 amino acids relative to the cut site, preferably within 20 amino acids of a cut site, i.e. +20 to −20 amino acids relative to the cut site, or within 10 amino acids of a cut site, i.e. +10 to −10 amino acids relative to the cut site, or within 5 amino acids of a cut site, i.e. +5 to −5 amino acids relative to the cut site.

Figure 15:
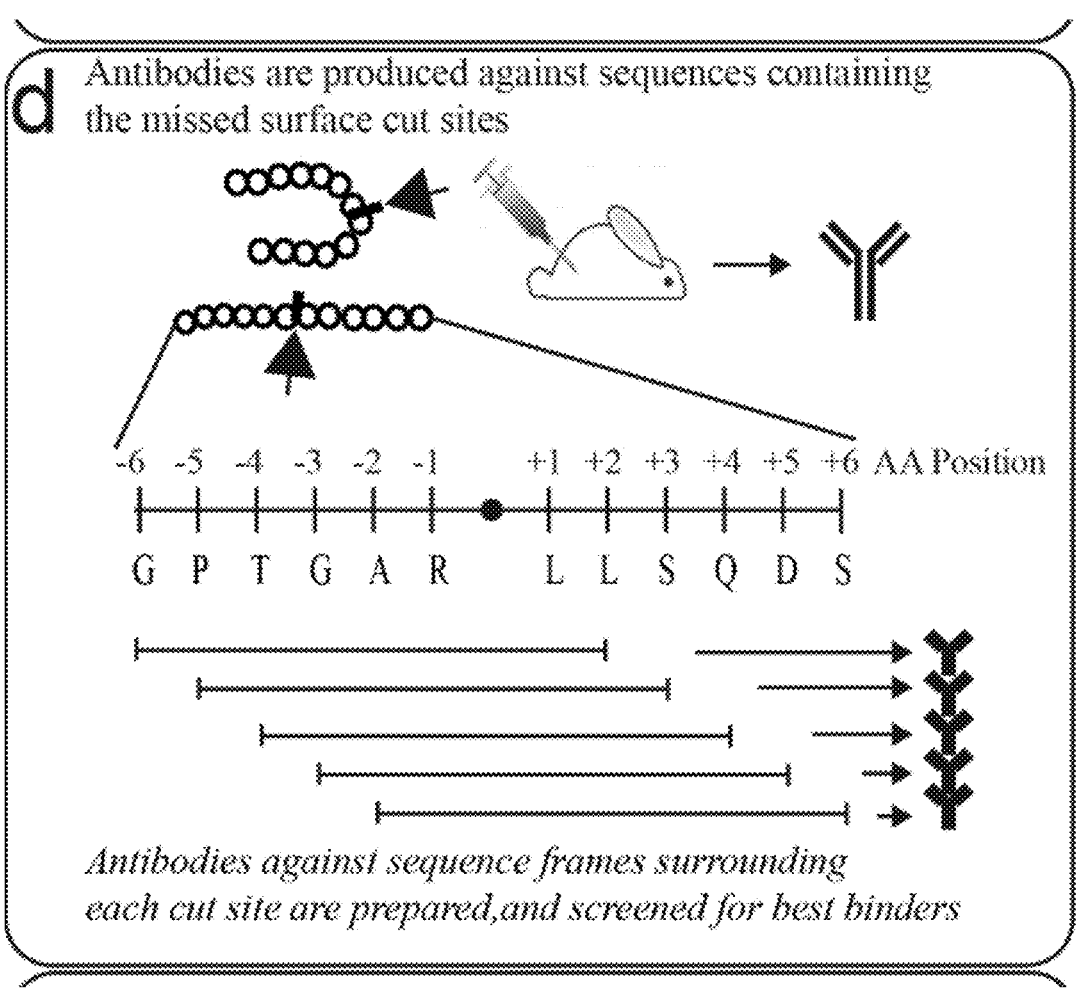

In some embodiments, a plurality of epitopes (more than one epitope) is a set (or group) of epitopes wherein the sequence of each epitope in the set is offset from another epitope in the set by one or a few (e.g. 1, 2 or 3), preferably one, amino acids. Put another way, in some embodiments, in a set (plurality) of epitopes each epitope sequence is shifted by one or a few (e.g. 1, 2 or 3), preferably one, amino acids to another epitope sequence in the set. Thus, the plurality of epitopes can be a nested set of epitopes, e.g. as illustrated in FIG. 15. Typically, such a nested set of epitopes will cover up to about 50 amino acids of the protein sequence in either direction (or in both directions) relative to (or surrounding) the cut site (a cut site for a said first protease as identified in step (iii), which is likely to be a protease accessible cut site but where peptides are not released). Preferably, such a nested set of epitopes will cover up to about 20 amino acids of the protein sequence in either direction (or in both directions) relative to (or surrounding) the cut site (a cut site for a said first protease as identified in step (iii)). In some embodiments, such a nested set of epitopes will cover up to about 6 amino acids of the protein sequence in either direction (or in both directions, preferably in both directions) relative to (or surrounding) the cut site (a cut site for a said first protease as identified in step (iii)).

When a nested set of epitopes is used, in preferred embodiments a significant number of the epitopes will contain the cut site, preferably substantially all of the epitopes in the nested set will contain the cut site, more preferably all of epitopes in the nested set will contain the cut site.

As described above, probing epitopes on the protein that contain or overlap with a cut site, or that are in a region that flanks a cut site may be done with antibodies directed to said epitopes (i.e. the antibodies act as probes). Indeed probing with antibodies (e.g. Fab fragments or other antibody fragments) is preferred. However, alternatively, other binding entities may be used as probes (e.g. other affinity probes or binding agents may be used). Affibodies are one example of affinity probe that may be used.

In one aspect, the invention provides an epitope (or antigenic epitope), e.g. an isolated epitope, identified by the method of identifying an epitope on a protein that can be bound by an antibody as described above (Method C). Exemplary and preferred features of epitopes are described elsewhere herein. In one aspect, the invention provides an antibody which binds (specifically binds) to such an epitope on a protein. Exemplary and preferred features of antibodies are described elsewhere herein. In some embodiments antibodies which bind in the vicinity of a cut site as described herein, e.g. within 5, 10, 20 or 50 amino acids of a cut site, are preferred. A person skilled in the art is familiar with methods or techniques for generating epitopes (e.g. isolated epitopes) and antibodies to given epitopes and any appropriate method may be used (e.g. as described elsewhere herein). Preferred types of antibodies are also described elsewhere herein. The methods of the invention (e.g. method C) thus include methods comprising an additional step in which an antibody is raised or generated against one or more of the epitopes identified. Thus, methods of generating an antibody (antibodies) to a protein are also provided. Such methods of antibody generation (or production or manufacture) may also comprise a step of purification of the antibody or protein product and/or formulating the antibody or product into a composition including at least one additional component, such as a pharmaceutically acceptable carrier or excipient.

In one aspect, the invention provides a conjugate that may be used for the generation (or production) of antibodies. A conjugate may comprise at least one epitope as defined herein coupled to or admixed with a peptide carrier. Other features of conjugates are described elsewhere herein.

In one aspect, the present invention provides a composition (e.g. a pharmaceutical composition) comprising an antibody or epitope of the invention. Such compositions typically comprise one or more diluents, excipients and/or buffers.

In one aspect, the present invention provides an antigenic epitope comprising (or consisting of) an amino acid sequence selected from the group consisting of (or comprising) any one of SEQ ID NOs: 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183 and 184, or a sequence substantially homologous thereto. SEQ ID NOs 82-184 are set forth in Table 9-14 herein. Sequences "substantially homologous thereto" are described elsewhere herein.

In some embodiments, the present invention provides an antigenic epitope comprising (or consisting of) an amino acid sequence selected from the group consisting of (or comprising) any one of SEQ ID NOs: 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183 and 184, or a sequence substantially homologous thereto, wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

In one aspect, the present invention provides an antigenic epitope comprising (or consisting of) an amino acid sequence selected from the group consisting of (or comprising) any one of SEQ ID NOs: 82, 88, 90, 94, 95, 96, 98, 99, 102, 104, 107, 110, 114, 115, 121, 122, 126, 130, 132, 137, 138, 139, 140, 141, 142, 143, 144, 145, 146, 147, 149, 150, 151, 152, 153, 154, 155, 156, 157, 158, 159, 163, 165, 167, 168, 169, 171, 173, 174, 175, 176, 178, 180, 181 and 182, or a sequence substantially homologous thereto. Sequences "substantially homologous thereto" are described elsewhere herein.

In some embodiments, the present invention provides an antigenic epitope comprising (or consisting of) an amino acid sequence selected from the group consisting of (or comprising) any one of SEQ ID NOs: 82, 88, 90, 94, 95, 96, 98, 99, 102, 104, 107, 110, 114, 115, 121, 122, 126, 130, 132, 137, 138, 139, 140, 141, 142, 143, 144, 145, 146, 147, 149, 150, 151, 152, 153, 154, 155, 156, 157, 158, 159, 163, 165, 167, 168, 169, 171, 173, 174, 175, 176, 178, 180, 181 and 182, or a sequence substantially homologous thereto, wherein said substantially homologous sequence is a sequence containing 1, 2 or 3 amino acid substitutions or deletions compared to the given amino acid sequence, or is a sequence having at least 70% sequence identity to the given amino acid sequence, or is a sequence having at least 6 consecutive amino acids of the given amino acid sequence.

In some embodiments, the present invention provides an antigenic epitope comprising (or consisting of) an amino acid sequence selected from the group consisting of (or comprising) SEQ ID NOs: 82, 83, 84, 85, 86, 87, 88, 89, 90, 91, 92, 93, 94, 95, 96, 97, 98, 99, 100, 101, 102, 103, 104, 105 and 106, or a sequence substantially homologous thereto.

In some embodiments, the present invention provides an antigenic epitope comprising (or consisting of) an amino acid sequence selected from the group consisting of (or comprising) SEQ ID NOs: 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, or a sequence substantially homologous thereto.

In some embodiments, the present invention provides an antigenic epitope comprising (or consisting of) an amino acid sequence selected from the group consisting of (or comprising) SEQ ID NOs: 137, 138, 139, 140, 141, 142, 143, 144, 145, 146, 147, 148, 149, 150, 151, 152, 153, 154 and 155, or a sequence substantially homologous thereto.

In some embodiments, the present invention provides an antigenic epitope comprising (or consisting of) an amino acid sequence selected from the group consisting of (or comprising) SEQ ID NOs: 156, 157, 158, 159, 160, 161, 162, 163, 164, 165, 166, 167, 168, 169, 170, 171, 172, 173, 174, 175, 176, 177, 178, 179, 180, 181, 182, 183 and 184, or a sequence substantially homologous thereto.

In one aspect, the invention provides an antibody that binds (specifically binds) to an epitope on a protein, wherein said epitope comprises (or consists of) an amino acid sequence selected from the group consisting of (or comprising) any one of SEQ ID NOs: 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183 and 184, or a sequence substantially homologous thereto. Preferred substantially homologous sequences are described elsewhere herein. Proteins in which such sequences are found (and thus to which certain antibodies of the invention may bind) are set forth in Tables 9-12 herein.

In one aspect, the invention provides an antibody that binds (specifically binds) to an epitope on protein, wherein said epitope comprises (or consists of) an amino acid sequence selected from the group consisting of (or comprising) any one of SEQ ID NOs: 82, 88, 90, 94, 95, 96, 98, 99, 102, 104, 107, 110, 114, 115, 121, 122, 126, 130, 132, 137, 138, 139, 140, 141, 142, 143, 144, 145, 146, 147, 149, 150, 151, 152, 153, 154, 155, 156, 157, 158, 159, 163, 165, 167, 168, 169, 171, 173, 174, 175, 176, 178, 180, 181 and 182, or a sequence substantially homologous thereto. Preferred substantially homologous sequences are described elsewhere herein. Proteins in which such sequences are found (and thus to which certain antibodies of the invention may bind) are set forth in Tables 9-12 herein.

In one aspect, the invention provides an antibody which binds to an epitope on a protein that contains or flanks (preferably contains) a cut site that is a cut site for a said first protease as identified in step (iii) (which is likely to be a protease accessible cut site but where peptides are not released).

Antibodies (e.g. a panel or an array or a large number of antibodies) targeting epitopes (preferably a plurality of epitopes) on the protein may be tested for their ability to bind the protein, for example to assess their binding affinity or other functional effect (e.g. as described elsewhere herein) on the protein. Antibodies may thus be screened to identify the best binders. Thus, particularly useful epitopes (e.g. for targeting by antibodies) may be identified, e.g. epitopes which are particularly suitable to be targeted by high affinity antibodies or the targeting of which results in a significant or measurable functional effect on the target protein (e.g. an antagonistic or agonistic effect). Accordingly, optimal epitopes (e.g. for targeting by antibodies) can be identified. Thus, alternatively viewed, the invention provides a method for optimizing epitope design or selecting an optimal epitope (e.g. for antibodies to be raised against or targeted to). The method can allow the determination of the optimal length and position of the epitope relative to the cut site.

Antibodies that bind to epitopes identified by Method C (or epitopes identified by Method C) may be used in therapy.

A more specific description to illustrate an embodiment of the invention and advantages is outlined below.

In step (i) with Protease A, the peptides cleaved off (peptides identified) would be peptides with cleavage sites for Protease A at both ends (peptides in which both ends have been cut by the protease A, A-A peptides). However, you would not obtain (identify) peptides where one end has been cut by Protease A but where the peptide has not been released (cleaved) for some reason, e.g. because there is not another site for the protease(s) close enough to this site (the cut site), or because the peptide is retained on the protein by some other means, e.g. molecular interactions or forces, e.g. ionic bonds.

In step (ii) with Protease B, the peptides cleaved off (peptides identified) would be peptides with cleavage sites for Protease B at both ends (peptides in which both ends have been cut by the protease B, B-B peptides), but also peptides with cleavage sites for protease B at one end and protease A at the other (peptides in which one end has been cut by the first protease and the other end has been cut by the second protease, B-A peptides, A-B peptides, or sometimes additional A-A peptides are also identified as described elsewhere herein). Studying the B-A (or A-B) peptides (or sometimes the additional A-A peptides) allows the identification (in step (iii)) of cut sites for protease A which would be otherwise undetected in step (i) because peptides were not physically cleaved off (released) from the protein.

These protease A cut sites identified in step (iii) are of interest because they are usually surface exposed in the native peptide, as they are generated in a limited proteolysis step as described elsewhere herein which can be designed to target surface exposed peptides and amino acid residues (e.g. they represent a preferred surface exposed peptide as described elsewhere herein, preferably a surface exposed peptide having a high rank, e.g. one which is cleaved off first or at the lowest concentration of protease or the most non-optimum or mild protease conditions, and would have been cleaved off other than for the fact that other factors did not allow the cleavage, e.g. another protease A site was not close enough). As such sites are on the surface of the native protein or are otherwise accessible, such sites may thus also represent a good part of the protein on which to base or target epitope design.

Importantly, as in some embodiments the protease B step (step (ii)) is carried out under non-limiting conditions, e.g. to completion (or near-completion), this means that all (or significantly all or a high number) of the B-A, A-B or additional A-A type peptides would be released therefore identifying all (or significantly all or high number) of protease A sites that were cut but not released in the limited proteolysis step (i). In this way an increased number of potentially useful sites, e.g. surface exposed sites, and therefore potentially useful epitopes can be identified as compared to if only a limited proteolysis step was done or if step (ii) was carried out under limited proteolysis conditions.

That said, a method comprising two steps of limited proteolysis, i.e. step (i) and (ii) of the above described methods (method C) being steps of limited or restricted proteolysis, e.g. as described elsewhere herein, may be useful to generate peptides and identify epitopes.

Preferred features of other methods described herein can apply, mutatis mutandis, to this aspect of the invention (Method C). For example, suitable proteins on which epitopes can be identified using Method C are as described elsewhere herein. In addition, suitable and preferred methodology, for example the use of mass spectrometry to analyse the cleaved peptides and use of flow cells, e.g. microfluidic cells or microfluidic platforms, and or proteoliposomes to carry out the proteolysis steps are described elsewhere herein. In addition, the steps of the method (method C) are generally carried out in vitro.

Method C may advantageously be used to identify protease-accessible/cut, but not released epitopes on the surface of proteins. The method uses in vitro protease digestion using several (2 or more) proteases sequentially in a step of limited proteolysis (using one or multiple proteases) followed by a step of non-limited proteolysis or a further step of limited proteolysis (using one or multiple proteases). The method may use a microfluidic platform as described elsewhere herein for digestion. Mass spectrometry (MS), preferably LS-MS/MS, may be used to identify peptides released by proteases from the target protein. Experimentally determined cut sites are elucidated from the peptide maps, e.g. as obtained by MS. Cut sites of interest, i.e. cut sites for a protease used in the limited proteolysis step but where peptides are not released, may be probed using antibodies against the sequences encompassing the cut sites (e.g. −20 to +20 amino acids surrounding the cut sites).

The purpose of this method is to identify antibody binding sites (epitopes) and/or elucidate protein structure using novel procedures where antibodies are used to identify protease-accessible/cut, but not released epitopes. The method is based on in vitro protease digestion using several (2 or more) proteases sequentially in a step of limited proteolysis (using one or multiple proteases) followed by a step of non-limited proteolysis or a further step of limited proteolysis (using one or multiple proteases). Microfluidic multiprotease digestion with MS-MS detection may be used. The procedures will enable discovery of unique and novel antibody binding sites (epitopes), and may yield new structural data for native, as well as partly digested proteins.

The steps of proteolysis are typically carried out in vitro. Thus, in vitro proteolysis experiments are performed. For membrane-associated proteins, proteoliposomes containing native protein can be digested within a microfluidic flow cell (LPI, Nanoxis Consulting AB). The flow cell technology enables flexible chemistry such as limited and non-limited proteolysis, to be performed on membrane proteins contained in a stationary phase (Jansson ET, Trkulja CL, Olofsson J, et al. Microfluidic flow cell for sequential digestion of immobilized proteoliposomes. Anal Chem. 2012; 84(13): 5582-5588), which can be subjected to several rounds of solutions and different types of chemical modulations, e.g. by enzymes. Thus, the steps of limited and non-limited proteolysis can be carried out sequentially. The step of limited proteolysis needs to be stopped before the non-limited proteolysis or further limited proteolysis step is started. Thus, the proteases used to carry out the limited proteolysis can be removed (e.g. by washing) before the proteases for the non-limited proteolysis step or further limited proteolysis step are added. Cell membranes can be turned inside out, and both intracellular and extracellular domains of membrane-spanning proteins can be interrogated directly. Soluble proteins can be subjected to limited and non-limited proteolysis using standard in-solution techniques.

Multiple proteases with varying specificities may be used, in sequential reactions, in order to cover as much sequence as possible. Limiting conditions already established, for example protease concentrations in the 2-5 µg/mL range and 5 minutes of digestion, may be used to restrict proteolysis to the protein surface. Released peptides may be identified mass spectrometry (e.g. by LC-MS/MS), preferably by using a high resolution mass spectrometer (e.g. Q Exactive, Thermo Fisher) and Mascot peptide/protein identification. With the peptide maps at hand we can then determine which cut sites were physically accessible by proteases. We then carry out the step of non-limited proteolysis as described elsewhere herein.

In order to pinpoint sites that are protease-accessible/cut, but not released, after the non-limited proteolysis step we can analyse the released peptides by mass spectrometry to identify peptides in which one end has been cut by one of the proteases used in the limited proteolysis step and the other end has been cut by a protease used in the non-limited proteolysis step (this can readily be done by looking at the amino acid sequence of the protein and the ends of the released peptides and knowing the specificity rules of the proteases used).

Peptide sequences, preferably 7-8 amino acids long, containing these sites may be synthesized and used to produce polyclonal antibodies (pAbs). The reason for the choice of length is to minimize the polyclonality of the pAbs by minimizing the target sequence but not so short that the sequence becomes poorly immunogenic.

Single amino acid frame shifts may be used to select linear sequences of this length within a set distance on each side of the cut site (e.g. 6 amino acids). These may then be used to create an array of sequence-targeting pAbs, which may subsequently be screened for binding to the native intact protein, using e.g. ELISA.

Preferred features of other methods described herein can apply, mutatis mutandis, to this aspect of the invention (method C).

In one aspect, the invention provides a method for identifying a surface exposed site (or surface accessible site e.g. accessible by a protease or an antibody) on a protein, said method comprising:
  (i) performing limited or restricted proteolysis on said protein using a single first protease or a combination of first proteases;
  (ii) performing non-limited proteolysis or performing limited or restricted proteolysis on said protein using a single second protease or a combination of second proteases, wherein said second protease(s) are all different from the protease(s) used in step (i);
  (iii) analysing peptides which are released from said protein in step (ii) to identify peptides in which one end has been cut by a said first protease and the other end has been cut by a said second protease;
wherein the end of (e.g. residue at the end of) a peptide identified in step (iii) that has been cut by a said first protease corresponds to a surface exposed site in the protein (native protein or wildtype protein or full-length protein) and thereby a surface exposed site on the protein is identified. Preferred features of other methods described herein can apply, mutatis mutandis, to this aspect of the invention Other features and advantages of the present invention are apparent from the examples below. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

In this example we describe a successful approach where we have discovered and developed a polyclonal antibody-OTV1-acting on the intracellular side of the human TRPV1 ion channel, based on the proposed invention and including methods. The antibody is pharmacologically active, and displays strong inhibitory action on the protein when stimulated with the agonist capsaicin. To the best of our knowledge, this is the first time an inhibitory antibody targeting the intracellular domains of TRPV1 is discovered. This proves that the concept has a high probability of working, and that even better and optimized antibodies could be identified if the starting matrix of epitopes originating from much richer multiprotease datasets would be available. The antibody was selected out of a number of hits from limited proteolysis and bioinformatic analyses. The antibody was the first selected and it showed strong evidence of efficacy. This is a significant advancement, and complimentary to current antibody identification efforts since no screening step is needed as it directly results in unique epitopes that can be targeted by a pharmacologically active antibody.

Figure 3:
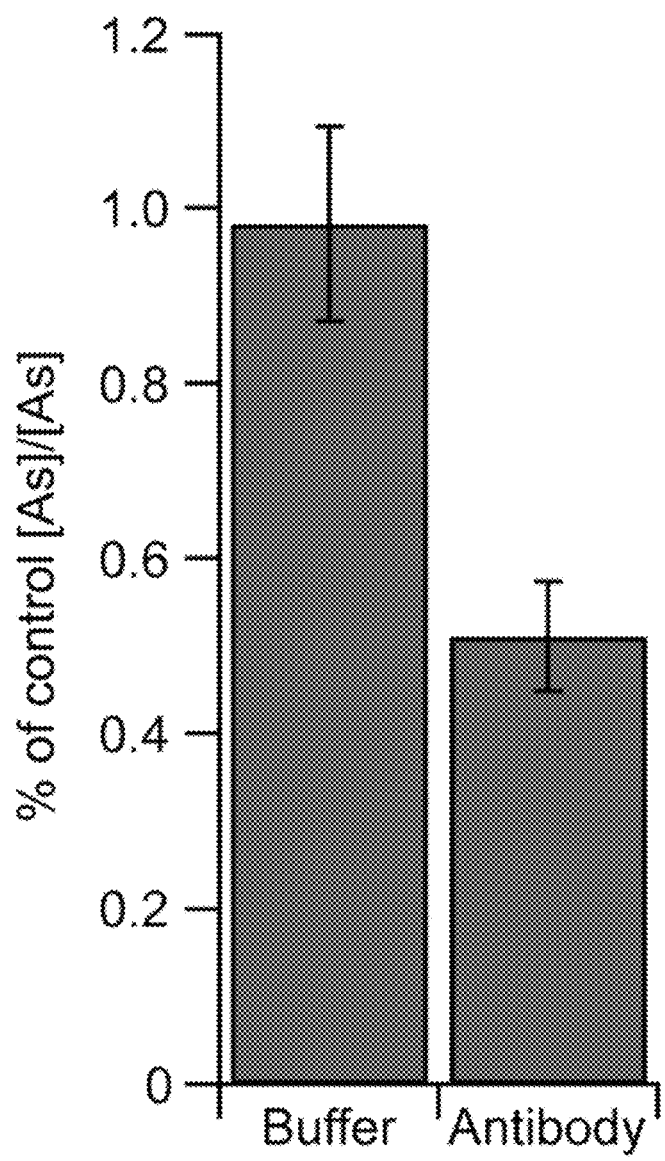

The targeted epitope region was chosen based on limited digestion of the target protein using optimized protocols in the LPI microfluidic platform, and was further optimized. A polyclonal antibody was generated by modifying the target peptide epitope with a cysteine-residue and link it to Keyhole Limpet Hemocyanin (KLH). The production of the specific antibody was performed by immunization of specific pathogen free (SPF) rabbits following injection of KLH with linked specific peptide. The antibodies were purified and subjected to an ELISA test according to standard protocols. An antibody titer against the linear epitope was performed with ELISA, resulting in a concentration of 0.25 µg/ml. The efficacy of the antibody against native TRPV1 was studied with inside-out patch clamp, where the intracellular side of TRPV1 could be exposed to antibody solution. Inside out recordings were performed using a microfluidic device for patch clamp recordings (Dynaflow, Cellectricon AB, Goteborg, Sweden). Current amplitudes were measured by exposing patches, containing several ion channels, to capsaicin, with and without antibody. Controls were exposed to 1 µM capsaicin for 30 s followed by buffer for 70 s and then again 1 µM capsaicin for 30 s. Antibody treated patches were exposed to 1 µM capsaicin for 30 s followed by 0.14 mg/ml antibody for 70 s and then 1 µM capsaicin together with 0.14 mg/ml antibody for 30 s. For all measurements, activity with antibody was compared to activity after exposure to only buffer, in order to exclude any effects of desensitization or potentiation. Current-time integrated areas were calculated and the ratio between the integrated areas for the second and first current were calculated and compared between treatments. A 50% decrease in current response were observed for cells treated with antibody compared to only buffer (FIG. 3). Statistical significance was calculated with Student's T-test ($p > 0.05$).

Example 2

The therapeutic mAb market is rapidly growing and is predicted to be worth about 125 billion USD in 2020. Novel mAbs are continuously reaching regulatory approvals, and presently, immunobased mAbs such as PD1 inhibitors, are much discussed since they are considerably improving the outcomes in certain types of difficult metastatic cancers. However, the discovery of novel antibodies for therapeutic purposes relies largely on screening, and is done blindly. The focus is on affinity, and a subset of antibodies showing good binding characteristics are subsequently tested for biological effects. The specifics around the binding interaction, antigen determinants, and mechanisms of action remain unknown.

We present a method that selects antigen epitopes based on a limited proteolytic kinetic challenge using a microfluidics approach and mass spectrometry. The proteolytic step is done so slowly that, after a protease challenge, the antigen tears off a single or a few peptides at the time. First coming peptides are easily accessible to a pAb or mAb, and are therefore favored over late coming peptides residing in regions of the protein that would be more difficult to reach. These peptides are then rank-ordered and cross-correlated for sequence-based functional significance using curated bioinformatic data. Highly-ranked peptides, coming off the target protein quickly, also having functional significance are used for epitope development, immunization and subsequent antibody generation. Also, the truncated proteins can be used for pharmacological testing. This method relies on sequence-based information, and is a pharmacological, mechanism-of-action based approach to antibody discovery, and can be used both for intracellular, circulating, and extracellular targets. We have used this method to develop two antibodies, one activating-addressing a calmodulin-binding sequence, and one inhibiting, addressing the capsaicin binding site in the N-terminus of the intracellular region of the human TRPV1 ion channel.

Two important parameters when developing therapeutic antibodies are binding affinity and biological efficacy. Antibodies are large proteins of approximately 150 kDa and binds primarily to antigenic sites located on the protein surface. Localization of amino acids in vicinity of the surface of native protein structures can guide the identification and prediction of these sites. We used limited proteolysis to probe surface-exposure and flexibility of a protein. It is a method where the activity of a protease is limited by control of the temperature, the concentration and/or the digestion time. Only flexible regions that can unfold locally and accommodate the protease, surface-exposed regions and regions with few local interactions such as hydrogen bonds and disulphide bridges, will be digested under such conditions. We used several proteases in tandem in order to maximize retrieval of structural information. Regions that are easily digested by several proteases should be located in the most exposed, most accessible regions of the protein and be of high suitability for further antibody development. Regions that are only digested by a single protease is likely located in a hidden region of the protein and less accessible. The physiochemical properties of the protease, able to reach and digest these regions, could potentially guide antibody development in such cases. We ranked digested peptides based on their ease of digestion depending on which parameters were used to limit the proteolysis. That could be the time point they were digested, which concentration or temperature that was used. Peptides digested from each protease were then correlated with each other, in order to find those peptides that originate from the most accessible regions of the protein.

During conventional antibody development, biological efficacy is generally tested after positive binding is confirmed between antibody and antigen. We believe that antibody development will benefit from an early mechanistic driven approach by focusing the immunization on accessible sites in or in vicinity of a biological active site rather than creating antibodies targeting all possible antigenic sites. This minimizes the screening procedures as well as the risk of optimizing antibodies that have a high binding affinity to regions distant from a biological active site. We wanted to find accessible epitopes that also had a functional importance for the target protein. This was done by comparing the ranked peptides from limited proteolysis with bioinformatics data.

We demonstrated our mechanism driven approach using the human TRPV1 ion channel as a model protein. TRPV1 is an ion channel sensitive to noxious stimuli such as low pH, high temperatures (T>42° C.), capsaicin, and several inflammatory mediators. The TRPV1 ion channel is mainly located in nociceptive neurons of the peripheral nervous system where it is arranged in a tetrameric conformation. Each of its four monomers consist of six transmembrane region with both the N- and C-termini facing the intracellular side of the plasma membrane. The pore region is comprised of the $5^{th}$ and $6^{th}$ transmembrane region. The intracellular part of TRPV1 holds many regulatory regions important for heat activation, sensitization and desensitization.

Epitope Generation

Figure 4:
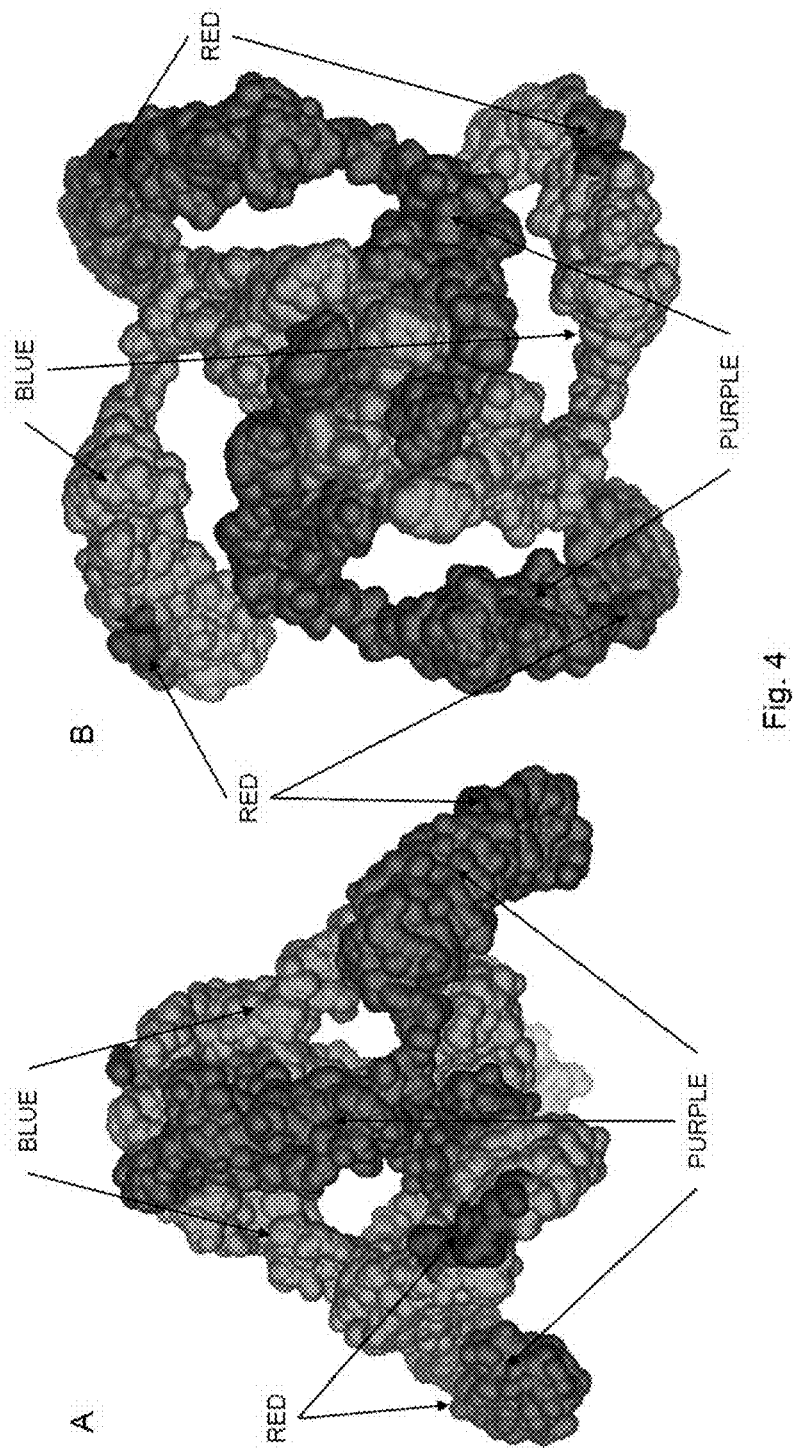

Proteoliposomes containing TRPV1 were derived from CHO cells and subjected to limited proteolysis within the LPI flow cell, using trypsin and Asp-N separately. The activity of the proteases were limited to the extent that only a few peptides were digested, by the use of room temperature and low concentrations. Digested peptides were then detected with liquid chromatography with tandem mass spectrometry (LC-MS/MS). Three peptides were detected after proteolysis with trypsin and one peptide after proteolysis with Asp-N. The peptides were compared to known functional data and several of the peptides correlated with functionally important regions as listed in Table 1. Two peptides were chosen for further antibody development, aa96-117 and aa785-799, named OTV1 and OTV2 respectively. Visualization of the epitopes within the TRPV1 structure can be seen in FIGS. 4 and 5. The peptide sequence for OTV1 includes arg115 (arg114 for rTRPV1) which have been shown to be important for activation with capsaicin or protons. Both proteases digested regions in the vicinity of this amino acid, increasing the possibility that this is an exposed region in the tertiary protein structure. The peptide sequence for OTV2 include the calmodulin binding site aa786-aa798 (aa785-aa797 for rTRPV1) and was digested by trypsin only. There are no digestion sites for Asp-N, which cleaves on the N-terminal side of Asp and Cys, in that part of TRPV1. Synthetic peptides of aa96-117 and aa785-799 were linked to limpet hemocyanin (KLH) and further used to produce polyclonal antibodies by immunization of rabbits following injection of the KLH linked peptides. The produced antibodies show tendencies to aggregate during freezing and with time in solution. Freshly thawed antibodies were, as a result, tip-sonicated prior to use, and all experiments were performed within 30 minutes of tip-sonication.

TABLE 1

Peptides digested with Asp-N and trypsin and their biological relevance

| Asp-N | | | Trypsin | | | |
|---|---|---|---|---|---|---|
| Sequence | Start | Stop | Sequence | Start | Stop | Interaction |
| DSVAASTEKTLRLY | 100 | 113 | LLSQDSVAASTEK | 96 | 108 | Capsaicin |
| | | | NFALVPLLR | 790 | 798 | Calmodulin |
| | | | QSAQPEEVYLR | 806 | 816 | |

Immunocytochemistry

Figure 6:
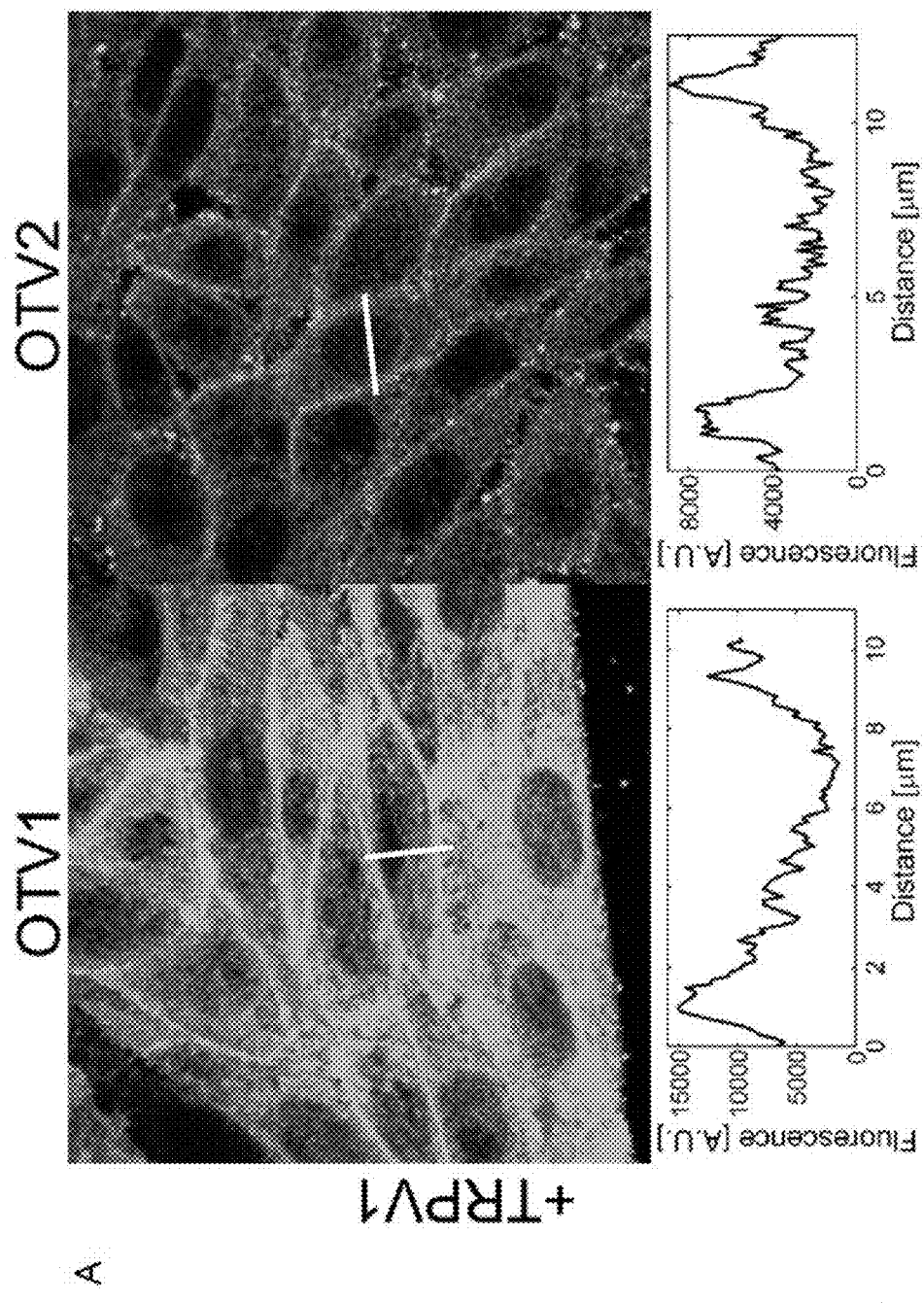
Figure 6:
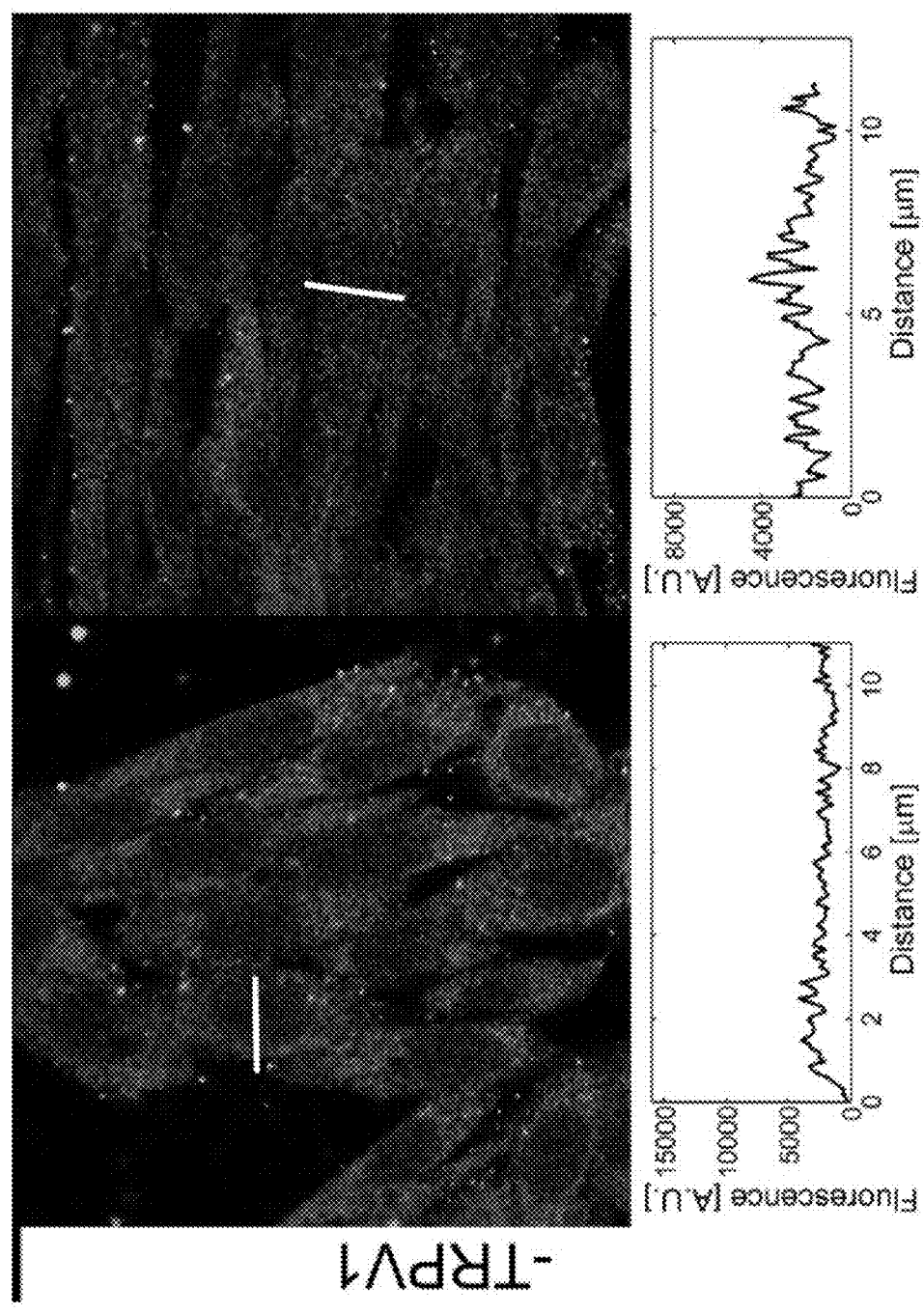

Immunocytochemistry was performed in order to visualize the antibody distribution within TRPV1 expressing CHO cells (FIG. 6). Non-induced cells served as a control for unspecific binding. Cells were fixed and stained with either OTV1 or OTV2 followed by a goat antirabbit Alexa 488 secondary antibody. A clear staining in the plasma membrane that was only visible in induced cells, was observed for both OTV1 and OTV2. Nonspecific binding of the secondary antibody was negligible (data not shown).

Electrophysiology

Figure 7:
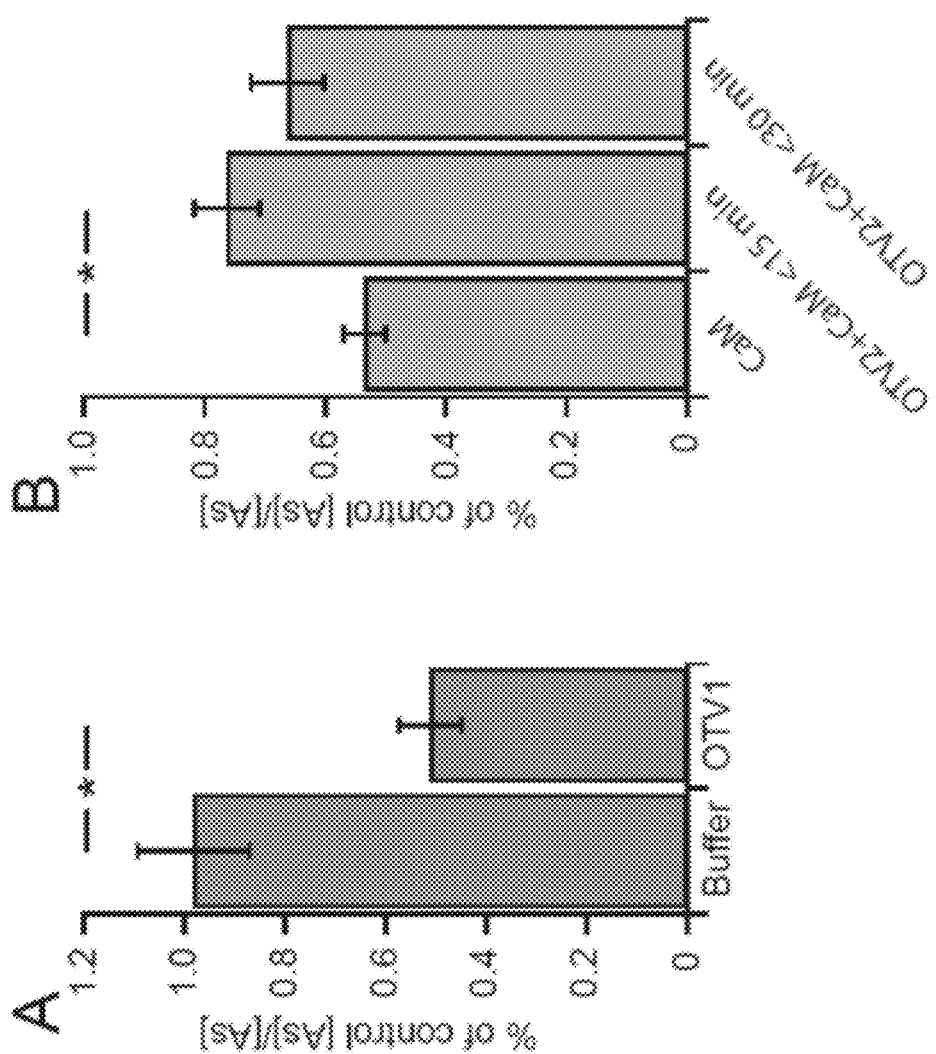

The functional effect of OTV1 on capsaicin induced TRPV1 activity as well as the effect of OTV2 on calmodulin/$Ca^{2+}$ dependent desensitization was evaluated using inside-out patch clamp recordings. Membrane patches, containing several ion channels, were excised from CHO cells, enabling antibody exposure to the intracellular region of TRPV1. For OTV1, TRPV1 was activated with capsaicin, then treated with OTV1, followed by activation with capsaicin in the presence of OTV1. Controls were activated with capsaicin, treated with buffer and activated with capsaicin again. A 50% decrease in capsaicin mediated currents was observed when comparing treatment with OTV1 to treatment with only buffer (FIG. 7). OTV2 was tested for its capability to interfere with calmodulin/$Ca^{2+}$ dependent desensitization. TRPV1 was activated with capsaicin, then treated with calmodulin, $Ca^{2+}$ and OTV2, followed by activation with capsaicin in the presence of calmodulin, $Ca^{2+}$ and OTV2. Controls were activated with capsaicin, treated with calmodulin and $Ca^{2+}$ and activated with capsaicin in the presence of calmodulin and $Ca^{2+}$. Calmodulin desensitize TRPV1 in the presence of calcium. Treatment with OTV2 reduced this effect with 45% (FIG. 7).

TRPV1 Mediated YO-PRO Uptake Assay

Figure 8:
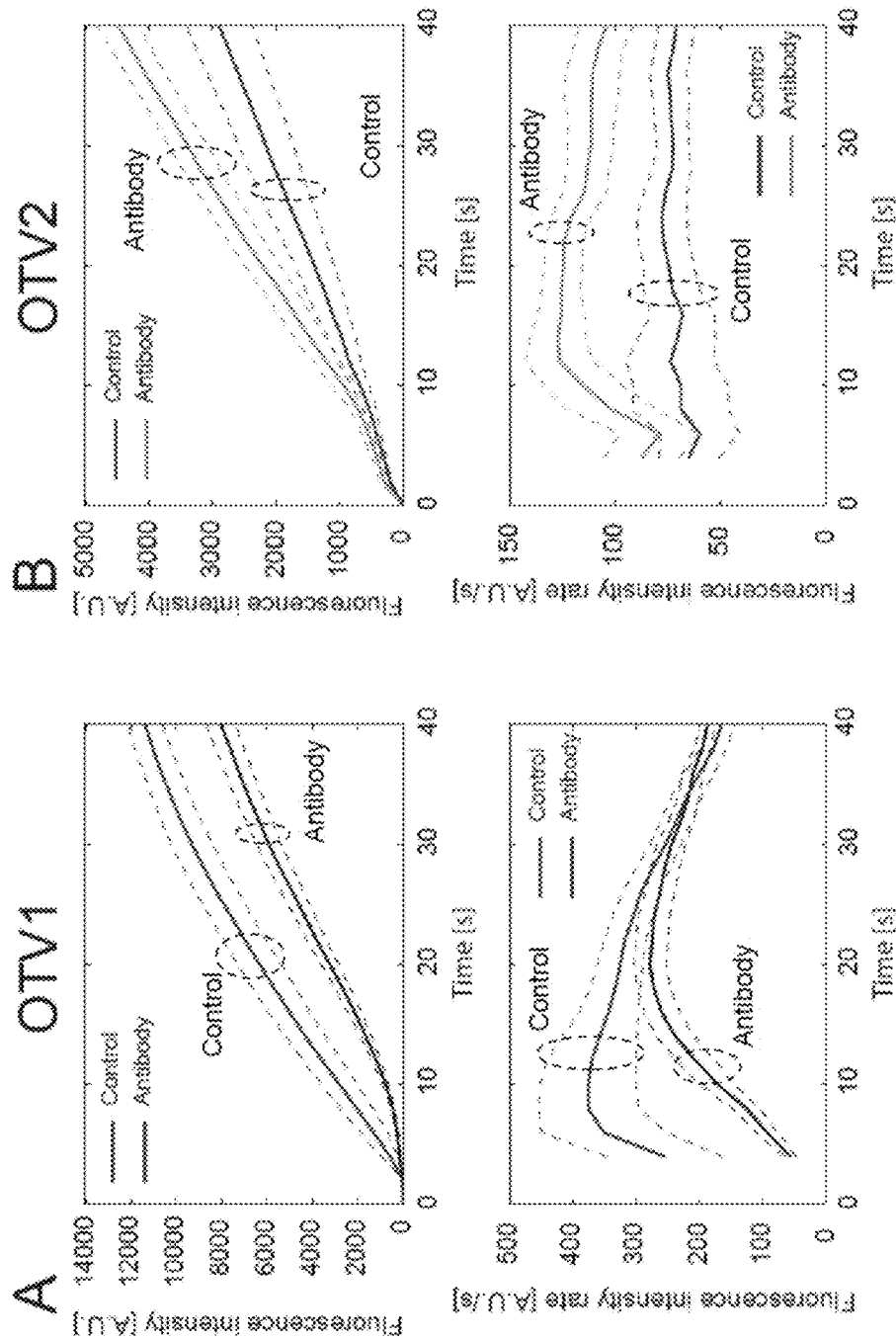
Figure 9:
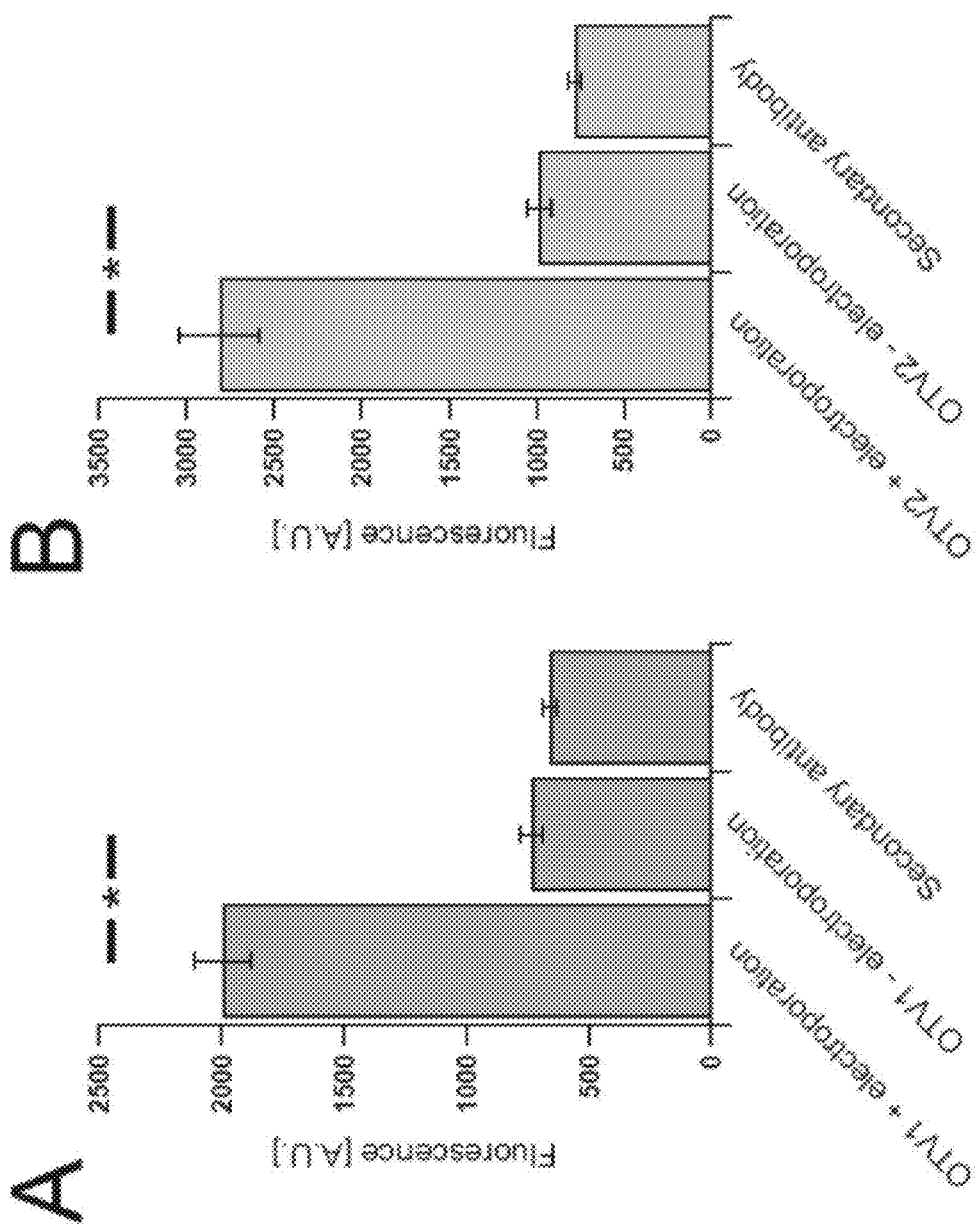

The efficacies of the antibodies within whole cells were tested using electroporation as a delivery method, followed by measurement of TRPV1 mediated YO-PRO uptake with laser scanning confocal microscopy. Cells were electroporated using a Neon transfection system (Life Technologies) in the presence of either OTV1, OTV2 or buffer. Cells electroporated with OTV1 or buffer were subjected to capsaicin and YO-PRO in PBS containing a calcium chelator. The intracellular increase in fluorescence due to TRPV1 mediated YO-PRO uptake was subsequently monitored. A 60% decrease in uptake rate for OTV1 treated cells could be observed during the initial 12 s of activation and the highest uptake rate for OTV1 treated cells were observed after 20 s compared to 8 s for the control (FIG. 8). Cells electroporated with OTV2 or buffer were subjected to capsaicin and YO-PRO in PBS containing calcium, relaying on desensitization through endogenous calmodulin triggered by the applied calcium. An 80% increase in uptake rate could be observed after 15 s of activation for OTV2 treated cells. Internalization of antibodies with electroporation was validated using immunocytochemistry (FIG. 9).

We have developed a microfluidic method for antibody generation that locates exposed and accessible antigenic sites in and/or in the vicinity of functionally important regions of a target protein. Accessible regions are probed, using kinetically restricted proteolysis, within the LPI flow cell. The target protein is held in its native state while the complexity of its environment can be carefully controlled, e.g. by allowing for co-factors to be present. This yields a better understanding of the accessibility of antigenic sites compared to binding assays using purified proteins. The method is well suited for transmembrane targets that otherwise are difficult to purify and use in binding assays without the need of detergents. Both intracellular and extracellular domains can be targeted using this approach.

Knowledge of the location of the antigenic site as well as its biological function is of great importance for prediction and evaluation of unspecific binding and cross-reactivity with other proteins. Epitopes located in very conserved regions could be excluded from the analysis of potential epitope candidates in order to minimize cross-reactivity.

The antibodies developed herein are polyclonals although not resulting from immunization with an entire protein. Our method is compatible with conventional protocols for production of monoclonal antibodies using hybridomas and subsequent screening procedures. Using polyclonal antibodies as a first step to experimentally validate biological efficacy for several promising epitope candidates followed by production of monoclonal antibodies using the best epitope/epitopes, and screening procedures for high binding affinity, combines the best of two worlds.

Verification of Antibody Internalization

The internalization of antibodies with electroporation was validated 24 hours after electroporation, with immunocytochemistry. Cells were electroporated in the presence of 0.14 mg/ml OTV1 or 0.27 mg/ml OTV2 in PBS. Electroporated cells were then cultured for 24 hours in glass bottom dishes (Willco wells). Two different controls were made. One set that weren't electroporated but were otherwise treated equally and subjected to the same antibody solutions, and another set that weren't subjected to OTV1 and OTV2. The latter were used to quantify unspecific binding of the secondary antibody. After 24 hours of cultivation, cells were washed carefully with PBS to remove any residual antibodies which could otherwise enter the cells during fixation. Cells were then fixed and permeabilized using the Image-iT® Fixation/permeabilization kit (Invitrogen). Fixed and permeabilized cells were incubated with a goat anti-rabbit Alexa 488 secondary antibody (Invitrogen) for 30 min in room temperature. Cells were visualized after a final washing step and fluorescence intensities were compared between electroporated cells, non electroporated cells and cells subjected to only secondary antibodies (FIG. 9). A clear difference in intensity values between electroporated and non electroporated cells was observed. Statistical analysis was performed with Students T-test and p<0.05 was considered as statistically significant. Low levels of primary antibodies were found in non electroporated cells which is likely residual antibodies that entered during fixation and permeabilization.

We herein presented a method for generation of high affinity, biologically active antibodies utilizing a combination of microfluidics and limited proteolysis. The method was validated using the human TRPV1 ion channel and two antibodies were developed. Both antibodies caused a predicted alteration in TRPV1 response based on the functional importance of their respective epitope region.

Materials and Methods

Chemicals

Cell culturing medium (DMEM/Ham's F12 with glutamine), fetal bovine serum, and Accutase were purchased from PAA. Zeocin, $Na_4BAPTA$, $K_4BAPTA$ and Goat anti rabbit Alexa 488 secondary antibody were purchased from Invitrogen. Sequencing grade modified trypsin and sequencing grade Asp-N were purchased from Promega. All other chemicals were purchased from Sigma. The following buffers were used: A: 300 mM NaCl, 10 mM Tris, pH 8.0, B: 20 mM $NH_4HCO_3$, pH 8.0. C: 140 mM NaCl, 5 mM KCl, 1 mM $MgCl_2$ 10 mM HEPES, 10 mM D-glucose, 10 mM $Na_4BAPTA$ pH 7.4, D: 140 mM NaCl, 2.7 mM KCl, 10 mM $Na_2HPO_4$, 10 mM $K_4BAPTA$ pH 7.2, E: 140 mM NaCl, 2.7 mM KCl, 10 mM $Na_2HPO_4$, pH 7.2. F: 140 mM NaCl, 2.7 mM KCl, 10 mM $Na2HPO_4$, pH 7.4. G: 120 mM KCl, 2 mM $MgCl_2$, 10 mM HEPES, 10 mM $K_4BAPTA$ pH 8.0

Cell Culture

Adherent Chinese hamster ovary (CHO) cells with a tetracycline regulated expression system (T-REx) were cultivated in medium (DMEM/F12 with glutamine) supplemented with 10% fetal bovine serum, Zeocin (350 µg/ml), and Blasticidin (5 µg/ml) in culture flasks or culture dishes (Nunc) with and without glass slides. 18-24 hours before use, the cells were incubated in medium (DMEM/F12 with glutamine) supplemented with 10% fetal bovine serum and Doxycycline (1 µg/ml) in order to induce expression of human TRPV1. The cell line was routinely tested for *mycoplasma* infection.

Proteoliposome Preparation

Proteoliposomes were prepared as previously elsewhere [1] in buffer A. Each proteoliposome preparation originated from several different culture flasks.

Digestion Protocols

Single digestions within the flow cell were conducted as described elsewhere [1]. 5 µg/ml Trypsin and 5 µg/mlAsp-N was dissolved in buffer G and B, respectively. Digestion within the flow cell with each protease was performed in room temperature for 5 min. Further digestion in the elutes was inhibited by addition of formic acid to a final concentration of 12%.

Liquid Chromatography with Tandem Mass Spectrometry

Peptide samples from digestions of CHO-proteoliposomes were analyzed at the Proteomics Core Facility at Gothenburg University, Goteborg, Sweden, as previously described [1]. All tandem mass spectra were searched by MASCOT (Matrix Science, London, UK) against UniProtKB release 2013_04, (Human, [*Homo sapiens*]) for digestion with trypsin and release 2015_06 (Human, [*Homo sapiens*]) for digestion with Asp-N. Thermo Proteome Discoverer v. 1.3 (Thermo Scientific) was used to validate MS/MS based peptide and protein identifications. A false discovery rate of 0.01 on peptide level were used and determined by searching a reversed database.

Antibody Development

Synthetic peptides of aa96-117 and aa785-799 with reference to the amino acid sequence of hTRPV1, including an additional cysteine residue on the N-terminal side, were synthesized and purified. The peptides were then linked by the cysteine residue to keyhole limpet hemocyanin (KLH) and then used to produce polyclonal antibodies by immunization of specific pathogen-free (SPF) rabbits following injection of the KLH linked peptides. The antibodies were purified and subjected to an ELISA test. Generation of both synthetic peptides and polyclonal antibodies were performed by Innovagen AB (Lund, Sweden).

Antibodies were used freshly thawed and within 30 min of tip-sonication. The antibodies were sonicated at 14% amplitude three times, interspaced with 1 min of resting, using a Vibra Cell VCX 600 from Sonics & Materials Inc. (Newtown, Conn., USA). Total sonication time were 40 s with 0.5 s pulse time and 0.5 s resting time in order to reduce heating by the probe.

Electrophysiology

Inside-out recordings were performed using a microfluidic device for patch clamp recordings (Dynaflow, Cellectricon AB, Goteborg, Sweden) together with a HEKA EPC10 (Heka Elektronik, Germany) patch clamp amplifier. Bath and pipette solutions contained buffer C. The patches were clamped at +60 mV and the current signals were recorded with a sampling frequency of 20 kHz and low pass filtered at 5 kHz.

For OTV1, current amplitudes were measured by exposing patches, containing several ion channels, to capsaicin, with and without antibody. Controls were exposed to 1 µM capsaicin in buffer D for 30 s, followed by buffer D for 70 s and then again 1 µM capsaicin in buffer D for 30 s. OTV1 treated patches were exposed to 1 µM capsaicin in buffer D for 30 s, followed by 0.14 mg/ml antibody in buffer D for 70 s and then 1 µM capsaicin together with 0.14 mg/ml antibody in buffer D for 30 s. For OTV2, current amplitudes were measured by exposing patches to capsaicin, with and without antibody and calmodulin/$Ca^{2+}$. Controls were exposed to 1 µM capsaicin in buffer E for 30 s, followed by exposure to 0.5 µM calmodulin and 50 µM $Ca^{2+}$ in buffer E for 70 s and then again 1 µM capsaicin in buffer E for 30 s. Antibody treated patches were exposed to 1 µM capsaicin in buffer E for 30 s, followed by 0.14 mg/ml antibody, 0.5 µM calmodulin and 50 µM $Ca^{2+}$ in buffer E for 70 s and then 1 µM capsaicin together with 0.14 mg/ml antibody, 0.5 µM calmodulin and 50 µM $Ca^{2+}$ in buffer E for 30 s. Measurements that shifted largely in seal resistance after treatment were excluded from further analysis.

Data Analysis Electrophysiology

For all measurements, activity after antibody treatment was compared to activity after exposure to only buffer, in order to exclude any effects of desensitization or potentiation resulting from recurring activations. For data containing current traces, current-time integrated areas were calculated using Fitmaster (HEKA Elektronik, Germany) and Matlab (Mathworks, MA, USA) for each activation with capsaicin between application and removal for OTV1 and between full activation (after 10 s) and removal for OTV2. The ratio between the integrated areas for the second and first current were calculated and compared between treatments. For OTV2, data points were grouped into two categories (<15 min after tip sonication and <30 min after tip-sonication) due to a time dependent decrease of effect.

Statistical analysis was performed with one-way analysis of variance in combination with Dunnett's post-hoc test and Students T-test where applicable. $p<0.05$ was considered as statistically significant. Data is presented as mean±SEM.

Electroporation

Cytosolic antibody delivery was performed using a Neon transfection system (Life Technologies). Adherent CHO cells were detached using accutase and washed with buffer F. 105 cells were pelleted and resuspended in either buffer F, 0.14 mg/ml OTV1 in buffer F or 0.27 mg/ml OTV2 in buffer F. 10 µl of cell/antibody suspension were pipetted using a Neon pipette tip and subjected to electroporation in the system pipette station. A protocol optimized for antibody delivery [5] were used, where the cells were exposed to 1550 V during 10 ms and for 3 pulses. Electroporated cells were transferred to glass bottom dishes (Willco wells)

Imaging

Antibody localization through immunocytochemistry and TRPV1 mediated YO-PRO uptake was measured using region of interest (ROI) measurements from fluorescent micrographs. The micrographs were formed using a Thorlabs CLS system, equipped with a Galvo:Resonant scanner and High-Sensitivity GaAsP PMTs recording into ThorImageLS software (Thorlabs Inc, New Jersey, U.S.A.). The scanner unit was mounted onto a Leica DMIRB microscope equipped with an oil immersion 63×NA 1.47 Leica HCX PL APO objective. Fluorescence detection was measured from single cells, with an excitation at 488 nm using a Coherent Sapphire 488 LP laser (Coherent Inc., CA, U.S.A.) and emission was collected between 500-550 nm. ROI data was analyzed using Image J and Matlab (Mathworks, MA, U.S.A.).

Immunocytochemistry

Cells were cultured on glass bottom dishes (Willco wells) and TRPV1 expression was induced in some dishes 18-24 hours before use. Both dishes containing cells expressing TRPV1 and non-induced cells were washed with buffer F then fixed and permeabilized using the Image-iT® Fixation/permeabilization kit (Invitrogen). Fixed and permeabilized cells were subjected to 25 µg/ml antibody in buffer F for 30 min at 37° C., then washed with buffer F followed by incubation with a goat anti-rabbit Alexa 488 secondary antibody for 30 min in room temperature. Cells were visualized after a final washing step and antibody distribution was compared between induced and non-induced cells.

TRPV1 Mediated YO-PRO Uptake

Glass bottom dishes containing 10 µl of electroporated cells were mounted to the microscope. Recording were initialized at a rate of 0.5 Hz. For OTV1 a 20 µl droplet containing capsaicin, YO—PRO and K4BAPTA in buffer F were carefully pipetted onto the electroporated cells in order to minimize detachment, causing a final concentration of 1 µM capsaicin, 1 µM YO-PRO and 10 mM $K_4$BAPTA. For OTV2 a 20 µl droplet containing capsaicin, YO—PRO and $Ca^{2+}$ in buffer F were similarly pipetted onto the electroporated cells causing a final concentration of 1 µM capsaicin, 1 µM YO-PRO and 50 µM $Ca^{2+}$.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

1 Jansson, E. T.; et. al., *Anal. Chem.* 2012, 84: 5582-5588
2 International application no. WO 2006/068619
3 European patent application no. EP 2174908
4 Trkulja, C. L., et al., *J. Am. Chem. Soc.* 2014, 136: 14875-14882
Freund, G. et al., *MAbs,* 2013, 5: 518-522

Example 3

Peptide Identification by Limited Digestion and Mass Spectrometry of the Ion Channel TRPV1 Expressed in CHO Cells, Using Multiple Proteases This example describes the use of multiple proteases in parallel to identify protease-specific sets of peptides from TRPV1. The proteases used in this example are trypsin, Asp-N, Pepsin, Proteinase K and chymotrypsin. When compared with each other, the protease-specific sets of peptides can be overlapping, complementary, or unique. Different proteolytic activities were achieved by using different protease concentrations and in a few examples by using different incubation times.

Materials and Methods

Cell Culture

In brief, CHO cells were cultured according to Trkulja et al. (J. Am. Chem. Soc. 2014, 136, 14875-14882). In brief, adherent Chinese hamster ovary (CHO) cells with a tetracycline-regulated expression system (T-REx) were cultivated in medium (DMEM/F12 with glutamine) supplemented with 10% FBS, Zeocin (350 µg/mL), and Blasticidin (5 µg/mL) in T175 or T500 culture flasks (Nunc) or on glass dishes. Before use (18-24 h), the cells were incubated in medium (DMEM/F12 with glutamine) supplemented with 10% FBS and Doxycycline (1 µg/mL) in order to induce expression of human TRPV1. The cell line was routinely tested for *mycoplasma* infection. After cell harvest, the cells were frozen and stored in −80 degrees. The cells were further processed as described below.

Cell Lysis and Homogenization

Cell suspensions were centrifuged for 580×g for 3 minutes. Supernatant were discarded and the tubes were filled carefully with 4 ml of ice-cold PBS. The cell pellets were re-suspended carefully and then the tubes were topped up to 14 ml with ice-cold PBS. Cell suspensions were again centrifuged for 580×g for 3 minutes, and the procedure was repeated two times.

The cell pellets (~800 µl volume) were re-suspended in approx. 6 ml of lysis buffer (10 mM $NaHCO_3$, pH 7.4) and kept on ice for 10 minutes.

The cells in lysis buffer were then transferred to a Dounce homogenizer (7 ml), one for each cell suspension. The cells were then subjected to homogenization with a tight pestle using 20 strokes. After homogenization, the lysed cells were subjected to a centrifugation step, 580×g for 3 minutes. The supernatant was collected and the cell pellets were discarded. The supernatants were subjected to a second centrifugation step, 580×g for 3 minutes and the cell pellet (small) was discarded.

The supernatants were pooled and transferred to a Beckman centrifuge tube (50 ml) and lysis buffer was added up to 20 ml. The supernatants were centrifuged for 10 minutes at 7300×g to remove mitochondria and cell debris. The supernatant was divided into two Falcon tubes (10 ml each) and frozen in a −80 freezer for further processing.

Ultracentrifugation

The supernatants were thawed on ice and transferred to two Beckman clear ultracentrifugation tubes (Beckman Coulter, item number 344057). The tubes were topped up with ice-cold buffer (10 mM Tris, 300 mM NaCl, pH 8) and carefully balanced prior centrifugation at 100,000×g (32900 rpm) for 45 minutes using a SW55 Ti rotor (Beckman Coulter). The supernatants were discarded and the pellets were re-suspended in ice-cold buffer (10 mM Tris, 300 mM NaCl, pH 8) and the tubes were again topped up with the same ice-cold buffer. After careful balancing and centrifugation at 100,000×g (32900 rpm) for 45 minutes, the supernatant was discarded and the pellets were re-suspended in ice-cold buffer (10 mM Tris, 300 mM NaCl, pH 8), approximately 800 µl per pellet. In total a membrane preparation of approximately 1.6 ml was collected and frozen in −80 degrees.

Tipsonication

The frozen membrane preparation was thawed on ice and pooled together prior sonication in an ice-cold conical vial using a sonicator (Vibracell). The membrane preparation was first diluted to 4 ml with ice-cold buffer (10 mM Tris, 300 mM NaCl, pH 8) and subjected to 30 seconds of sonication using 15% amplitude, 0.5 second pulse/rest cycle. The conical vial and membrane preparation were then cooled on ice for a few minutes and then another cycle using 15% amplitude, 0.5 second pulse/rest for 30 seconds were subjected to the membrane preparation and this was repeated again. The resulting membrane preparation (proteoliposomes) was frozen in 310 µl aliquots in −80 degrees.

Proteases

All proteases were purchased from Promega. All solutions were made using LC-MS grade water from Fisher Scientific.

Cat. No. V1621
Asp-N, Sequencing Grade, 2 µg
Cat. No. V1959
Pepsin, 250 mg
Cat. No. V3021
Proteinase K, 100 mg
Cat. No. V1062
Chymotrypsin, Sequencing Grade, 25 µg Cat. No. V5111
Sequencing Grade Modified Trypsin, 20 μg
Trypsin
Trypsin was dissolved in 100 mM Ammonium bicarbonate, Ambic, pH 8
Asp-N
Asp-N was dissolved in 100 mM Ammonium bicarbonate, Ambic, pH 8
Pepsin
Pepsin was dissolved in 100 mM Ammonium bicarbonate, Ambic, pH 8
Proteinase K
Proteinase K was dissolved in 100 mM Ammonium bicarbonate, Ambic, pH 8
Chymotrypsin
Chymotrypsin was dissolved in 100 mM Tris-HCl, 10 mM $CaCl_2$, pH 8.
LPI Processing The experiments were performed using LPI HexaLane-chips for the digestion. One lane within each chip were used for one digestion. In brief, aliquots of proteoliposomes were thawed to room temperature, manually injected into the lanes using a 100 μl pipette and immobilized for 1 hour.

Washing of the lanes was also performed manually using a 100 μl pipette. Each of the wells was washed with 200 μl wash buffer (same as digestion buffer, except for pepsin digestion protocol where 100 mM Ambic pH 8 was used as wash buffer. This was done to avoid low pH in the flow cell for a long time). The lanes were then washed with 4×100 μl of wash buffer using a 100 μl pipette.

Then protease was injected into the lane and incubated according to the specifications below. After digestion the peptides were eluted from the lane using 200 μl of digestion buffer (2×100 μl). By adding 4 μl of Formic acid, the protease activity was stopped by acidifying the resulting peptide solution to about pH 2. This was done for all samples except for pepsin, where 16 μl of ammonia solution (25%) was added instead to make the solution basic (pH 9).

The following digestion conditions were performed, one in each lane:
Trypsin:
0.5 μg/ml for 2.5 min
0.5 μg/ml for 5 min
2 μg/ml for 5 min
5 μg/ml for 5 min
10 μg/ml for 5 min
20 μg/ml for 5 min
Asp-N
20 μg/ml for 5 min
2 μg/ml for 24 hours
Chymotrypsin
5 μg/ml for 5 min
10 μg/ml for 5 min
20 μg/ml for 5 min
Proteinase-K
5 μg/ml for 5 min
10 μg/ml for 5 min
20 μg/ml for 5 min
Pepsin
2 μg/ml for 5 min
5 μg/ml for 5 min
10 μg/ml for 5 min
20 μg/ml for 5 min
The samples were labelled and frozen in −80° C.
MS analysis The tryptic peptides were desalted on PepClean C18 spin columns (Thermo Fisher Scientific, Inc., Waltham, Mass., USA) according to the manufacturers guidelines, dried and reconstituted with 15 micro-liter of 0.1% formic acid (Sigma Aldrich, St Louis, Mo.) in 3% gradient grade acetonitrile (Merck KGaA, Darmstadt, Germany). A two micro-liter sample injection was made with an Easy-nLC autosampler (Thermo Fisher Scientific, Inc., Waltham, Mass., USA) and analyzed with an interfaced Q Exactive hybrid mass spectrometer (Thermo Fisher Scientific). The peptides were trapped on a precolumn (45×0.075 mm i.d.) and separated on a reversed phase column, 200×0.075 mm, packed in-house with 3 μm Reprosil-Pur C18-AQ particles (Dr. Maisch, Ammerbuch, Germany). The nanoLC (liquid chromatography) gradient was running at 200 nl/min, starting at 7% acetonitrile (ACN) in 0.2% formic acid, increased to 27% ACN during 25 min, then increased to 40% during 5 min and finally to 80% ACN during 5 min and hold at 80% ACN for 10 min.

Ions were created and sprayed into the mass spectrometer under a voltage of 1.8 kV and capillary temperature of 320 degrees Celsius in data-dependent positive ion mode. Full scan (MS1) spectra were acquired in the Orbitrap over the m/z range 400-1,600, charge range 2-6 at a resolution of 70,000 until an AGC target value of 1 e6 at a maximum of 250 ms. MS/MS spectra were acquired using higher energy collision dissociation (HCD) at 30% from m/z 110 for the ten most abundant parent ions at a resolution of 35,000 using a precursor isolation window of 2 Da until an AGC target value of 1 e5 during an injection time of 110 ms. Dynamic exclusion during 30 s after selection for MS/MS was enabled to allow for detection of as many precursors as possible.

Summary of Results

Figure 10:
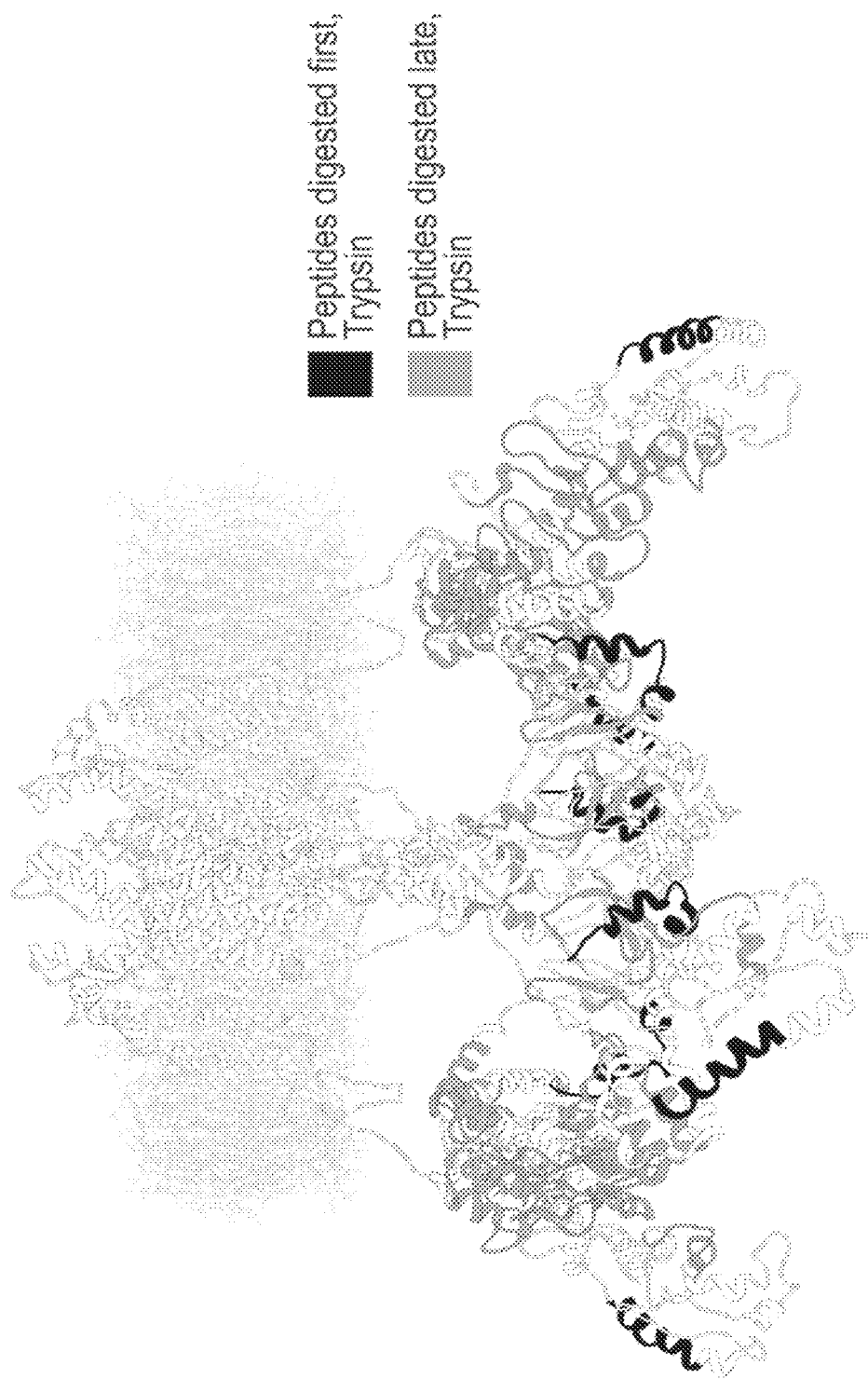

FIG. 10 shows the location on a 3D model of TRPV1 of peptides detected after limited proteolysis by trypsin. The sequences of detected peptides after limited proteolysis by trypsin are shown below in Table 2. Peptides digested with 0.5 μg/ml trypsin for 2.5 min are shown first. Peptides digested with 0.5 μg/ml trypsin for 5 min, 2 μg/ml trypsin for 5 min, 5 μg/ml trypsin for 5 min, 10 μg/ml trypsin for 5 min and 20 μg/ml trypsin for 5 min respectively have been pooled for presentation purposes and are shown secondly.

TABLE 2

| Start | Stop | Sequence |
|---|---|---|
| | | Peptides digested with 0.5 μg/ml trypsin for 2.5 min (*) |
| 96 | 108 | LLSQDSVAASTEK (SEQ ID NO: 2) |
| 96 | 111 | LLSQDSVAASTEKTLR (SEQ ID NO: 3) |
| 817 | 839 | QFSGSLKPEDAEVFKSPAASGEK (SEQ ID NO: 4) |
| | | Peptides digested with 0.5 μg/ml trypsin for 5 min, 2 μg/ml trypsin for 5 min, 5 μg/ml trypsin for 5 min, 10 μg/ml trypsin for 5 min and 20 μg/ml trypsin for 5 min. (**) |
| 4 | 18 | WSSTDLGAAADPLQK (SEQ ID NO: 27) |
| 96 | 108 | LLSQDSVAASTEK (SEQ ID NO: 28) |
| 96 | 111 | LLSQDSVAASTEKTLR (SEQ ID NO: 29) |
| 162 | 182 | AMLNLHDGQNTTIPLLLEIAR (SEQ ID NO: 30) |
| 183 | 201 | QTDSLKELVNASYTDSYYK (SEQ ID NO: 31) |

TABLE 2-continued

| Start | Stop | Sequence |
|---|---|---|
| 202 | 212 | GQTALHIAIER (SEQ ID NO: 32) |
| 214 | 239 | NMALVTLLVENGADVQAAAHGDFFKK (SEQ ID NO: 33) |
| 267 | 281 | FLLQNSWQTADISAR (SEQ ID NO: 34) |
| 282 | 304 | DSVGNTVLHALVEVADNTADNTK (SEQ ID NO: 35) |
| 320 | 332 | LHPTLKLEELTNK (SEQ ID NO: 36) |
| 333 | 346 | KGMTPLALAAGTGK (SEQ ID NO: 37) |
| 334 | 346 | GMTPLALAAGTGK (SEQ ID NO: 38) |
| 347 | 356 | IGVLAYILQR (SEQ ID NO: 39) |
| 703 | 711 | AITILDTEK (SEQ ID NO: 40) |
| 773 | 779 | TLSFSLR (SEQ ID NO: 41) |
| 790 | 798 | NFALVPLLR (SEQ ID NO: 42) |
| 799 | 816 | EASARDRQSAQPEEVYLR (SEQ ID NO: 43) |
| 804 | 816 | DRQSAQPEEVYLR (SEQ ID NO: 44) |
| 806 | 816 | QSAQPEEVYLR (SEQ ID NO: 45) |
| 817 | 831 | QFSGSLKPEDAEVFK (SEQ ID NO: 46) |
| 817 | 839 | QFSGSLKPEDAEVFKSPAASGEK (SEQ ID NO: 47) |

Figure 11:

FIG. 11 shows the location on a 3D model of TRPV1 of peptides detected after limited proteolysis by Asp-N. The sequences of detected peptides after limited proteolysis by Asp-N are shown below in Table 3. Peptides digested with 20 μg/ml Asp-N for 5 min are shown first. Peptides digested with 2 μg/ml Asp-N for 24 hours are shown secondly.

TABLE 3

| Start | Stop | Sequence |
|---|---|---|
| | | Peptides digested with 20 μg/ml Asp-N for 5 min (*) |
| 89 | 99 | DGPTGARLLSQ (SEQ ID NO: 8) |
| 826 | 839 | DAEVFKSPAASGEK (SEQ ID NO: 9) |
| | | Peptides digested with 2 μg/ml Asp-N for 24 hours (**) |
| 89 | 99 | DGPTGARLLSQ (SEQ ID NO: 48) |
| 100 | 113 | DSVAASTEKTLRLY (SEQ ID NO: 49) |
| 168 | 184 | DGQNTTIPLLLEIARQT (SEQ ID NO: 50) |
| 185 | 196 | DSLKELVNASYT (SEQ ID NO: 51) |
| 282 | 296 | DSVGNTVLHALVEVA (SEQ ID NO: 52) |
| 826 | 839 | DAEVFKSPAASGEK (SEQ ID NO: 53) |

Figure 12:

FIG. 12 shows the location on a 3D model of TRPV1 of peptides detected after limited proteolysis by chymotrypsin. The sequences of detected peptides after limited proteolysis by chymotrypsin are shown below in Table 4. Peptides digested with 5 μg/ml chymotrypsin for 5 min are shown first. Peptides digested with 10 μg/ml chymotrypsin for 5 min and 20 μg/ml chymotrypsin for 5 min respectively have been pooled for presentation purposes and are shown secondly.

TABLE 4

| Start | Stop | Sequence |
|---|---|---|
| | | Peptides digested with 5 μg/ml chymotrypsin for 5 min (*) |
| 98 | 110 | SQDSVAASTEKTL (SEQ ID NO: 10) |
| 819 | 830 | SGSLKPEDAEVF (SEQ ID NO: 11) |
| | | Peptides digested with 10 μg/ml chymotrypsin for 5 min and 20 μg/ml chymotrypsin for 5 min (**) |
| 97 | 110 | LSQDSVAASTEKTL (SEQ ID NO: 54) |
| 98 | 110 | SQDSVAASTEKTL (SEQ ID NO: 55) |
| 98 | 113 | SQDSVAASTEKTLRLY (SEQ ID NO: 56) |
| 165 | 176 | NLHDGQNTTIPL (SEQ ID NO: 57) |
| 221 | 237 | LVENGADVQAAAHGDFF (SEQ ID NO: 58) |
| 274 | 289 | QTADISARDSVGNTVL (SEQ ID NO: 59) |
| 290 | 305 | HALVEVADNTADNTKF (SEQ ID NO: 60) |
| 341 | 352 | AAGTGKIGVLAY (SEQ ID NO: 61) |
| 819 | 830 | SGSLKPEDAEVF (SEQ ID NO: 62) |

Figure 13:
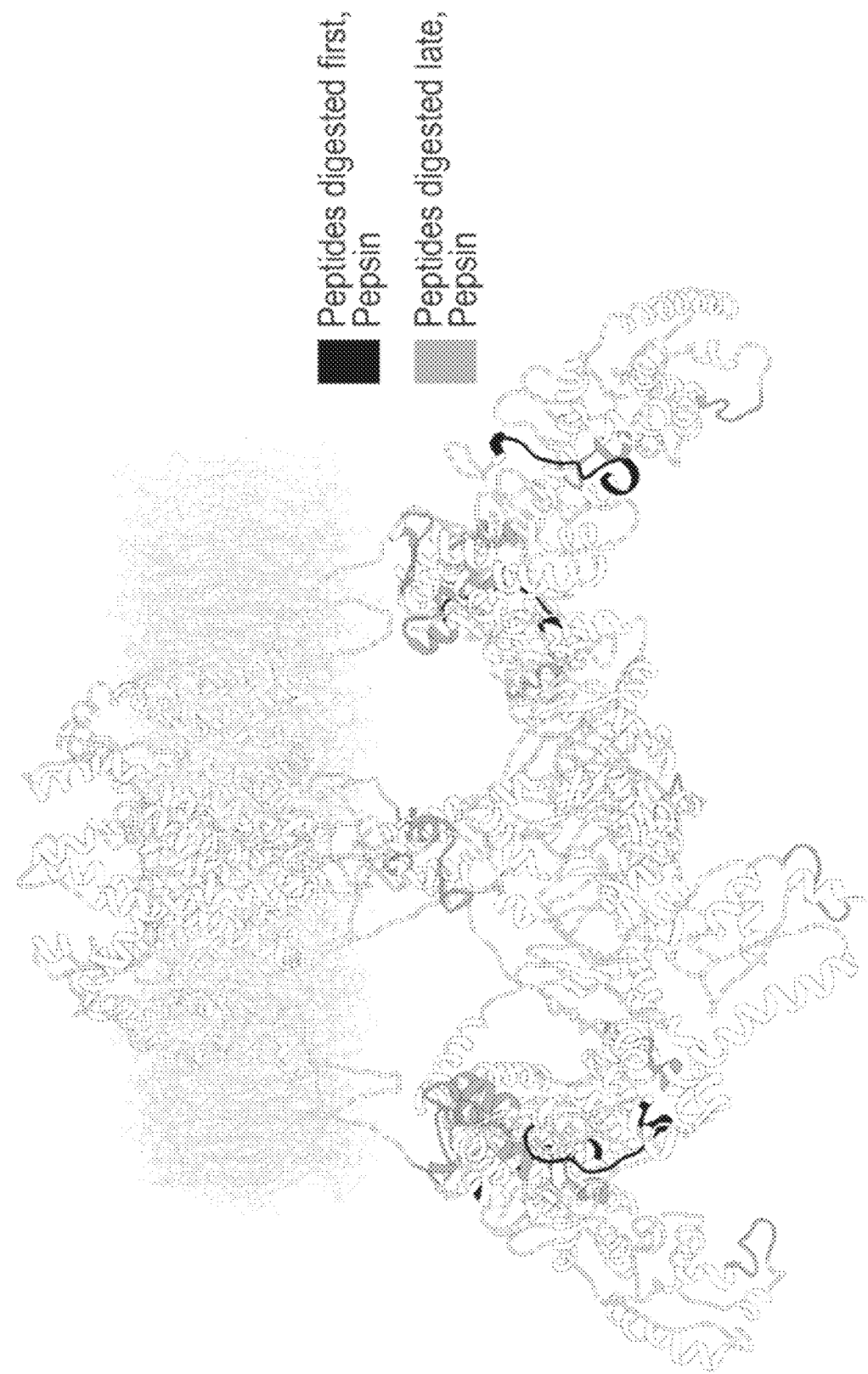

FIG. 13 shows the location on a 3D model of TRPV1 of peptides detected after limited proteolysis by pepsin. The sequences of detected peptides after limited proteolysis by pepsin are shown below in Table 5. Peptides digested with 2 μg/ml pepsin for 5 min are shown first. Peptides digested with 5 μg/ml pepsin for 5 min, 10 μg/ml pepsin for 5 min and 20 μg/ml pepsin for 5 min respectively have been pooled for presentation purposes and are shown secondly.

TABLE 5

| Start | Stop | Sequence |
|---|---|---|
| | | Peptides digested with 2 μg/ml pepsin for 5 min (*) |
| 221 | 236 | LVENGADVQAAAHGDF (SEQ ID NO: 7) |
| | | Peptides digested with 5 μg/ml pepsin for 5 min, 10 μg/ml pepsin for 5 min and 20 μg/ml pepsin for 5 min (**) |
| 50 | 59 | FGKGDSEEAF (SEQ ID NO: 63) |
| 167 | 177 | HDGQNTTIPLL (SEQ ID NO: 64) |
| 221 | 236 | LVENGADVQAAAHGDF (SEQ ID NO: 65) |
| 222 | 235 | VENGADVQAAAHGD (SEQ ID NO: 66) |
| 222 | 236 | VENGADVQAAAHGDF (SEQ ID NO: 67) |
| 290 | 305 | HALVEVADNTADNTKF (SEQ ID NO: 68) |
| 293 | 305 | VEVADNTADNTKF (SEQ ID NO: 69) |
| 398 | 414 | EVIAYSSSETPNRHDML (SEQ ID NO: 70) |

Figure 14:
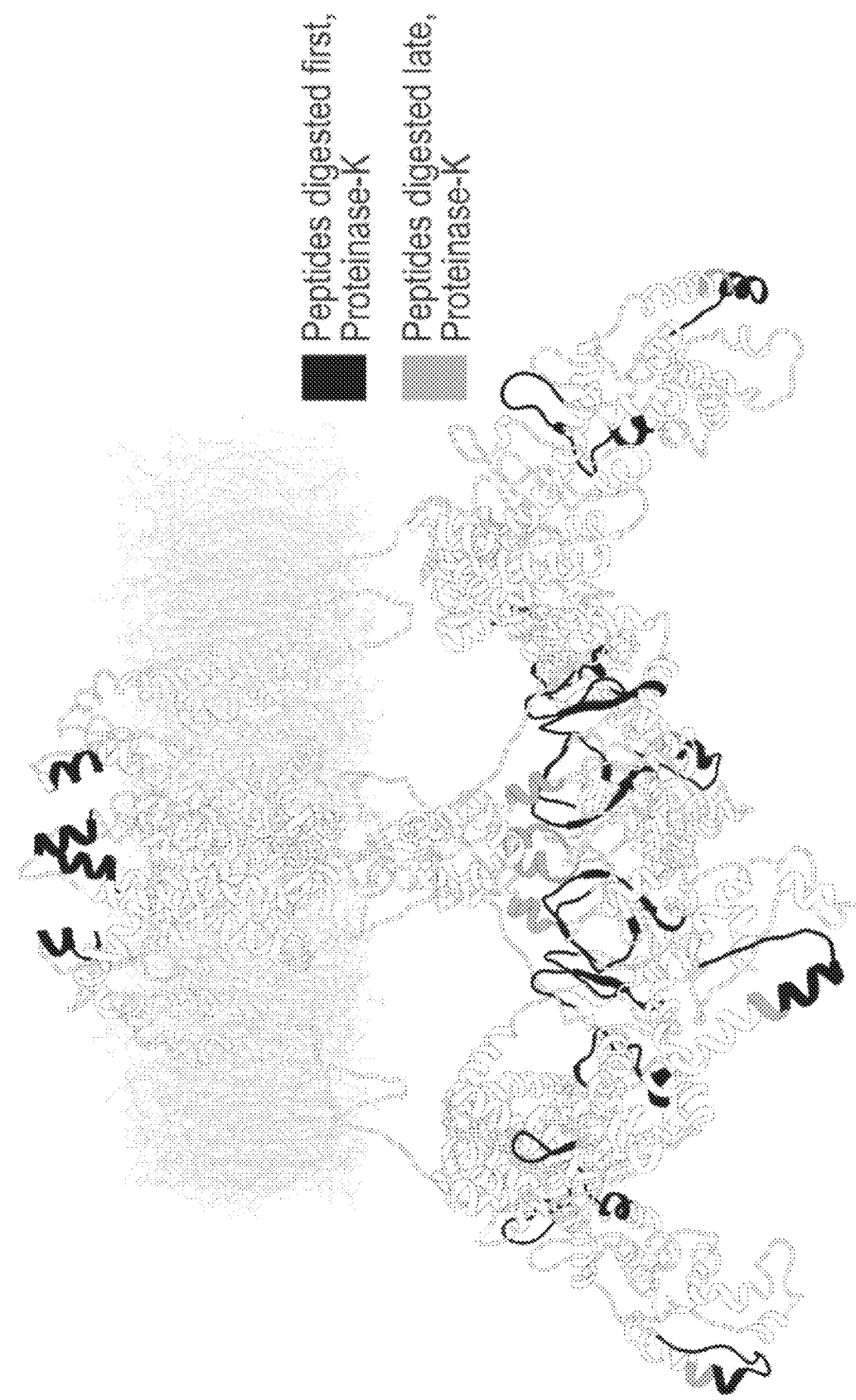

FIG. 14 shows the location on a 3D model of TRPV1 of peptides detected after limited proteolysis by Proteinase K. The sequences of detected peptides after limited proteolysis by Proteinase K are shown below in Table 6. Peptides digested with 5 µg/ml proteinase K for 5 min are shown first. Peptides digested with 10 µg/ml proteinase K for 5 min, and 20 µg/ml proteinase K for 5 min respectively have been pooled for presentation purposes and are shown secondly.

TABLE 6

| Start | Stop | Sequence |
|---|---|---|
| Peptides digested with 5 µg/ml proteinase K for 5 min (*) | | |
| 78 | 89 | VSPVITIQRPGD (SEQ ID NO: 12) |
| 78 | 94 | VSPVITIQRPGDGPTGA (SEQ ID NO: 13) |
| 164 | 178 | LNLHDGQNTTIPLLL (SEQ ID NO: 14) |
| 195 | 203 | YTDSYYKGQ (SEQ ID NO: 15) |
| 606 | 614 | SLPSESTSH (SEQ ID NO: 16) |
| 762 | 772 | EDPGNCEGVKR (SEQ ID NO: 17) |
| 804 | 816 | DRQSAQPEEVYLR (SEQ ID NO: 18) |
| 806 | 816 | QSAQPEEVYLR (SEQ ID NO: 19) |
| Peptides digested with 10 µg/ml proteinase K for 5 min, and 20 µg/ml proteinase K for 5 min (**) | | |
| 78 | 94 | VSPVITIQRPGDGPTGA (SEQ ID NO: 71) |
| 84 | 95 | IQRPGDGPTGAR (SEQ ID NO: 72) |
| 86 | 97 | RPGDGPTGARLL (SEQ ID NO: 73) |
| 164 | 178 | LNLHDGQNTTIPLLL (SEQ ID NO: 74) |
| 708 | 715 | DTEKSFLK (SEQ ID NO: 75) |
| 762 | 772 | EDPGNCEGVKR (SEQ ID NO: 76) |
| 762 | 773 | EDPGNCEGVKRT (SEQ ID NO: 77) |
| 762 | 774 | EDPGNCEGVKRTL (SEQ ID NO: 78) |
| 801 | 816 | SARDRQSAQPEEVYLR (SEQ ID NO: 79) |
| 804 | 816 | DRQSAQPEEVYLR (SEQ ID NO: 80) |
| 806 | 816 | QSAQPEEVYLR (SEQ ID NO: 81) |

In Tables 2, 3, 4, 5 and 6 the terms "start" and "stop" refer to the positions of the amino acid residues in the TRPV1 sequence.

During evaluation of the data a Mascot Significance Threshold of 0.01 has been set under Results Filters (Peptide).

Trypsin produced an increased number of peptides and increased confidence with an increased protease concentration.

Pepsin and Chymotrypsin both gave rise to a number of peptides both at low and higher concentrations.

Example 4

This Example relates to Method C.
Materials and Methods
Cell Culture, Cell Harvest and Proteoliposome Preparation Human embryonic kidney cells were cultured in plastic flasks according to standard cell culture methods, at 5% $CO_2$ and 37° C. in Ham's F12 medium (Invitrogen, Cat. No. 31765) supplemented with fetal calf serum (PAA, Cat. No. A15-649), non-essential amino acids (Invitrogen, Cat. No. 11140035). The cells were routinely tested for *mycoplasma* infection. Cells were detached using Accutase (PAA, Cat. No. L11-007), washed three times in PBS and pelleted. Pellets were resuspended in 1:1 lysis buffer, which contained mannitol (225 mM), sucrose (75 mM), EGTA (0.1 mM) and Tris-HCl (30 mM), pH 7.4. After cell harvest, the cells were frozen and stored at minus 80° C.

Cell pellets were thawed on ice and the volume adjusted using lysis buffer. The cell suspension was lysed and homogenized using a Dounce homogenizer with a tight pestle. The supernatant was cleared from mitochondria and cell debris by two repeated centrifugations at 7000×g for 20 minutes using a Beckman Avanti J-301 centrifuge with a JA-3050 rotor. Intracellular membranes including plasma membrane were pelleted from the supernatant by two rounds of ultra-centrifugation at 100,000×g using a Beckman Optima™ XE-90 with a SW 41 Ti rotor. Ultracentrifugation was performed for 45 minutes at 4° C. The supernatants were discarded and the pellets were resuspended into ice-cold PBS and frozen at −20° C. until further use.

Membrane preparations were thawed on ice and sonicated in an ice-cold conical vial using a sonicator (Vibracell) to create proteoliposomes. The resulting proteoliposome preparation was diluted into phosphate-buffered saline (pH 7.4) and stored at −20° C. until further use.

Sample Processing

The experiments were performed using flowcells (Nanoxis Consulting AB, Gothenburg, Sweden). In brief, 50 µL aliquots of samples were thawed to room temperature, and manually injected into flowcell lanes and immobilized for 1 hour. Each of the lanes was washed with 200 µl wash buffer (100 mM Ambic pH 8) to remove unbound material followed by solutions of protease or wash solutions according to each specific protocol. For the limited digestions, we stopped digestion of the proteoliposome samples after 5 minutes by eluting the protease solution from the flowcell using 100 µL of 100 mM ammonium bicarbonate, pH 8. Trifluoroacetic acid was immediately added to reduce the pH, and then the sample was frozen.

Proteases were from Promega (Chymotrypsin, Sequencing Grade, 25 µg, Cat. No. V1062; Sequencing Grade Modified Trypsin, 20 µg, Cat. No. V5111; Proteinase K, 100 mg, Cat. No. V3021). Trypsin working solutions were prepared in 100 mM ammonium bicarbonate, pH 8. Proteinase K and chymotrypsin working solutions were prepared in Tris-HCl 100 mM+$CaCl_2$ 10 mM, pH8.0.

3 replicate channels were used for each protocol. The peptide samples were merged before MS analysis.

MS Analysis

Peptides released by the proteolysis in Steps 1 and 3 of the protocols in Table 7 were analysed. Samples obtained following the proteolysis in Step 1 were analysed separately from samples obtained following the proteolysis in Step 3.

Peptides were desalted on PepClean C18 spin columns (Thermo Fisher Scientific, Inc., Waltham, Mass., USA) according to the manufacturers guidelines, dried and reconstituted with microliters of 0.1% formic acid (Sigma Aldrich, St Louis, Mo.) in 3% gradient grade acetonitrile (Merck KGaA, Darmstadt, Germany).

A two micro-liter sample injection was made with an Easy-nLC autosampler (Thermo Fisher Scientific, Inc., Waltham, Mass., USA). Samples were analysed on high accuracy Orbitrap instruments. Orbitrap Fusion Tribrid, Q-Exactive or Orbitrap Elite mass spectrometers (Thermo Fisher Scientific) were interfaced with Easy nanoLC 1200 liquid chromatography systems. Peptides were separated using an in-house constructed analytical column (300×0.075 mm I.D.) packed with 3 μm Reprosil-Pur C18-AQ particles (Dr. Maisch, Germany) using the gradient from 5-7% to 30-32% B over 35, 50 or 75 minutes, followed by and increase to 100% B for 5 min at a flow of 300 nL/min. Solvent A was 0.2% formic acid in water and solvent B was 0.2% formic acid in 80% acetonitrile. MS/MS analysis was performed in a data-dependent mode where the most intense precursor ions at charge states 2 to 7 were selected for fragmentation. Dynamic exclusion was set to 30 s.

Each sample was injected 3 times, and the MS data for the 3 injections was merged and treated as a single sample.

Data analysis was performed utilizing Proteome Discoverer version 1.4 (Thermo Fisher Scientific). Mascot 2.3.2.0 (Matrix Science) was used as a search engine with precursor mass tolerance of 5 ppm and fragment mass tolerance of 0.6 Da, and the sequence 35 database was from UniProt (Swissprot section, taxonomic division=human, version 2017_03, approx. 20,100 protein sequences). Peptides were accepted with 1 to 3 missed cleavage and variable modifications of methionine oxidation, cysteine alkylation and PNGase F. The detected peptide threshold in the software was set to 1% False Discovery Rate by searching against a reversed database. Only peptides of high identification confidence were considered. The inclusion criteria were as follows: peptides with score equal to or greater than 19, and a peptide confidence of 2 or 3 (where 3 is best and 1 is worst) were included. These criteria represent a Mascot significance of 0.01 or better, a standard criterion used for published proteomics data. At this setting, only 1% of peptide identifications are likely to be false. Peptide scores were assigned by Mascot and confidence values assigned by Proteome Discoverer.

Protein annotations, including membrane associations, were fetched from The Universal Protein Resource (UniProt). UniProt is a collaboration between the European Bioinformatics Institute (EMBL-EBI), the SIB Swiss Institute of Bioinformatics and the Protein Information Resource (PIR).

Results

Using the multiprotease protocols in the examples, the protease used in the first step cleaves proteins at various positions dictated by its substrate specificity. Sometimes whole peptides are cut off and are detectable by mass spectrometry, and these detectable peptides are generally at least 8 amino acids and at most 30-40 amino acids long depending on the nature of the analysis method. In other cases, especially if limited digestion is used, the protease makes a cut but a peptide is not released. Another way to view this is that the protease creates nicks. For example, chymotrypsin will create nicks on the C-terminal side of the amino acids F, W, L, and Y. With limited digestion, surface nicks are the most likely. Cuts created in the first proteolytic step, that are not detected in that step, can be detected in subsequent steps when the one or more subsequent steps uses a protease with a substrate specificity other than that of the first. For example, if the first step uses chymotrypsin and a second step uses trypsin, which cuts at the C-terminal side of the amino acids K and R, peptides detected in the second step may show that chymotrypsin did cut at one end (the nick) and trypsin at the other. The subsequent steps may utilize non-limited digestion conditions to ensure that peptides are released, but it is possible to use several sequential limited digestion steps. Preferably, the protease in the one or more subsequent steps have a different specificity than that used in the first step so that it will be obvious which cuts were produced in the first step. Cuts, or nicks, created by the first protease are evidence of surface exposure, and can therefore be used for epitope discovery.

The following examples show data acquired using the protocols in Table 7, and demonstrate how cuts produced by limited digestion in a first step are detected by a second step of digestion. Table 8 lists the cleavage specificity of the proteases applied. Tables 9-13 show proteins and peptides identified using these protocols.

TABLE 7

| Protocol number | Step 1 | Step 2 | Step 3 | Step 4 |
| --- | --- | --- | --- | --- |
| Multiprotease protocol 1 | Chymotrypsin 2 μg/mL 5 min | Wash | Trypsin 20 μg/mL 1 hr | Elute, stop reaction, freeze |
| Multiprotease protocol 2 | Trypsin 5 μg/mL 5 min | Wash | Chymotrypsin 20 μg/mL 5 min | Elute, stop reaction, freeze |
| Multiprotease protocol 3 | Proteinase K 2 μg/mL 5 min | Wash | Trypsin 20 μg/mL 1 hr | Elute, stop reaction, freeze |

In multiprotease protocols 1, 2 and 3 (see Table 7), both "Step 1" and "Step 3" were performed at room temperature (20° C.–25° C.).

In each of multiprotease protocols 1, 2 and 3, "Step 1" is a step of limited or restricted proteolysis.

In each of multiprotease protocols 1 and 3, "Step 3" is a step of non-limited proteolysis. In multiprotease protocol 2, "Step 3" is a step of of limited or restricted proteolysis.

TABLE 8

| Protease | Specificity (amino acids) |
| --- | --- |
| Trypsin | Cuts at the C-terminal (carboxyl) side of K and R |
| Chymotrypsin | Cuts at the C-terminal (carboxyl) side of F, L, W and Y |
| ProteinaseK | Broad specificity |

In Tables 9-12, Acc # and Protein Name indicate the protein accession number and protein name, respectively, according to nomenclature at UniprotKB. Start and Stop give the amino acid positions, within the protein sequence, of the N-terminal and C-terminal of the peptide. L_flank indicates the left (N-terminal) amino acid flanking the peptide in the protein sequence. R_flank indicates the final (C-terminal) amino acid in the Peptide Sequence.

Table 9 shows a subset of transmembrane proteins and their respective peptides detected after the trypsin digestion step of Multiprotease protocol 1 (chymotrypsin 2 μg/mL 5 min, followed by trypsin 20 μg/mL 1 hr). The sample contained peptides cut solely by trypsin. The sample also contained peptides that are cut at one end with chymotrypsin and with trypsin at the other. These peptides are indicated by an asterisk in the column named MultiProtCut, i.e. a multiprotease cut. An example is the peptide SSPAGGVLGG-GLGGGGGR from the protein Mannosyl-oligosaccharide 1,2-alpha-mannosidase IA. The left flank amino acid is F and the last amino acid in the peptide is R. The protein was cut by chymotrypsin in the first proteolysis step, after F, and by trypsin in the second proteolysis step, after R.

Depending on the size, abundance and availability of cut sites of each protein, different numbers of peptides are detected for each protein. The listed proteins were not detected in the first proteolytic step (Step 1).

Table 10 shows a subset of non-transmembrane proteins for Multiprotease protocol 1. The method works similarly well for both membrane and non-membrane proteins. Peptides that are cut at one end with chymotrypsin and with trypsin at the other are indicated by an asterisk in the column named MultiProtCut.

Table 11 shows a subset of transmembrane proteins and their respective peptides detected in the chymotrypsin digestion step of Multiprotease protocol 2 (trypsin 5 µg/mL 5 min, followed by chymotrypsin 20 µg/mL 5 min). The sample contained peptides cut solely by chymotrypsin. The sample also contained peptides that are cut at one end with trypsin and with chymotrypsin at the other (marked with an asterisk).

Table 12 shows a subset of non-transmembrane proteins for Multiprotease protocol 2. The sample also contained peptides that are cut at one end with trypsin and with chymotrypsin at the other (marked with an asterisk).

In the above two examples (Protocols 1 and 2), the proteases are the same but the order of use is reversed, showing that the method works independently of the protease order.

Peptide sequences were also identified using multiprotease protocol 3, including peptide sequences that were released by cleavage of the protein by the two different proteases, i.e. including peptide sequences in which one end has been cut by Proteinase K and the other end by trypsin.

Table 13 shows the amino acids at which Proteinase K cut in Multiprotease Protocol 3, and the frequency per amino acid, based on peptides cut at one end with trypsin and with Proteinase K at the other. The listed cut sites were derived from high confidence peptide identifications with peptide scores equal to or greater than 19. As seen, the specificity is quite broad and so Proteinase K is a type of protease which can beneficially be used in one of the limited digestion steps. A protease with broad specificity is less sensitive to the number and position of accessible cleavage sites on the surface of proteins.

TABLE 9

Multiprotease protocol 1 (chymotrypsin 2 µg/mL 5 min, followed by trypsin 20 µg/mL 1 hr). Transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| P33908 | Mannosyl-oligosaccharide 1,2-alpha-mannosidase IA | 11 | 28 | F | SSPAGGVLGGGL GGGGGR | R | * | 45.6 | 82 |
|  |  | 526 | 536 | R | FDGGVEAIATR | R |  | 56.93 | 83 |
| P51648 | Fatty aldehyde dehydrogenase | 38 | 51 | R | EKDILTAIAADL CK | K |  | 40.89 | 84 |
|  |  | 178 | 191 | R | FDHIFYTGNTAV GK | K |  | 29.78 | 85 |
|  |  | 291 | 299 | R | ILSLLEGQK | K |  | 45.13 | 86 |
|  |  | 300 | 311 | K | IAFGGETDEATR | R |  | 66.83 | 87 |
|  |  | 300 | 312 | K | IAFGGETDEATR Y | Y | * | 61.74 | 88 |
|  |  | 312 | 324 | R | YIAPTVLTDVDP K | K |  | 54.9 | 89 |
|  |  | 313 | 324 | Y | IAPTVLTDVDPK | K | * | 41.92 | 90 |
|  |  | 327 | 343 | K | VMQEEIFGPILP IVPVK | K |  | 67.33 | 91 |
|  |  | 344 | 355 | K | NVDEAINFINER | R |  | 56.03 | 92 |
| P60033 | CD81 antigen | 125 | 144 | K | QFYDQALQQAWD DDANNAK | K |  | 63.53 | 93 |
|  |  | 149 | 162 | K | TFHETLDCCGSS TL | L | * | 31.63 | 94 |
| Q8NGR6 | Olfactory receptor 1B1 | 220 | 226 | L | IVLSYVR | R | * | 32.63 | 95 |
| Q96S66 | Chloride channel CLIC-like protein 1 | 47 | 70 | Y | GISGEKDVSPDL SCADEISECYHK | K | * | 40.71 | 96 |
|  |  | 132 | 139 | R | ETLLEIQK | K |  | 43.85 | 97 |
|  |  | 402 | 412 | R | GQMGPTEQGPY | Y | * | 29.31 | 98 |
| Q9NYM4 | Probable G-protein coupled receptor 83 | 8 | 15 | L | LCLLPLVR | R | * | 44.92 | 99 |
| O75915 | PRA1 family protein 3 | 10 | 20 | R | AWDDFFPGSDR | R |  | 28.92 | 100 |
|  |  | 160 | 178 | R | TPMGIVLDALEQ QEEGINR | R |  | 42.31 | 101 |

TABLE 9-continued

Multiprotease protocol 1 (chymotrypsin 2 µg/mL 5 min, followed by trypsin 20 µg/mL 1 hr). Transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| | | 167 | 178 | L | DALEQQEEGINR | R | * | 42.72 | 102 |
| | | 179 | 185 | R | LTDYISK | K | | 32.86 | 103 |
| Q86UL3 | Glycerol-3-phosphate acyl-transferase 4 | 161 | 171 | L | TVLWGLGVLIR | R | * | 30.6 | 104 |
| | | 394 | 405 | R | EADEDAVQFANR | R | | 69.17 | 105 |
| | | 413 | 427 | R | QGGLVDLLWDGGLKR | R | | 38 | 106 |

TABLE 10

Multiprotease protocol 1 (chymotrypsin 2 µg/mL 5 min, followed by trypsin 20 µg/mL 1 hr). Non-transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| A5A3E0 | POTE ankyrin domain family member F | 709 | 718 | L | VIDNGSGMCK | K | * | 26.24 | 107 |
| | | 719 | 728 | K | AGFAGDDAPR | R | | 75.14 | 108 |
| | | 729 | 737 | R | AVFPSIVGR | R | | 34.42 | 109 |
| | | 732 | 739 | F | PSIVGRPR | R | * | 28.34 | 110 |
| | | 785 | 795 | K | IWHHTFYNELR | R | | 43.94 | 111 |
| | | 848 | 861 | R | TTGIVMDSGDGVTH | H | | 45.59 | 112 |
| | | 939 | 954 | K | SYELPDGQVITIGNER | R | | 105.89 | 113 |
| | | 941 | 954 | Y | ELPDGQVITIGNER | R | * | 37.85 | 114 |
| | | 1057 | 1072 | W | ISKQEYDESGPSIVHR | R | * | 43.32 | 115 |
| | | 1060 | 1071 | K | QEYDESGPSIVH | H | | 37.17 | 116 |
| | | 1060 | 1072 | K | QEYDESGPSIVHR | R | | 49.02 | 117 |
| P00387 | NADH-cytochrome b5 reductase 3 | 30 | 42 | R | STPAITLESPDIK | K | | 45.39 | 118 |
| | | 30 | 46 | R | STPAITLESPDIKYPLR | R | | 44.32 | 119 |
| | | 47 | 58 | R | LIDREIISHDTR | R | | 27.36 | 120 |
| | | 85 | 94 | R | IDGNLVVRPY | Y | * | 54.65 | 121 |
| | | 95 | 111 | Y | TPISSDDDKGFVDLVIK | K | * | 37.4 | 122 |
| | | 112 | 120 | K | VYFKDTHPK | K | | 30.61 | 123 |
| | | 144 | 154 | R | GPSGLLVYQGK | K | | 62.08 | 124 |
| | | 174 | 192 | K | SVGMIAGGTGITPMLQVIR | R | | 95.21 | 125 |
| | | 215 | 225 | K | DILLRPELEEL | L | * | 31.22 | 126 |
| | | 233 | 241 | R | FKLWYTLDR | R | | 29 | 127 |
| | | 235 | 241 | K | LWYTLDR | R | | 27.96 | 128 |
| | | 242 | 259 | R | APEAWDYGQGFVNEEMIR | R | | 53.3 | 129 |
| P01042 | Kininogen-1 | 177 | 183 | L | FMLNEVK | K | * | 29.35 | 130 |
| P08134 | Rho-related GTP-binding protein RhoC | 19 | 27 | K | TCLLIVFSK | K | | 42.6 | 131 |
| | | 59 | 68 | W | DTAGQEDYDR | R | * | 52.56 | 132 |
| | | 105 | 118 | K | HFCPNVPIILVGNK | K | | 32.5 | 133 |
| | | 105 | 119 | K | HFCPNVPIILVGNKK | K | | 40.35 | 134 |
| | | 110 | 118 | N | VPIILVGNK | K | | 34.31 | 135 |
| | | 169 | 176 | R | EVFEMATR | R | | 38.57 | 136 |

TABLE 11

Multiprotease protocol 2
(trypsin 5 µg/mL 5 min, followed by chymotrypsin
20 µg/mL 5 min). Transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| Q92581 | Sodium/hydrogen exchanger 6 | 603 | 618 | Y | GDSTVNTEPATSSAPR | R | * | 52.17 | 137 |
| Q06481 | Amyloid-like protein 2 | 576 | 587 | F | TASISETPVDVR | R | * | 51.41 | 138 |
| O00264 | Membrane-associated progesterone receptor component 1 | 181 | 192 | Y | SDEEEPKDESAR | R | * | 27.43 | 139 |
| Q96BZ4 | Phospholipase D4 | 81 | 88 | W | EPLEAEAR | R | * | 28.53 | 140 |
| P50281 | Matrix metalloproteinase-14 | 152 | 158 | W | ESATPLR | R | * | 24.48 | 141 |
| Q6DD88 | Atlastin-3 | 14 | 31 | R | GADDAMESSKPGPVQVVL | L | * | 26.63 | 142 |
| O95070 | Protein YIF1A | 16 | 33 | R | ARAAPDPPPLFDDTSGGY | Y | * | 31.31 | 143 |
|  |  | 18 | 33 | R | AAPDPPPLFDDTSGGY | Y | * | 34.74 | 144 |
| P23763 | Vesicle-associated membrane protein 1 | 62 | 72 | K | LSELDDRADAL | L | * | 35.03 | 145 |
|  |  | 62 | 79 | K | LSELDDRADALQAGASQF | F | * | 73.36 | 146 |
| Q96S66 | Chloride channel CLIC-like protein 1 | 515 | 531 | K | AQLKSEAAGSPDQGSTY | Y | * | 44.98 | 147 |
| Q14789 | Golgin subfamily B member 1 | 164 | 185 | L | QAQLTQAQAEQPAQSSTEMEEF | F |  | 22.14 | 148 |
|  |  | 537 | 552 | R | SSSAEESGQDVLENTF | F | * | 31.56 | 149 |
|  |  | 3106 | 3117 | L | NIDVAPGAPQEK | K | * | 31.92 | 150 |
| Q6DD88 | Atlastin-3 | 14 | 31 | R | GADDAMESSKPGPVQVVL | L | * | 26.63 | 151 |
| Q6IAN0 | Dehydrogenase/reductase SDR family member 7B | 245 | 255 | L | SVNAITADGSR | R | * | 24.79 | 152 |
| Q8TE54 | Anion exchange transporter | 512 | 518 | L | VFLNAKK | K | * | 21.46 | 153 |
| Q8IY95 | Transmembrane protein 192 | 214 | 226 | Y | AYPSNITSETGFR | R | * | 38.14 | 154 |
| Q9BVT8 | Transmembrane and ubiquitin-like domain-containing protein 1 | 90 | 106 | F | TATPPAPDSPQEPLVLR | R | * | 25.52 | 155 |

TABLE 12

Multiprotease protocol 2
(trypsin 5 µg/mL 5 min, followed by chymotrypsin
20 µg/mL 5 min). Non-transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| P26599 | Polypyrimidine tract-binding protein 1 | 30 | 45 | F | IMSSNSASAANGNDSK | K | * | 105.68 | 156 |
|  |  | 30 | 46 | F | IMSSNSASAANGNDSKK | K | * | 49.66 | 157 |

TABLE 12-continued

Multiprotease protocol 2
(trypsin 5 µg/mL 5 min, followed by chymotrypsin
20 µg/mL 5 min). Non-transmembrane proteins.

| Acc# | Protein Name | Start | Stop | L_Flank | Peptide Sequence | R_Flank | Multi ProtCut | Peptide Score | SEQ ID NO for Peptide Sequence |
|---|---|---|---|---|---|---|---|---|---|
| | | 115 | 122 | Y | TSVTPVLR | R | * | 28.56 | 158 |
| | | 147 | 162 | R | AQAALQAVNSVQSGNL | L | * | 47.79 | 159 |
| | | 152 | 164 | L | QAVNSVQSGNLAL | L | | 19.99 | 160 |
| | | 261 | 267 | L | TSLNVKY | Y | | 26.11 | 161 |
| | | 298 | 311 | F | GLSVPNVHGALAPL | L | | 23.48 | 162 |
| | | 312 | 325 | L | AIPSAAAAAAAAGR | R | * | 52.36 | 163 |
| | | 314 | 325 | 1 | PSAAAAAAAAGR | R | | 56.48 | 164 |
| | | 419 | 430 | R | EGQEDQGLTKDY | Y | * | 24.27 | 165 |
| Q96DH6 | RNA-binding protein Musashi homolog 2 | 240 | 249 | Y | QFPGFPAAAY | Y | | 29.88 | 166 |
| | | 250 | 261 | Y | GPVAAAAVAAAR | R | * | 83.45 | 167 |
| Q9UER7 | Death domain-associated protein 6 | 165 | 180 | L | SLDPTNAENTASQSPR | R | * | 81.81 | 168 |
| Q5JXB2 | Putative ubiquitin-conjugating enzyme E2 N-like | 131 | 142 | W | KTNEAQAIETAR | R | * | 75.75 | 169 |
| P61088 | Ubiquitin-conjugating enzyme E2 N | 113 | 129 | L | SAPNPDDPLANDVAEQW | W | | 27.41 | 170 |
| | | 130 | 141 | W | KTNEAQAIETAR | R | * | 75.75 | 171 |
| P61163 | Alpha-centractin | 93 | 102 | Y | VYSKDQLQTF | F | | 31.02 | 172 |
| | | 242 | 255 | Y | YLPDGSTIEIGPSR | R | * | 41.99 | 173 |
| | | 243 | 255 | Y | LPDGSTIEIGPSR | R | * | 72.43 | 174 |
| P63010 | AP-2 complex subunit beta | 508 | 520 | L | SLATQDSDNPDLR | R | * | 36.97 | 175 |
| Q9NPI6 | mRNA-decapping enzyme 1A | 190 | 208 | L | SNLGSTETLEEMPSGSQDK | K | * | 61.19 | 176 |
| | | 356 | 368 | L | LNQPVPELSHASL | L | | 27.72 | 177 |
| | | 380 | 397 | L | NVTNTAGTSLPSVDLLQK | K | * | 67.53 | 178 |
| O43852 | Calumenin | 53 | 61 | F | LGAEEAKTF | F | | 46.69 | 179 |
| | | 258 | 271 | W | ILPSDYDHAEAEAR | R | * | 38.88 | 180 |
| | | 298 | 311 | F | VGSQATDFGEALVR | R | * | 64.45 | 181 |
| Q96PK6 | RNA-binding protein 14 | 192 | 203 | F | GNSTGGFDGQAR | R | * | 40.47 | 182 |
| | | 286 | 305 | Y | RGQLASPSSQSAAASSLGPY | Y | | 72.43 | 183 |
| | | 541 | 558 | Y | RGQPGNAYDGAGQPSAAY | Y | | 28.87 | 184 |

TABLE 13

| Proteinase K cleavage specificity, Multiprotease protocol 3. | |
|---|---|
| N-terminal amino acid at cut site | Count |
| L | 112 |
| Q | 100 |
| A | 73 |
| V | 73 |

TABLE 13-continued

Proteinase K cleavage specificity, Multiprotease protocol 3.

| N-terminal amino acid at cut site | Count |
|---|---|
| T | 64 |
| N | 51 |
| M | 47 |
| S | 46 |
| F | 28 |
| H | 27 |
| D | 25 |
| P | 25 |
| G | 22 |
| E | 21 |
| C | 20 |
| Y | 19 |
| I | 16 |
| W | 15 |

The invention claimed is:

1. A method of identifying an epitope on a protein that can be bound by an antibody, said method comprising:
   (i) performing limited or restricted proteolysis on said protein using a single first protease or a combination of first proteases;
   (ii) performing non-limited proteolysis or performing limited or restricted proteolysis on said protein from step (i) using a single second protease or a combination of second proteases, wherein said second protease(s) are all different from the protease(s) used in step (i);
   (iii) analysing peptides which are released from said protein in step (ii) to identify peptides in which one end has been cut by a said first protease and the other end has been cut by a said second protease;
   (iv) probing one or more epitopes in a region of the protein containing or flanking a cut site for a said first protease as identified in step (iii) with one or more antibodies directed to said epitopes, thereby identifying one or more epitopes on the protein that can be bound by one or more of said antibodies.

2. The method of claim 1, wherein in step (ii) non-limited proteolysis is performed.

3. The method of claim 1, wherein a single first protease is used in step (i).

4. The method of claim 1, wherein a single second protease is used in step (ii).

5. The method of claim 1, wherein in step (ii) non-limited proteolysis is performed and wherein said method further comprises, subsequent to step (i), but prior to step (ii), an additional step of performing limited or restricted proteolysis on said protein using said single second protease or a combination of second proteases that is used in step (ii).

6. The method of claim 1, wherein said single first protease or said combination of first proteases is selected from the group consisting of Trypsin, Arg-C, Lys-C and Lys-N.

7. The method of claim 1, wherein said single first protease or said combination of first proteases is selected from the group consisting of pepsin, chymotrypsin and Glu-C.

8. The method of claim 1, wherein said single second protease or said combination of second proteases is selected from the group consisting of pepsin, chymotrypsin and Glu-C.

9. The method of claim 1, wherein said single second protease or said combination of second proteases is selected from the group consisting of Trypsin, Arg-C, Lys-C and Lys-N.

10. The method of claim 1, wherein said method further comprises a denaturation step that is carried out before, during or after step (ii).

11. The method of claim 1, wherein said peptides are analysed using mass spectrometry.

12. The method of claim 1, wherein a plurality of epitopes is probed.

13. The method of claim 1, wherein said method further comprises a step prior to step (iv) of generating one or more isolated epitopes having sequences that correspond to one or more epitopes on said protein that are in a region of the protein containing or flanking a cut site for a said first protease as identified in step (iii), and generating antibodies that are directed to said isolated epitopes, and using said antibodies in step (iv) for probing one or more epitopes on said protein.

14. The method of claim 1, wherein said epitope is within 20 amino acids of said cut site for a said first protease.

15. The method of claim 1, wherein a plurality of epitopes is probed and wherein said plurality of epitopes is a set of epitopes wherein the sequence of each epitope in the set is offset from another epitope in the set by 1, 2 or 3 amino acids.

16. The method of claim 1, wherein the proteolysis in steps (i) and (ii) is performed on a protein that is present in a proteoliposome that is derived from cells.

17. The method of claim 16, wherein said proteoliposome is immobilized in a flow cell to create a stationary phase of the protein.

18. The method of claim 1, wherein step (iii) comprises analysing peptides which are released from said protein in step (i) and step (ii).

19. The method of claim 1, wherein said method further comprises a step of producing an antibody against an epitope identified by said method.

* * * * *

SEQUENCE LISTING

<160> NUMBER OF SEQ ID NOS: 184

<210> SEQ ID NO 1
<211> LENGTH: 839
<212> TYPE: PRT
<213> ORGANISM: Homo sapiens

<400> SEQUENCE: 1

```
Met Lys Lys Trp Ser Ser Thr Asp Leu Gly Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270
```

-continued

```
Trp Gln Thr Ala Asp Ile Ser Ala Arg Asp Ser Val Gly Asn Thr Val
    275                 280                 285

Leu His Ala Leu Val Glu Val Ala Asp Asn Thr Ala Asp Asn Thr Lys
290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
                340                 345                 350

Ile Leu Gln Arg Glu Ile Gln Pro Glu Cys Arg His Leu Ser Arg
    355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
            435                 440                 445

Phe Thr Met Ala Ala Tyr Tyr Arg Pro Val Asp Gly Leu Pro Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
            515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
                595                 600                 605

Ser Glu Ser Thr Ser His Arg Trp Arg Gly Pro Ala Cys Arg Pro Pro
    610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
                660                 665                 670

Ile Leu Leu Leu Asn Met Leu Ile Ala Leu Met Gly Glu Thr Val Asn
            675                 680                 685
```

```
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Val Tyr Leu Arg
                805                 810                 815
Gln Phe Ser Gly Ser Leu Lys Pro Glu Asp Ala Glu Val Phe Lys Ser
                820                 825                 830
Pro Ala Ala Ser Gly Glu Lys
        835

<210> SEQ ID NO 2
<211> LENGTH: 13
<212> TYPE: PRT
<213> ORGANISM: Artificial Sequence
<220> FEATURE:
<223> OTHER INFORMATION: peptide sequence

<400> SEQUENCE: 2

Leu Leu Ser Gln Asp Ser Val Ala Ala Ser Thr Glu Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: peptide sequence

<400> SEQUENCE: 3

Leu Leu Ser Gln Asp Ser Val Ala Ala Ser Thr Glu Lys Thr Leu Arg
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: peptide sequence

<400> SEQUENCE: 4

Gln Phe Ser Gly Ser Leu Lys Pro Glu Asp Ala Glu Val Phe Lys Ser
1               5                   10                  15

Pro Ala Ala Ser Gly Glu Lys
            20

<210> SEQ ID NO 5
<211> LENGTH: 22
<212> TYPE: PRT
<213> ORGANISM: Artificial Sequence
<220> FEATURE:
<223> OTHER INFORMATION: peptide sequence
```

```
<400> SEQUENCE: 5

Leu Leu Ser Gln Asp Ser Val Ala Ala Ser Thr Glu Lys Thr Leu Arg
1               5                   10                  15

Leu Tyr Asp Arg Arg Ser
            20

<210> SEQ ID NO 6
<211> LENGTH: 15
<212> TYPE: PRT
<213> ORGANISM: Artificial Sequence
<220> FEATURE:
<223> OTHER INFORMATION: peptide sequence

<400> SEQUENCE: 6

Gly Arg His Trp Lys Asn Phe Ala Leu Val Pro Leu Leu Arg Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: peptide sequence

<400> SEQUENCE: 7

Leu Val Glu Asn Gly Ala Asp Val Gln Ala Ala His Gly Asp Phe
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: peptide sequence

<400> SEQUENCE: 8

Asp Gly Pro Thr Gly Ala Arg Leu Leu Ser Gln
1               5                   10

<210> SEQ ID NO 9
<211> LENGTH: 14
<212> TYPE: PRT
<213> ORGANISM: Artificial Sequence
<220> FEATURE:
<223> OTHER INFORMATION: peptide sequence

<400> SEQUENCE: 9

Asp Ala Glu Val Phe Lys Ser Pro Ala Ala Ser Gly Glu Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: peptide sequence

<400> SEQUENCE: 10

Ser Gln Asp Ser Val Ala Ala Ser Thr Glu Lys Thr Leu
1               5                   10

<210> SEQ ID NO 11
<211> LENGTH: 12
<212> TYPE: PRT
<213> ORGANISM: Artificial Sequence
```

```
<220> FEATURE:
<223> OTHER INFORMATION: peptide sequence

<400> SEQUENCE: 11

Ser Gly Ser Leu Lys Pro Glu Asp Ala Glu Val Phe
1               5                   10

<210> SEQ ID NO 12
<211> LENGTH: 12
<212> TYPE: PRT
<213> ORGANISM: Artificial Sequence
<220> FEATURE:
<223> OTHER INFORMATION: peptide sequence

<400> SEQUENCE: 12

Val Ser Pro Val Ile Thr Ile Gln Arg Pro Gly Asp
1               5                   10

<210> SEQ ID NO 13
<211> LENGTH: 17
<212> TYPE: PRT
<213> ORGANISM: Artificial Sequence
<220> FEATURE:
<223> OTHER INFORMATION: peptide sequence

<400> SEQUENCE: 13

Val Ser Pro Val Ile Thr Ile Gln Arg Pro Gly Asp Gly Pro Thr Gly
1               5                   10                  15

Ala

<210> SEQ ID NO 14
<211> LENGTH: 15
<212> TYPE: PRT
<213> ORGANISM: Artificial Sequence
<220> FEATURE:
<223> OTHER INFORMATION: peptide sequence

<400> SEQUENCE: 14

Leu Asn Leu His Asp Gly Gln Asn Thr Thr Ile Pro Leu Leu Leu
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: peptide sequence

<400> SEQUENCE: 15

Tyr Thr Asp Ser Tyr Tyr Lys Gly Gln
1               5

<210> SEQ ID NO 16
<211> LENGTH: 9
<212> TYPE: PRT
<213> ORGANISM: Artificial Sequence
<220> FEATURE:
<223> OTHER INFORMATION: peptide sequence

<400> SEQUENCE: 16

Ser Leu Pro Ser Glu Ser Thr Ser His
1               5

<210> SEQ ID NO 17
<211> LENGTH: 11
<212> TYPE: PRT
```

<213> ORGANISM: Artificial Sequence
<220> FEATURE:
<223> OTHER INFORMATION: peptide sequence

<400> SEQUENCE: 17

Glu Asp Pro Gly Asn Cys Glu Gly Val Lys Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide sequence

<400> SEQUENCE: 18

Asp Arg Gln Ser Ala Gln Pro Glu Glu Val Tyr Leu Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: peptide sequence

<400> SEQUENCE: 19

Gln Ser Ala Gln Pro Glu Glu Val Tyr Leu Arg
1               5                   10

<210> SEQ ID NO 20
<211> LENGTH: 16
<212> TYPE: PRT
<213> ORGANISM: Artificial Sequence
<220> FEATURE:
<223> OTHER INFORMATION: peptide sequence

<400> SEQUENCE: 20

Phe Ala Pro Gln Ile Arg Val Asn Leu Asn Tyr Arg Lys Gly Thr Gly
1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: peptide sequence

<400> SEQUENCE: 21

Ala Ser Gln Pro Asp Pro Asn Arg Phe Asp Arg Asp Arg
1               5                   10

<210> SEQ ID NO 22
<211> LENGTH: 15
<212> TYPE: PRT
<213> ORGANISM: Artificial Sequence
<220> FEATURE:
<223> OTHER INFORMATION: peptide sequence

<400> SEQUENCE: 22

Leu Asn Leu Lys Asp Gly Val Asn Ala Cys Ile Leu Pro Leu Leu
1               5                   10                  15

<210> SEQ ID NO 23
<211> LENGTH: 9
<212> TYPE: PRT
<213> ORGANISM: Artificial Sequence
<220> FEATURE:
<223> OTHER INFORMATION: peptide sequence

<400> SEQUENCE: 23

Cys Thr Asp Asp Tyr Tyr Arg Gly His
1               5

<210> SEQ ID NO 24
<211> LENGTH: 16
<212> TYPE: PRT
<213> ORGANISM: Artificial Sequence
<220> FEATURE:
<223> OTHER INFORMATION: peptide sequence

<400> SEQUENCE: 24

Leu Val Glu Asn Gly Ala Asn Val His Ala Arg Ala Cys Gly Arg Phe
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: peptide sequence

<400> SEQUENCE: 25

Glu Asp Pro Ser Gly Ala Gly Val Pro Arg
1               5                   10

<210> SEQ ID NO 26
<211> LENGTH: 15
<212> TYPE: PRT
<213> ORGANISM: Artificial Sequence
<220> FEATURE:
<223> OTHER INFORMATION: peptide sequence

<400> SEQUENCE: 26

Gly Ala Ser Glu Glu Asn Tyr Val Pro Val Gln Leu Leu Gln Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: peptide sequence

<400> SEQUENCE: 27

Trp Ser Ser Thr Asp Leu Gly Ala Ala Ala Asp Pro Leu Gln Lys
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: peptide sequence

<400> SEQUENCE: 28

Leu Leu Ser Gln Asp Ser Val Ala Ala Ser Thr Glu Lys
1               5                   10

<210> SEQ ID NO 29
<211> LENGTH: 16
<212> TYPE: PRT
<213> ORGANISM: Artificial Sequence
<220> FEATURE:

<223> OTHER INFORMATION: peptide sequence

<400> SEQUENCE: 29

Leu Leu Ser Gln Asp Ser Val Ala Ala Ser Thr Glu Lys Thr Leu Arg
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: peptide sequence

<400> SEQUENCE: 30

Ala Met Leu Asn Leu His Asp Gly Gln Asn Thr Thr Ile Pro Leu Leu
1               5                   10                  15

Leu Glu Ile Ala Arg
            20

<210> SEQ ID NO 31
<211> LENGTH: 19
<212> TYPE: PRT
<213> ORGANISM: Artificial Sequence
<220> FEATURE:
<223> OTHER INFORMATION: peptide sequence

<400> SEQUENCE: 31

Gln Thr Asp Ser Leu Lys Glu Leu Val Asn Ala Ser Tyr Thr Asp Ser
1               5                   10                  15

Tyr Tyr Lys

<210> SEQ ID NO 32
<211> LENGTH: 11
<212> TYPE: PRT
<213> ORGANISM: Artificial Sequence
<220> FEATURE:
<223> OTHER INFORMATION: peptide sequence

<400> SEQUENCE: 32

Gly Gln Thr Ala Leu His Ile Ala Ile Glu Arg
1               5                   10

<210> SEQ ID NO 33
<211> LENGTH: 26
<212> TYPE: PRT
<213> ORGANISM: Artificial Sequence
<220> FEATURE:
<223> OTHER INFORMATION: peptide sequence

<400> SEQUENCE: 33

Asn Met Ala Leu Val Thr Leu Leu Val Glu Asn Gly Ala Asp Val Gln
1               5                   10                  15

Ala Ala Ala His Gly Asp Phe Phe Lys Lys
            20                  25

<210> SEQ ID NO 34
<211> LENGTH: 15
<212> TYPE: PRT
<213> ORGANISM: Artificial Sequence
<220> FEATURE:
<223> OTHER INFORMATION: peptide sequence

<400> SEQUENCE: 34

Phe Leu Leu Gln Asn Ser Trp Gln Thr Ala Asp Ile Ser Ala Arg
1               5                   10                  15

<210> SEQ ID NO 35
<211> LENGTH: 23
<212> TYPE: PRT
<213> ORGANISM: Artificial Sequence
<220> FEATURE:
<223> OTHER INFORMATION: peptide sequence

<400> SEQUENCE: 35

Asp Ser Val Gly Asn Thr Val Leu His Ala Leu Val Glu Val Ala Asp
1               5                   10                  15

Asn Thr Ala Asp Asn Thr Lys
            20

<210> SEQ ID NO 36
<211> LENGTH: 13
<212> TYPE: PRT
<213> ORGANISM: Artificial Sequence
<220> FEATURE:
<223> OTHER INFORMATION: peptide sequence

<400> SEQUENCE: 36

Leu His Pro Thr Leu Lys Leu Glu Glu Leu Thr Asn Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: peptide sequence

<400> SEQUENCE: 37

Lys Gly Met Thr Pro Leu Ala Leu Ala Ala Gly Thr Gly Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: peptide sequence

<400> SEQUENCE: 38

Gly Met Thr Pro Leu Ala Leu Ala Ala Gly Thr Gly Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: peptide sequence

<400> SEQUENCE: 39

Ile Gly Val Leu Ala Tyr Ile Leu Gln Arg
1               5                   10

<210> SEQ ID NO 40
<211> LENGTH: 9
<212> TYPE: PRT
<213> ORGANISM: Artificial Sequence
<220> FEATURE:
<223> OTHER INFORMATION: peptide sequence

```
<400> SEQUENCE: 40

Ala Ile Thr Ile Leu Asp Thr Glu Lys
1               5

<210> SEQ ID NO 41
<211> LENGTH: 7
<212> TYPE: PRT
<213> ORGANISM: Artificial Sequence
<220> FEATURE:
<223> OTHER INFORMATION: peptide sequence

<400> SEQUENCE: 41

Thr Leu Ser Phe Ser Leu Arg
1               5

<210> SEQ ID NO 42
<211> LENGTH: 9
<212> TYPE: PRT
<213> ORGANISM: Artificial Sequence
<220> FEATURE:
<223> OTHER INFORMATION: peptide sequence

<400> SEQUENCE: 42

Asn Phe Ala Leu Val Pro Leu Leu Arg
1               5

<210> SEQ ID NO 43
<211> LENGTH: 18
<212> TYPE: PRT
<213> ORGANISM: Artificial Sequence
<220> FEATURE:
<223> OTHER INFORMATION: peptide sequence

<400> SEQUENCE: 43

Glu Ala Ser Ala Arg Asp Arg Gln Ser Ala Gln Pro Glu Glu Val Tyr
1               5                   10                  15

Leu Arg

<210> SEQ ID NO 44
<211> LENGTH: 13
<212> TYPE: PRT
<213> ORGANISM: Artificial Sequence
<220> FEATURE:
<223> OTHER INFORMATION: peptide sequence

<400> SEQUENCE: 44

Asp Arg Gln Ser Ala Gln Pro Glu Glu Val Tyr Leu Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: peptide sequence

<400> SEQUENCE: 45

Gln Ser Ala Gln Pro Glu Glu Val Tyr Leu Arg
1               5                   10

<210> SEQ ID NO 46
<211> LENGTH: 15
<212> TYPE: PRT
<213> ORGANISM: Artificial Sequence
<220> FEATURE:
```

<223> OTHER INFORMATION: peptide sequence

<400> SEQUENCE: 46

Gln Phe Ser Gly Ser Leu Lys Pro Glu Asp Ala Glu Val Phe Lys
1               5                   10                  15

<210> SEQ ID NO 47
<211> LENGTH: 23
<212> TYPE: PRT
<213> ORGANISM: Artificial Sequence
<220> FEATURE:
<223> OTHER INFORMATION: peptide sequence

<400> SEQUENCE: 47

Gln Phe Ser Gly Ser Leu Lys Pro Glu Asp Ala Glu Val Phe Lys Ser
1               5                   10                  15

Pro Ala Ala Ser Gly Glu Lys
            20

<210> SEQ ID NO 48
<211> LENGTH: 11
<212> TYPE: PRT
<213> ORGANISM: Artificial Sequence
<220> FEATURE:
<223> OTHER INFORMATION: peptide sequence

<400> SEQUENCE: 48

Asp Gly Pro Thr Gly Ala Arg Leu Leu Ser Gln
1               5                   10

<210> SEQ ID NO 49
<211> LENGTH: 14
<212> TYPE: PRT
<213> ORGANISM: Artificial Sequence
<220> FEATURE:
<223> OTHER INFORMATION: peptide sequence

<400> SEQUENCE: 49

Asp Ser Val Ala Ala Ser Thr Glu Lys Thr Leu Arg Leu Tyr
1               5                   10

<210> SEQ ID NO 50
<211> LENGTH: 17
<212> TYPE: PRT
<213> ORGANISM: Artificial Sequence
<220> FEATURE:
<223> OTHER INFORMATION: peptide sequence

<400> SEQUENCE: 50

Asp Gly Gln Asn Thr Thr Ile Pro Leu Leu Leu Glu Ile Ala Arg Gln
1               5                   10                  15

Thr

<210> SEQ ID NO 51
<211> LENGTH: 12
<212> TYPE: PRT
<213> ORGANISM: Artificial Sequence
<220> FEATURE:
<223> OTHER INFORMATION: peptide sequence

<400> SEQUENCE: 51

Asp Ser Leu Lys Glu Leu Val Asn Ala Ser Tyr Thr
1               5                   10

<210> SEQ ID NO 52

```
<211> LENGTH: 15
<212> TYPE: PRT
<213> ORGANISM: Artificial Sequence
<220> FEATURE:
<223> OTHER INFORMATION: peptide sequence

<400> SEQUENCE: 52

Asp Ser Val Gly Asn Thr Val Leu His Ala Leu Val Glu Val Ala
1               5                   10                  15

<210> SEQ ID NO 53
<211> LENGTH: 14
<212> TYPE: PRT
<213> ORGANISM: Artificial Sequence
<220> FEATURE:
<223> OTHER INFORMATION: peptide sequence

<400> SEQUENCE: 53

Asp Ala Glu Val Phe Lys Ser Pro Ala Ala Ser Gly Glu Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: peptide sequence

<400> SEQUENCE: 54

Leu Ser Gln Asp Ser Val Ala Ala Ser Thr Glu Lys Thr Leu
1               5                   10

<210> SEQ ID NO 55
<211> LENGTH: 13
<212> TYPE: PRT
<213> ORGANISM: Artificial Sequence
<220> FEATURE:
<223> OTHER INFORMATION: peptide sequence

<400> SEQUENCE: 55

Ser Gln Asp Ser Val Ala Ala Ser Thr Glu Lys Thr Leu
1               5                   10

<210> SEQ ID NO 56
<211> LENGTH: 16
<212> TYPE: PRT
<213> ORGANISM: Artificial Sequence
<220> FEATURE:
<223> OTHER INFORMATION: peptide sequence

<400> SEQUENCE: 56

Ser Gln Asp Ser Val Ala Ala Ser Thr Glu Lys Thr Leu Arg Leu Tyr
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: peptide sequence

<400> SEQUENCE: 57

Asn Leu His Asp Gly Gln Asn Thr Thr Ile Pro Leu
1               5                   10

<210> SEQ ID NO 58
<211> LENGTH: 17
```

```
<212> TYPE: PRT
<213> ORGANISM: Artificial Sequence
<220> FEATURE:
<223> OTHER INFORMATION: peptide sequence

<400> SEQUENCE: 58

Leu Val Glu Asn Gly Ala Asp Val Gln Ala Ala His Gly Asp Phe
1               5                   10                  15

Phe

<210> SEQ ID NO 59
<211> LENGTH: 16
<212> TYPE: PRT
<213> ORGANISM: Artificial Sequence
<220> FEATURE:
<223> OTHER INFORMATION: peptide sequence

<400> SEQUENCE: 59

Gln Thr Ala Asp Ile Ser Ala Arg Asp Ser Val Gly Asn Thr Val Leu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: peptide sequence

<400> SEQUENCE: 60

His Ala Leu Val Glu Val Ala Asp Asn Thr Ala Asp Asn Thr Lys Phe
1               5                   10                  15

<210> SEQ ID NO 61
<211> LENGTH: 12
<212> TYPE: PRT
<213> ORGANISM: Artificial Sequence
<220> FEATURE:
<223> OTHER INFORMATION: peptide sequence

<400> SEQUENCE: 61

Ala Ala Gly Thr Gly Lys Ile Gly Val Leu Ala Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: peptide sequence

<400> SEQUENCE: 62

Ser Gly Ser Leu Lys Pro Glu Asp Ala Glu Val Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: peptide sequence

<400> SEQUENCE: 63

Phe Gly Lys Gly Asp Ser Glu Glu Ala Phe
1               5                   10

<210> SEQ ID NO 64
```

```
<211> LENGTH: 11
<212> TYPE: PRT
<213> ORGANISM: Artificial Sequence
<220> FEATURE:
<223> OTHER INFORMATION: peptide sequence

<400> SEQUENCE: 64

His Asp Gly Gln Asn Thr Thr Ile Pro Leu Leu
1               5                   10

<210> SEQ ID NO 65
<211> LENGTH: 16
<212> TYPE: PRT
<213> ORGANISM: Artificial Sequence
<220> FEATURE:
<223> OTHER INFORMATION: peptide sequence

<400> SEQUENCE: 65

Leu Val Glu Asn Gly Ala Asp Val Gln Ala Ala Ala His Gly Asp Phe
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: peptide sequence

<400> SEQUENCE: 66

Val Glu Asn Gly Ala Asp Val Gln Ala Ala Ala His Gly Asp Phe
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: peptide sequence

<400> SEQUENCE: 67

Val Glu Asn Gly Ala Asp Val Gln Ala Ala Ala His Gly Asp Phe
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: peptide sequence

<400> SEQUENCE: 68

His Ala Leu Val Glu Val Ala Asp Asn Thr Ala Asp Asn Thr Lys Phe
1               5                   10                  15

<210> SEQ ID NO 69
<211> LENGTH: 13
<212> TYPE: PRT
<213> ORGANISM: Artificial Sequence
<220> FEATURE:
<223> OTHER INFORMATION: peptide sequence

<400> SEQUENCE: 69

Val Glu Val Ala Asp Asn Thr Ala Asp Asn Thr Lys Phe
1               5                   10

<210> SEQ ID NO 70
<211> LENGTH: 17
```

```
<212> TYPE: PRT
<213> ORGANISM: Artificial Sequence
<220> FEATURE:
<223> OTHER INFORMATION: peptide sequence

<400> SEQUENCE: 70

Glu Val Ile Ala Tyr Ser Ser Ser Glu Thr Pro Asn Arg His Asp Met
1               5                   10                  15

Leu

<210> SEQ ID NO 71
<211> LENGTH: 17
<212> TYPE: PRT
<213> ORGANISM: Artificial Sequence
<220> FEATURE:
<223> OTHER INFORMATION: peptide sequence

<400> SEQUENCE: 71

Val Ser Pro Val Ile Thr Ile Gln Arg Pro Gly Asp Gly Pro Thr Gly
1               5                   10                  15

Ala

<210> SEQ ID NO 72
<211> LENGTH: 12
<212> TYPE: PRT
<213> ORGANISM: Artificial Sequence
<220> FEATURE:
<223> OTHER INFORMATION: peptide sequence

<400> SEQUENCE: 72

Ile Gln Arg Pro Gly Asp Gly Pro Thr Gly Ala Arg
1               5                   10

<210> SEQ ID NO 73
<211> LENGTH: 12
<212> TYPE: PRT
<213> ORGANISM: Artificial Sequence
<220> FEATURE:
<223> OTHER INFORMATION: peptide sequence

<400> SEQUENCE: 73

Arg Pro Gly Asp Gly Pro Thr Gly Ala Arg Leu Leu
1               5                   10

<210> SEQ ID NO 74
<211> LENGTH: 15
<212> TYPE: PRT
<213> ORGANISM: Artificial Sequence
<220> FEATURE:
<223> OTHER INFORMATION: peptide sequence

<400> SEQUENCE: 74

Leu Asn Leu His Asp Gly Gln Asn Thr Thr Ile Pro Leu Leu Leu
1               5                   10                  15

<210> SEQ ID NO 75
<211> LENGTH: 8
<212> TYPE: PRT
<213> ORGANISM: Artificial Sequence
<220> FEATURE:
<223> OTHER INFORMATION: peptide sequence

<400> SEQUENCE: 75

Asp Thr Glu Lys Ser Phe Leu Lys
1               5
```

<210> SEQ ID NO 76
<211> LENGTH: 11
<212> TYPE: PRT
<213> ORGANISM: Artificial Sequence
<220> FEATURE:
<223> OTHER INFORMATION: peptide sequence

<400> SEQUENCE: 76

Glu Asp Pro Gly Asn Cys Glu Gly Val Lys Arg
1               5                   10

<210> SEQ ID NO 77
<211> LENGTH: 12
<212> TYPE: PRT
<213> ORGANISM: Artificial Sequence
<220> FEATURE:
<223> OTHER INFORMATION: peptide sequence

<400> SEQUENCE: 77

Glu Asp Pro Gly Asn Cys Glu Gly Val Lys Arg Thr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: peptide sequence

<400> SEQUENCE: 78

Glu Asp Pro Gly Asn Cys Glu Gly Val Lys Arg Thr Leu
1               5                   10

<210> SEQ ID NO 79
<211> LENGTH: 16
<212> TYPE: PRT
<213> ORGANISM: Artificial Sequence
<220> FEATURE:
<223> OTHER INFORMATION: peptide sequence

<400> SEQUENCE: 79

Ser Ala Arg Asp Arg Gln Ser Ala Gln Pro Glu Glu Val Tyr Leu Arg
1               5                   10                  15

<210> SEQ ID NO 80
<211> LENGTH: 13
<212> TYPE: PRT
<213> ORGANISM: Artificial Sequence
<220> FEATURE:
<223> OTHER INFORMATION: peptide sequence

<400> SEQUENCE: 80

Asp Arg Gln Ser Ala Gln Pro Glu Glu Val Tyr Leu Arg
1               5                   10

<210> SEQ ID NO 81
<211> LENGTH: 11
<212> TYPE: PRT
<213> ORGANISM: Artificial Sequence
<220> FEATURE:
<223> OTHER INFORMATION: peptide sequence

<400> SEQUENCE: 81

Gln Ser Ala Gln Pro Glu Glu Val Tyr Leu Arg
1               5                   10

```
<210> SEQ ID NO 82
<211> LENGTH: 18
<212> TYPE: PRT
<213> ORGANISM: Artificial Sequence
<220> FEATURE:
<223> OTHER INFORMATION: peptide sequence

<400> SEQUENCE: 82

Ser Ser Pro Ala Gly Gly Val Leu Gly Gly Gly Leu Gly Gly Gly Gly
1               5                   10                  15
Gly Arg

<210> SEQ ID NO 83
<211> LENGTH: 11
<212> TYPE: PRT
<213> ORGANISM: Artificial Sequence
<220> FEATURE:
<223> OTHER INFORMATION: peptide sequence

<400> SEQUENCE: 83

Phe Asp Gly Gly Val Glu Ala Ile Ala Thr Arg
1               5                   10

<210> SEQ ID NO 84
<211> LENGTH: 14
<212> TYPE: PRT
<213> ORGANISM: Artificial Sequence
<220> FEATURE:
<223> OTHER INFORMATION: peptide sequence

<400> SEQUENCE: 84

Glu Lys Asp Ile Leu Thr Ala Ile Ala Ala Asp Leu Cys Lys
1               5                   10

<210> SEQ ID NO 85
<211> LENGTH: 14
<212> TYPE: PRT
<213> ORGANISM: Artificial Sequence
<220> FEATURE:
<223> OTHER INFORMATION: peptide sequence

<400> SEQUENCE: 85

Phe Asp His Ile Phe Tyr Thr Gly Asn Thr Ala Val Gly Lys
1               5                   10

<210> SEQ ID NO 86
<211> LENGTH: 9
<212> TYPE: PRT
<213> ORGANISM: Artificial Sequence
<220> FEATURE:
<223> OTHER INFORMATION: peptide sequence

<400> SEQUENCE: 86

Ile Leu Ser Leu Leu Glu Gly Gln Lys
1               5

<210> SEQ ID NO 87
<211> LENGTH: 12
<212> TYPE: PRT
<213> ORGANISM: Artificial Sequence
<220> FEATURE:
<223> OTHER INFORMATION: peptide sequence

<400> SEQUENCE: 87

Ile Ala Phe Gly Gly Glu Thr Asp Glu Ala Thr Arg
1               5                   10
```

```
<210> SEQ ID NO 88
<211> LENGTH: 13
<212> TYPE: PRT
<213> ORGANISM: Artificial Sequence
<220> FEATURE:
<223> OTHER INFORMATION: peptide sequence

<400> SEQUENCE: 88

Ile Ala Phe Gly Gly Glu Thr Asp Glu Ala Thr Arg Tyr
1               5                   10

<210> SEQ ID NO 89
<211> LENGTH: 13
<212> TYPE: PRT
<213> ORGANISM: Artificial Sequence
<220> FEATURE:
<223> OTHER INFORMATION: peptide sequence

<400> SEQUENCE: 89

Tyr Ile Ala Pro Thr Val Leu Thr Asp Val Asp Pro Lys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: peptide sequence

<400> SEQUENCE: 90

Ile Ala Pro Thr Val Leu Thr Asp Val Asp Pro Lys
1               5                   10

<210> SEQ ID NO 91
<211> LENGTH: 17
<212> TYPE: PRT
<213> ORGANISM: Artificial Sequence
<220> FEATURE:
<223> OTHER INFORMATION: peptide sequence

<400> SEQUENCE: 91

Val Met Gln Glu Glu Ile Phe Gly Pro Ile Leu Pro Ile Val Pro Val
1               5                   10                  15

Lys

<210> SEQ ID NO 92
<211> LENGTH: 12
<212> TYPE: PRT
<213> ORGANISM: Artificial Sequence
<220> FEATURE:
<223> OTHER INFORMATION: peptide sequence

<400> SEQUENCE: 92

Asn Val Asp Glu Ala Ile Asn Phe Ile Asn Glu Arg
1               5                   10

<210> SEQ ID NO 93
<211> LENGTH: 20
<212> TYPE: PRT
<213> ORGANISM: Artificial Sequence
<220> FEATURE:
<223> OTHER INFORMATION: peptide sequence

<400> SEQUENCE: 93

Gln Phe Tyr Asp Gln Ala Leu Gln Gln Ala Val Val Asp Asp Asp Ala
1               5                   10                  15
```

Asn Asn Ala Lys
        20

<210> SEQ ID NO 94
<211> LENGTH: 14
<212> TYPE: PRT
<213> ORGANISM: Artificial Sequence
<220> FEATURE:
<223> OTHER INFORMATION: peptide sequence

<400> SEQUENCE: 94

Thr Phe His Glu Thr Leu Asp Cys Cys Gly Ser Ser Thr Leu
1               5                   10

<210> SEQ ID NO 95
<211> LENGTH: 7
<212> TYPE: PRT
<213> ORGANISM: Artificial Sequence
<220> FEATURE:
<223> OTHER INFORMATION: peptide sequence

<400> SEQUENCE: 95

Ile Val Leu Ser Tyr Val Arg
1               5

<210> SEQ ID NO 96
<211> LENGTH: 24
<212> TYPE: PRT
<213> ORGANISM: Artificial Sequence
<220> FEATURE:
<223> OTHER INFORMATION: peptide sequence

<400> SEQUENCE: 96

Gly Ile Ser Gly Glu Lys Asp Val Ser Pro Asp Leu Ser Cys Ala Asp
1               5                   10                  15

Glu Ile Ser Glu Cys Tyr His Lys
        20

<210> SEQ ID NO 97
<211> LENGTH: 8
<212> TYPE: PRT
<213> ORGANISM: Artificial Sequence
<220> FEATURE:
<223> OTHER INFORMATION: peptide sequence

<400> SEQUENCE: 97

Glu Thr Leu Leu Glu Ile Gln Lys
1               5

<210> SEQ ID NO 98
<211> LENGTH: 11
<212> TYPE: PRT
<213> ORGANISM: Artificial Sequence
<220> FEATURE:
<223> OTHER INFORMATION: peptide sequence

<400> SEQUENCE: 98

Gly Gln Met Gly Pro Thr Glu Gln Gly Pro Tyr
1               5                   10

<210> SEQ ID NO 99
<211> LENGTH: 8
<212> TYPE: PRT
<213> ORGANISM: Artificial Sequence
<220> FEATURE:
<223> OTHER INFORMATION: peptide sequence

```
<400> SEQUENCE: 99

Leu Cys Leu Leu Pro Leu Val Arg
1               5

<210> SEQ ID NO 100
<211> LENGTH: 11
<212> TYPE: PRT
<213> ORGANISM: Artificial Sequence
<220> FEATURE:
<223> OTHER INFORMATION: peptide sequence

<400> SEQUENCE: 100

Ala Trp Asp Asp Phe Phe Pro Gly Ser Asp Arg
1               5                   10

<210> SEQ ID NO 101
<211> LENGTH: 19
<212> TYPE: PRT
<213> ORGANISM: Artificial Sequence
<220> FEATURE:
<223> OTHER INFORMATION: peptide sequence

<400> SEQUENCE: 101

Thr Pro Met Gly Ile Val Leu Asp Ala Leu Glu Gln Gln Glu Glu Gly
1               5                   10                  15

Ile Asn Arg

<210> SEQ ID NO 102
<211> LENGTH: 12
<212> TYPE: PRT
<213> ORGANISM: Artificial Sequence
<220> FEATURE:
<223> OTHER INFORMATION: peptide sequence

<400> SEQUENCE: 102

Asp Ala Leu Glu Gln Gln Glu Glu Gly Ile Asn Arg
1               5                   10

<210> SEQ ID NO 103
<211> LENGTH: 7
<212> TYPE: PRT
<213> ORGANISM: Artificial Sequence
<220> FEATURE:
<223> OTHER INFORMATION: peptide sequence

<400> SEQUENCE: 103

Leu Thr Asp Tyr Ile Ser Lys
1               5

<210> SEQ ID NO 104
<211> LENGTH: 11
<212> TYPE: PRT
<213> ORGANISM: Artificial Sequence
<220> FEATURE:
<223> OTHER INFORMATION: peptide sequence

<400> SEQUENCE: 104

Thr Val Leu Trp Gly Leu Gly Val Leu Ile Arg
1               5                   10

<210> SEQ ID NO 105
<211> LENGTH: 12
<212> TYPE: PRT
<213> ORGANISM: Artificial Sequence
<220> FEATURE:
```

<223> OTHER INFORMATION: peptide sequence

<400> SEQUENCE: 105

Glu Ala Asp Glu Asp Ala Val Gln Phe Ala Asn Arg
1               5                   10

<210> SEQ ID NO 106
<211> LENGTH: 15
<212> TYPE: PRT
<213> ORGANISM: Artificial Sequence
<220> FEATURE:
<223> OTHER INFORMATION: peptide sequence

<400> SEQUENCE: 106

Gln Gly Gly Leu Val Asp Leu Leu Trp Asp Gly Gly Leu Lys Arg
1               5                   10                  15

<210> SEQ ID NO 107
<211> LENGTH: 10
<212> TYPE: PRT
<213> ORGANISM: Artificial Sequence
<220> FEATURE:
<223> OTHER INFORMATION: peptide sequence

<400> SEQUENCE: 107

Val Ile Asp Asn Gly Ser Gly Met Cys Lys
1               5                   10

<210> SEQ ID NO 108
<211> LENGTH: 10
<212> TYPE: PRT
<213> ORGANISM: Artificial Sequence
<220> FEATURE:
<223> OTHER INFORMATION: peptide sequence

<400> SEQUENCE: 108

Ala Gly Phe Ala Gly Asp Asp Ala Pro Arg
1               5                   10

<210> SEQ ID NO 109
<211> LENGTH: 9
<212> TYPE: PRT
<213> ORGANISM: Artificial Sequence
<220> FEATURE:
<223> OTHER INFORMATION: peptide sequence

<400> SEQUENCE: 109

Ala Val Phe Pro Ser Ile Val Gly Arg
1               5

<210> SEQ ID NO 110
<211> LENGTH: 8
<212> TYPE: PRT
<213> ORGANISM: Artificial Sequence
<220> FEATURE:
<223> OTHER INFORMATION: peptide sequence

<400> SEQUENCE: 110

Pro Ser Ile Val Gly Arg Pro Arg
1               5

<210> SEQ ID NO 111
<211> LENGTH: 11
<212> TYPE: PRT
<213> ORGANISM: Artificial Sequence
<220> FEATURE:
<223> OTHER INFORMATION: peptide sequence

<400> SEQUENCE: 111

Ile Trp His His Thr Phe Tyr Asn Glu Leu Arg
1               5                   10

<210> SEQ ID NO 112
<211> LENGTH: 14
<212> TYPE: PRT
<213> ORGANISM: Artificial Sequence
<220> FEATURE:
<223> OTHER INFORMATION: peptide sequence

<400> SEQUENCE: 112

Thr Thr Gly Ile Val Met Asp Ser Gly Asp Gly Val Thr His
1               5                   10

<210> SEQ ID NO 113
<211> LENGTH: 16
<212> TYPE: PRT
<213> ORGANISM: Artificial Sequence
<220> FEATURE:
<223> OTHER INFORMATION: peptide sequence

<400> SEQUENCE: 113

Ser Tyr Glu Leu Pro Asp Gly Gln Val Ile Thr Ile Gly Asn Glu Arg
1               5                   10                  15

<210> SEQ ID NO 114
<211> LENGTH: 14
<212> TYPE: PRT
<213> ORGANISM: Artificial Sequence
<220> FEATURE:
<223> OTHER INFORMATION: peptide sequence

<400> SEQUENCE: 114

Glu Leu Pro Asp Gly Gln Val Ile Thr Ile Gly Asn Glu Arg
1               5                   10

<210> SEQ ID NO 115
<211> LENGTH: 16
<212> TYPE: PRT
<213> ORGANISM: Artificial Sequence
<220> FEATURE:
<223> OTHER INFORMATION: peptide sequence

<400> SEQUENCE: 115

Ile Ser Lys Gln Glu Tyr Asp Glu Ser Gly Pro Ser Ile Val His Arg
1               5                   10                  15

<210> SEQ ID NO 116
<211> LENGTH: 12
<212> TYPE: PRT
<213> ORGANISM: Artificial Sequence
<220> FEATURE:
<223> OTHER INFORMATION: peptide sequence

<400> SEQUENCE: 116

Gln Glu Tyr Asp Glu Ser Gly Pro Ser Ile Val His
1               5                   10

<210> SEQ ID NO 117
<211> LENGTH: 13
<212> TYPE: PRT
<213> ORGANISM: Artificial Sequence
<220> FEATURE:
<223> OTHER INFORMATION: peptide sequence

```
<400> SEQUENCE: 117

Gln Glu Tyr Asp Glu Ser Gly Pro Ser Ile Val His Arg
1               5                   10

<210> SEQ ID NO 118
<211> LENGTH: 13
<212> TYPE: PRT
<213> ORGANISM: Artificial Sequence
<220> FEATURE:
<223> OTHER INFORMATION: peptide sequence

<400> SEQUENCE: 118

Ser Thr Pro Ala Ile Thr Leu Glu Ser Pro Asp Ile Lys
1               5                   10

<210> SEQ ID NO 119
<211> LENGTH: 17
<212> TYPE: PRT
<213> ORGANISM: Artificial Sequence
<220> FEATURE:
<223> OTHER INFORMATION: peptide sequence

<400> SEQUENCE: 119

Ser Thr Pro Ala Ile Thr Leu Glu Ser Pro Asp Ile Lys Tyr Pro Leu
1               5                   10                  15

Arg

<210> SEQ ID NO 120
<211> LENGTH: 12
<212> TYPE: PRT
<213> ORGANISM: Artificial Sequence
<220> FEATURE:
<223> OTHER INFORMATION: peptide sequence

<400> SEQUENCE: 120

Leu Ile Asp Arg Glu Ile Ile Ser His Asp Thr Arg
1               5                   10

<210> SEQ ID NO 121
<211> LENGTH: 10
<212> TYPE: PRT
<213> ORGANISM: Artificial Sequence
<220> FEATURE:
<223> OTHER INFORMATION: peptide sequence

<400> SEQUENCE: 121

Ile Asp Gly Asn Leu Val Val Arg Pro Tyr
1               5                   10

<210> SEQ ID NO 122
<211> LENGTH: 17
<212> TYPE: PRT
<213> ORGANISM: Artificial Sequence
<220> FEATURE:
<223> OTHER INFORMATION: peptide sequence

<400> SEQUENCE: 122

Thr Pro Ile Ser Ser Asp Asp Asp Lys Gly Phe Val Asp Leu Val Ile
1               5                   10                  15

Lys

<210> SEQ ID NO 123
<211> LENGTH: 9
<212> TYPE: PRT
<213> ORGANISM: Artificial Sequence
```

```
<220> FEATURE:
<223> OTHER INFORMATION: peptide sequence

<400> SEQUENCE: 123

Val Tyr Phe Lys Asp Thr His Pro Lys
1               5

<210> SEQ ID NO 124
<211> LENGTH: 11
<212> TYPE: PRT
<213> ORGANISM: Artificial Sequence
<220> FEATURE:
<223> OTHER INFORMATION: peptide sequence

<400> SEQUENCE: 124

Gly Pro Ser Gly Leu Leu Val Tyr Gln Gly Lys
1               5                   10

<210> SEQ ID NO 125
<211> LENGTH: 19
<212> TYPE: PRT
<213> ORGANISM: Artificial Sequence
<220> FEATURE:
<223> OTHER INFORMATION: peptide sequence

<400> SEQUENCE: 125

Ser Val Gly Met Ile Ala Gly Gly Thr Gly Ile Thr Pro Met Leu Gln
1               5                   10                  15

Val Ile Arg

<210> SEQ ID NO 126
<211> LENGTH: 11
<212> TYPE: PRT
<213> ORGANISM: Artificial Sequence
<220> FEATURE:
<223> OTHER INFORMATION: peptide sequence

<400> SEQUENCE: 126

Asp Ile Leu Leu Arg Pro Glu Leu Glu Glu Leu
1               5                   10

<210> SEQ ID NO 127
<211> LENGTH: 9
<212> TYPE: PRT
<213> ORGANISM: Artificial Sequence
<220> FEATURE:
<223> OTHER INFORMATION: peptide sequence

<400> SEQUENCE: 127

Phe Lys Leu Trp Tyr Thr Leu Asp Arg
1               5

<210> SEQ ID NO 128
<211> LENGTH: 7
<212> TYPE: PRT
<213> ORGANISM: Artificial Sequence
<220> FEATURE:
<223> OTHER INFORMATION: peptide sequence

<400> SEQUENCE: 128

Leu Trp Tyr Thr Leu Asp Arg
1               5

<210> SEQ ID NO 129
<211> LENGTH: 18
<212> TYPE: PRT
```

```
<213> ORGANISM: Artificial Sequence
<220> FEATURE:
<223> OTHER INFORMATION: peptide sequence

<400> SEQUENCE: 129

Ala Pro Glu Ala Trp Asp Tyr Gly Gln Gly Phe Val Asn Glu Glu Met
1               5                   10                  15

Ile Arg

<210> SEQ ID NO 130
<211> LENGTH: 7
<212> TYPE: PRT
<213> ORGANISM: Artificial Sequence
<220> FEATURE:
<223> OTHER INFORMATION: peptide sequence

<400> SEQUENCE: 130

Phe Met Leu Asn Glu Val Lys
1               5

<210> SEQ ID NO 131
<211> LENGTH: 9
<212> TYPE: PRT
<213> ORGANISM: Artificial Sequence
<220> FEATURE:
<223> OTHER INFORMATION: peptide sequence

<400> SEQUENCE: 131

Thr Cys Leu Leu Ile Val Phe Ser Lys
1               5

<210> SEQ ID NO 132
<211> LENGTH: 10
<212> TYPE: PRT
<213> ORGANISM: Artificial Sequence
<220> FEATURE:
<223> OTHER INFORMATION: peptide sequence

<400> SEQUENCE: 132

Asp Thr Ala Gly Gln Glu Asp Tyr Asp Arg
1               5                   10

<210> SEQ ID NO 133
<211> LENGTH: 14
<212> TYPE: PRT
<213> ORGANISM: Artificial Sequence
<220> FEATURE:
<223> OTHER INFORMATION: peptide sequence

<400> SEQUENCE: 133

His Phe Cys Pro Asn Val Pro Ile Ile Leu Val Gly Asn Lys
1               5                   10

<210> SEQ ID NO 134
<211> LENGTH: 15
<212> TYPE: PRT
<213> ORGANISM: Artificial Sequence
<220> FEATURE:
<223> OTHER INFORMATION: peptide sequence

<400> SEQUENCE: 134

His Phe Cys Pro Asn Val Pro Ile Ile Leu Val Gly Asn Lys Lys
1               5                   10                  15

<210> SEQ ID NO 135
<211> LENGTH: 9
```

```
<212> TYPE: PRT
<213> ORGANISM: Artificial Sequence
<220> FEATURE:
<223> OTHER INFORMATION: peptide sequence

<400> SEQUENCE: 135

Val Pro Ile Ile Leu Val Gly Asn Lys
1               5

<210> SEQ ID NO 136
<211> LENGTH: 8
<212> TYPE: PRT
<213> ORGANISM: Artificial Sequence
<220> FEATURE:
<223> OTHER INFORMATION: peptide sequence

<400> SEQUENCE: 136

Glu Val Phe Glu Met Ala Thr Arg
1               5

<210> SEQ ID NO 137
<211> LENGTH: 16
<212> TYPE: PRT
<213> ORGANISM: Artificial Sequence
<220> FEATURE:
<223> OTHER INFORMATION: peptide sequence

<400> SEQUENCE: 137

Gly Asp Ser Thr Val Asn Thr Glu Pro Ala Thr Ser Ser Ala Pro Arg
1               5                   10                  15

<210> SEQ ID NO 138
<211> LENGTH: 12
<212> TYPE: PRT
<213> ORGANISM: Artificial Sequence
<220> FEATURE:
<223> OTHER INFORMATION: peptide sequence

<400> SEQUENCE: 138

Thr Ala Ser Ile Ser Glu Thr Pro Val Asp Val Arg
1               5                   10

<210> SEQ ID NO 139
<211> LENGTH: 12
<212> TYPE: PRT
<213> ORGANISM: Artificial Sequence
<220> FEATURE:
<223> OTHER INFORMATION: peptide sequence

<400> SEQUENCE: 139

Ser Asp Glu Glu Glu Pro Lys Asp Glu Ser Ala Arg
1               5                   10

<210> SEQ ID NO 140
<211> LENGTH: 8
<212> TYPE: PRT
<213> ORGANISM: Artificial Sequence
<220> FEATURE:
<223> OTHER INFORMATION: peptide sequence

<400> SEQUENCE: 140

Glu Pro Leu Glu Ala Glu Ala Arg
1               5

<210> SEQ ID NO 141
<211> LENGTH: 7
<212> TYPE: PRT
```

```
<213> ORGANISM: Artificial Sequence
<220> FEATURE:
<223> OTHER INFORMATION: peptide sequence

<400> SEQUENCE: 141

Glu Ser Ala Thr Pro Leu Arg
1               5

<210> SEQ ID NO 142
<211> LENGTH: 18
<212> TYPE: PRT
<213> ORGANISM: Artificial Sequence
<220> FEATURE:
<223> OTHER INFORMATION: peptide sequence

<400> SEQUENCE: 142

Gly Ala Asp Asp Ala Met Glu Ser Ser Lys Pro Gly Pro Val Gln Val
1               5                   10                  15

Val Leu

<210> SEQ ID NO 143
<211> LENGTH: 18
<212> TYPE: PRT
<213> ORGANISM: Artificial Sequence
<220> FEATURE:
<223> OTHER INFORMATION: peptide sequence

<400> SEQUENCE: 143

Ala Arg Ala Ala Pro Asp Pro Pro Leu Phe Asp Asp Thr Ser Gly
1               5                   10                  15

Gly Tyr

<210> SEQ ID NO 144
<211> LENGTH: 16
<212> TYPE: PRT
<213> ORGANISM: Artificial Sequence
<220> FEATURE:
<223> OTHER INFORMATION: peptide sequence

<400> SEQUENCE: 144

Ala Ala Pro Asp Pro Pro Pro Leu Phe Asp Asp Thr Ser Gly Gly Tyr
1               5                   10                  15

<210> SEQ ID NO 145
<211> LENGTH: 11
<212> TYPE: PRT
<213> ORGANISM: Artificial Sequence
<220> FEATURE:
<223> OTHER INFORMATION: peptide sequence

<400> SEQUENCE: 145

Leu Ser Glu Leu Asp Asp Arg Ala Asp Ala Leu
1               5                   10

<210> SEQ ID NO 146
<211> LENGTH: 18
<212> TYPE: PRT
<213> ORGANISM: Artificial Sequence
<220> FEATURE:
<223> OTHER INFORMATION: peptide sequence

<400> SEQUENCE: 146

Leu Ser Glu Leu Asp Asp Arg Ala Asp Ala Leu Gln Ala Gly Ala Ser
1               5                   10                  15

Gln Phe
```

<210> SEQ ID NO 147
<211> LENGTH: 17
<212> TYPE: PRT
<213> ORGANISM: Artificial Sequence
<220> FEATURE:
<223> OTHER INFORMATION: peptide sequence

<400> SEQUENCE: 147

Ala Gln Leu Lys Ser Glu Ala Ala Gly Ser Pro Asp Gln Gly Ser Thr
1               5                   10                  15

Tyr

<210> SEQ ID NO 148
<211> LENGTH: 22
<212> TYPE: PRT
<213> ORGANISM: Artificial Sequence
<220> FEATURE:
<223> OTHER INFORMATION: peptide sequence

<400> SEQUENCE: 148

Gln Ala Gln Leu Thr Gln Ala Gln Ala Glu Gln Pro Ala Gln Ser Ser
1               5                   10                  15

Thr Glu Met Glu Glu Phe
            20

<210> SEQ ID NO 149
<211> LENGTH: 16
<212> TYPE: PRT
<213> ORGANISM: Artificial Sequence
<220> FEATURE:
<223> OTHER INFORMATION: peptide sequence

<400> SEQUENCE: 149

Ser Ser Ser Ala Glu Glu Ser Gly Gln Asp Val Leu Glu Asn Thr Phe
1               5                   10                  15

<210> SEQ ID NO 150
<211> LENGTH: 12
<212> TYPE: PRT
<213> ORGANISM: Artificial Sequence
<220> FEATURE:
<223> OTHER INFORMATION: peptide sequence

<400> SEQUENCE: 150

Asn Ile Asp Val Ala Pro Gly Ala Pro Gln Glu Lys
1               5                   10

<210> SEQ ID NO 151
<211> LENGTH: 18
<212> TYPE: PRT
<213> ORGANISM: Artificial Sequence
<220> FEATURE:
<223> OTHER INFORMATION: peptide sequence

<400> SEQUENCE: 151

Gly Ala Asp Asp Ala Met Glu Ser Ser Lys Pro Gly Pro Val Gln Val
1               5                   10                  15

Val Leu

<210> SEQ ID NO 152
<211> LENGTH: 11
<212> TYPE: PRT
<213> ORGANISM: Artificial Sequence
<220> FEATURE:

<223> OTHER INFORMATION: peptide sequence

<400> SEQUENCE: 152

Ser Val Asn Ala Ile Thr Ala Asp Gly Ser Arg
1               5                   10

<210> SEQ ID NO 153
<211> LENGTH: 7
<212> TYPE: PRT
<213> ORGANISM: Artificial Sequence
<220> FEATURE:
<223> OTHER INFORMATION: peptide sequence

<400> SEQUENCE: 153

Val Phe Leu Asn Ala Lys Lys
1               5

<210> SEQ ID NO 154
<211> LENGTH: 13
<212> TYPE: PRT
<213> ORGANISM: Artificial Sequence
<220> FEATURE:
<223> OTHER INFORMATION: peptide sequence

<400> SEQUENCE: 154

Ala Tyr Pro Ser Asn Ile Thr Ser Glu Thr Gly Phe Arg
1               5                   10

<210> SEQ ID NO 155
<211> LENGTH: 17
<212> TYPE: PRT
<213> ORGANISM: Artificial Sequence
<220> FEATURE:
<223> OTHER INFORMATION: peptide sequence

<400> SEQUENCE: 155

Thr Ala Thr Pro Pro Ala Pro Asp Ser Pro Gln Glu Pro Leu Val Leu
1               5                   10                  15

Arg

<210> SEQ ID NO 156
<211> LENGTH: 16
<212> TYPE: PRT
<213> ORGANISM: Artificial Sequence
<220> FEATURE:
<223> OTHER INFORMATION: peptide sequence

<400> SEQUENCE: 156

Ile Met Ser Ser Asn Ser Ala Ser Ala Ala Asn Gly Asn Asp Ser Lys
1               5                   10                  15

<210> SEQ ID NO 157
<211> LENGTH: 17
<212> TYPE: PRT
<213> ORGANISM: Artificial Sequence
<220> FEATURE:
<223> OTHER INFORMATION: peptide sequence

<400> SEQUENCE: 157

Ile Met Ser Ser Asn Ser Ala Ser Ala Ala Asn Gly Asn Asp Ser Lys
1               5                   10                  15

Lys

<210> SEQ ID NO 158
<211> LENGTH: 8

```
<212> TYPE: PRT
<213> ORGANISM: Artificial Sequence
<220> FEATURE:
<223> OTHER INFORMATION: peptide sequence

<400> SEQUENCE: 158

Thr Ser Val Thr Pro Val Leu Arg
1               5

<210> SEQ ID NO 159
<211> LENGTH: 16
<212> TYPE: PRT
<213> ORGANISM: Artificial Sequence
<220> FEATURE:
<223> OTHER INFORMATION: peptide sequence

<400> SEQUENCE: 159

Ala Gln Ala Ala Leu Gln Ala Val Asn Ser Val Gln Ser Gly Asn Leu
1               5                   10                  15

<210> SEQ ID NO 160
<211> LENGTH: 13
<212> TYPE: PRT
<213> ORGANISM: Artificial Sequence
<220> FEATURE:
<223> OTHER INFORMATION: peptide sequence

<400> SEQUENCE: 160

Gln Ala Val Asn Ser Val Gln Ser Gly Asn Leu Ala Leu
1               5                   10

<210> SEQ ID NO 161
<211> LENGTH: 7
<212> TYPE: PRT
<213> ORGANISM: Artificial Sequence
<220> FEATURE:
<223> OTHER INFORMATION: peptide sequence

<400> SEQUENCE: 161

Thr Ser Leu Asn Val Lys Tyr
1               5

<210> SEQ ID NO 162
<211> LENGTH: 14
<212> TYPE: PRT
<213> ORGANISM: Artificial Sequence
<220> FEATURE:
<223> OTHER INFORMATION: peptide sequence

<400> SEQUENCE: 162

Gly Leu Ser Val Pro Asn Val His Gly Ala Leu Ala Pro Leu
1               5                   10

<210> SEQ ID NO 163
<211> LENGTH: 14
<212> TYPE: PRT
<213> ORGANISM: Artificial Sequence
<220> FEATURE:
<223> OTHER INFORMATION: peptide sequence

<400> SEQUENCE: 163

Ala Ile Pro Ser Ala Ala Ala Ala Ala Ala Ala Ala Gly Arg
1               5                   10

<210> SEQ ID NO 164
<211> LENGTH: 12
<212> TYPE: PRT
```

```
<213> ORGANISM: Artificial Sequence
<220> FEATURE:
<223> OTHER INFORMATION: peptide sequence

<400> SEQUENCE: 164

Pro Ser Ala Ala Ala Ala Ala Ala Ala Gly Arg
1               5                   10

<210> SEQ ID NO 165
<211> LENGTH: 12
<212> TYPE: PRT
<213> ORGANISM: Artificial Sequence
<220> FEATURE:
<223> OTHER INFORMATION: peptide sequence

<400> SEQUENCE: 165

Glu Gly Gln Glu Asp Gln Gly Leu Thr Lys Asp Tyr
1               5                   10

<210> SEQ ID NO 166
<211> LENGTH: 10
<212> TYPE: PRT
<213> ORGANISM: Artificial Sequence
<220> FEATURE:
<223> OTHER INFORMATION: peptide sequence

<400> SEQUENCE: 166

Gln Phe Pro Gly Phe Pro Ala Ala Ala Tyr
1               5                   10

<210> SEQ ID NO 167
<211> LENGTH: 12
<212> TYPE: PRT
<213> ORGANISM: Artificial Sequence
<220> FEATURE:
<223> OTHER INFORMATION: peptide sequence

<400> SEQUENCE: 167

Gly Pro Val Ala Ala Ala Ala Val Ala Ala Ala Arg
1               5                   10

<210> SEQ ID NO 168
<211> LENGTH: 16
<212> TYPE: PRT
<213> ORGANISM: Artificial Sequence
<220> FEATURE:
<223> OTHER INFORMATION: peptide sequence

<400> SEQUENCE: 168

Ser Leu Asp Pro Thr Asn Ala Glu Asn Thr Ala Ser Gln Ser Pro Arg
1               5                   10                  15

<210> SEQ ID NO 169
<211> LENGTH: 12
<212> TYPE: PRT
<213> ORGANISM: Artificial Sequence
<220> FEATURE:
<223> OTHER INFORMATION: peptide sequence

<400> SEQUENCE: 169

Lys Thr Asn Glu Ala Gln Ala Ile Glu Thr Ala Arg
1               5                   10

<210> SEQ ID NO 170
<211> LENGTH: 17
<212> TYPE: PRT
<213> ORGANISM: Artificial Sequence
```

```
<220> FEATURE:
<223> OTHER INFORMATION: peptide sequence

<400> SEQUENCE: 170

Ser Ala Pro Asn Pro Asp Asp Pro Leu Ala Asn Asp Val Ala Glu Gln
1               5                   10                  15
Trp

<210> SEQ ID NO 171
<211> LENGTH: 12
<212> TYPE: PRT
<213> ORGANISM: Artificial Sequence
<220> FEATURE:
<223> OTHER INFORMATION: peptide sequence

<400> SEQUENCE: 171

Lys Thr Asn Glu Ala Gln Ala Ile Glu Thr Ala Arg
1               5                   10

<210> SEQ ID NO 172
<211> LENGTH: 10
<212> TYPE: PRT
<213> ORGANISM: Artificial Sequence
<220> FEATURE:
<223> OTHER INFORMATION: peptide sequence

<400> SEQUENCE: 172

Val Tyr Ser Lys Asp Gln Leu Gln Thr Phe
1               5                   10

<210> SEQ ID NO 173
<211> LENGTH: 14
<212> TYPE: PRT
<213> ORGANISM: Artificial Sequence
<220> FEATURE:
<223> OTHER INFORMATION: peptide sequence

<400> SEQUENCE: 173

Tyr Leu Pro Asp Gly Ser Thr Ile Glu Ile Gly Pro Ser Arg
1               5                   10

<210> SEQ ID NO 174
<211> LENGTH: 13
<212> TYPE: PRT
<213> ORGANISM: Artificial Sequence
<220> FEATURE:
<223> OTHER INFORMATION: peptide sequence

<400> SEQUENCE: 174

Leu Pro Asp Gly Ser Thr Ile Glu Ile Gly Pro Ser Arg
1               5                   10

<210> SEQ ID NO 175
<211> LENGTH: 13
<212> TYPE: PRT
<213> ORGANISM: Artificial Sequence
<220> FEATURE:
<223> OTHER INFORMATION: peptide sequence

<400> SEQUENCE: 175

Ser Leu Ala Thr Gln Asp Ser Asp Asn Pro Asp Leu Arg
1               5                   10

<210> SEQ ID NO 176
<211> LENGTH: 19
<212> TYPE: PRT
```

<213> ORGANISM: Artificial Sequence
<220> FEATURE:
<223> OTHER INFORMATION: peptide sequence

<400> SEQUENCE: 176

Ser Asn Leu Gly Ser Thr Glu Thr Leu Glu Glu Met Pro Ser Gly Ser
1               5                   10                  15

Gln Asp Lys

<210> SEQ ID NO 177
<211> LENGTH: 13
<212> TYPE: PRT
<213> ORGANISM: Artificial Sequence
<220> FEATURE:
<223> OTHER INFORMATION: peptide sequence

<400> SEQUENCE: 177

Leu Asn Gln Pro Val Pro Glu Leu Ser His Ala Ser Leu
1               5                   10

<210> SEQ ID NO 178
<211> LENGTH: 18
<212> TYPE: PRT
<213> ORGANISM: Artificial Sequence
<220> FEATURE:
<223> OTHER INFORMATION: peptide sequence

<400> SEQUENCE: 178

Asn Val Thr Asn Thr Ala Gly Thr Ser Leu Pro Ser Val Asp Leu Leu
1               5                   10                  15

Gln Lys

<210> SEQ ID NO 179
<211> LENGTH: 9
<212> TYPE: PRT
<213> ORGANISM: Artificial Sequence
<220> FEATURE:
<223> OTHER INFORMATION: peptide sequence

<400> SEQUENCE: 179

Leu Gly Ala Glu Glu Ala Lys Thr Phe
1               5

<210> SEQ ID NO 180
<211> LENGTH: 14
<212> TYPE: PRT
<213> ORGANISM: Artificial Sequence
<220> FEATURE:
<223> OTHER INFORMATION: peptide sequence

<400> SEQUENCE: 180

Ile Leu Pro Ser Asp Tyr Asp His Ala Glu Ala Glu Ala Arg
1               5                   10

<210> SEQ ID NO 181
<211> LENGTH: 14
<212> TYPE: PRT
<213> ORGANISM: Artificial Sequence
<220> FEATURE:
<223> OTHER INFORMATION: peptide sequence

<400> SEQUENCE: 181

Val Gly Ser Gln Ala Thr Asp Phe Gly Glu Ala Leu Val Arg
1               5                   10

```
<210> SEQ ID NO 182
<211> LENGTH: 12
<212> TYPE: PRT
<213> ORGANISM: Artificial Sequence
<220> FEATURE:
<223> OTHER INFORMATION: peptide sequence

<400> SEQUENCE: 182

Gly Asn Ser Thr Gly Gly Phe Asp Gly Gln Ala Arg
1               5                   10

<210> SEQ ID NO 183
<211> LENGTH: 20
<212> TYPE: PRT
<213> ORGANISM: Artificial Sequence
<220> FEATURE:
<223> OTHER INFORMATION: peptide sequence

<400> SEQUENCE: 183

Arg Gly Gln Leu Ala Ser Pro Ser Ser Gln Ser Ala Ala Ala Ser Ser
1               5                   10                  15

Leu Gly Pro Tyr
            20

<210> SEQ ID NO 184
<211> LENGTH: 18
<212> TYPE: PRT
<213> ORGANISM: Artificial Sequence
<220> FEATURE:
<223> OTHER INFORMATION: peptide sequence

<400> SEQUENCE: 184

Arg Gly Gln Pro Gly Asn Ala Tyr Asp Gly Ala Gly Gln Pro Ser Ala
1               5                   10                  15

Ala Tyr
```